United States Patent
Erickson et al.

(10) Patent No.: US 11,739,363 B2
(45) Date of Patent: Aug. 29, 2023

(54) DEVICES AND METHODS FOR DETECTING MICROORGANISMS USING RECOMBINANT REPRODUCTION-DEFICIENT INDICATOR BACTERIOPHAGE

(71) Applicant: Laboratory Corporation of America Holdings, Burlington, NC (US)

(72) Inventors: Stephen Erickson, White Bear Township, MN (US); Jose S. Gil, Winnetka, CA (US); Minh Mindy Bao Nguyen, Shoreview, MN (US); Wendy S. Hahn, Hugo, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 265 days.

(21) Appl. No.: 17/003,493

(22) Filed: Aug. 26, 2020

(65) Prior Publication Data

US 2021/0062239 A1    Mar. 4, 2021

Related U.S. Application Data

(60) Provisional application No. 62/891,701, filed on Aug. 26, 2019.

(51) Int. Cl.

| C12Q 1/68 | (2018.01) |
|---|---|
| A61K 39/00 | (2006.01) |
| C07H 21/04 | (2006.01) |
| A61K 48/00 | (2006.01) |
| C07K 14/47 | (2006.01) |
| C12Q 1/10 | (2006.01) |
| C12N 7/00 | (2006.01) |
| C12Q 1/66 | (2006.01) |

(52) U.S. Cl.
CPC ............. *C12Q 1/10* (2013.01); *C12N 7/00* (2013.01); *C12Q 1/66* (2013.01); *C12N 2795/00021* (2013.01)

(58) Field of Classification Search
CPC ....... A61P 35/00; C12N 15/86; C12Q 1/6886; C12Q 2600/158; C12Q 1/703
See application file for complete search history.

(56) References Cited

U.S. PATENT DOCUMENTS

| 5,824,468 A | 10/1998 | Scherer et al. |
| 5,837,465 A | 11/1998 | Squirrel et al. |
| 6,225,066 B1 | 5/2001 | Jacobs, Jr. et al. |
| 7,252,996 B2 | 8/2007 | Boccaccio et al. |
| 8,318,474 B1 | 11/2012 | Smolke et al. |
| 8,557,970 B2 | 10/2013 | Encell et al. |
| 8,865,399 B2 | 10/2014 | Schofield et al. |
| 9,482,668 B2 | 11/2016 | Anderson et al. |
| 10,519,483 B2 | 12/2019 | Anderson et al. |
| 2002/0160525 A1 | 6/2002 | Takahata |
| 2004/0137430 A1 | 7/2004 | Anderson et al. |
| 2004/0197833 A1 | 10/2004 | Loessner |
| 2005/0003346 A1 | 1/2005 | Voorhees et al. |
| 2007/0010001 A1 | 1/2007 | Bujanover |
| 2009/0136984 A1 | 5/2009 | Schutz et al. |
| 2009/0155768 A1 | 6/2009 | Scholl et al. |
| 2009/0246752 A1 | 10/2009 | Voorhees et al. |
| 2010/0291541 A1 | 11/2010 | Evoy et al. |
| 2011/0201013 A1 | 8/2011 | Moore |
| 2011/0281329 A1 | 11/2011 | Lenherr et al. |
| 2013/0122549 A1 | 5/2013 | Lu et al. |
| 2013/0216997 A1 | 8/2013 | Anderson et al. |
| 2015/0218616 A1 | 8/2015 | Anderson et al. |
| 2017/0121688 A1 | 5/2017 | Gil et al. |

FOREIGN PATENT DOCUMENTS

| CN | 104245961 | 5/2017 |
| EP | 0743366 | 11/1996 |
| JP | 11337553 | 12/1999 |
| JP | 2002-160525 | 6/2002 |
| JP | 2005-524394 | 8/2005 |
| JP | 2006-510002 | 3/2006 |
| JP | 2007523628 | 8/2007 |
| JP | 2010-507371 | 3/2010 |
| JP | 2010-088456 | 4/2010 |
| JP | 6636967 | 12/2019 |
| WO | 99/45396 | 9/1999 |
| WO | 03/035889 | 5/2003 |
| WO | 2005/001475 | 1/2005 |
| WO | 2007/055737 | 5/2007 |
| WO | 2008/124119 | 10/2008 |
| WO | 2013/126584 | 8/2013 |
| WO | 2015/126966 | 8/2015 |

(Continued)

OTHER PUBLICATIONS

Akhtar et al., "Isolation, Identification and Characterization of Lytic, Wide Host Range Bacteriophages From Waste Effluents Against Salmonella Enterica Serovars", Food Control, vol. 38, No. 1, Apr. 1, 2014, pp. 67-74.

Bague, J., "Detection of Recombinant Human Erythropoietin and Analogues through Immunorecognition and N-Giycolyi-Neuraminic Acid Identification," Doctoral Thesis Pompeu Fabra University, Department of Experimental and Health Sciences, 2 011. Retrieved from ttg//wwwtesisenred.net/bitstresm/andle/10803/31969/impdf?seggence=1 as available via the Internet and printed Mar. 27, 2013.

Bachrach,U, and Friedman, A., "Practical Procedures for the Purification of Bacterterial Viruses", Applied Microbiology, 22(4):706-715 (1971).

(Continued)

*Primary Examiner* — Barry A Chestnut
(74) *Attorney, Agent, or Firm* — Kilpatrick Townsend & Stockton LLP

(57) ABSTRACT

Disclosed herein are compositions, methods, kits and systems for rapid detection of microorganisms using a reproduction-deficient indicator bacteriophage. The specificity of such reproduction-deficient indicator bacteriophage for binding and infecting particular microorganisms of interest allows targeted and sensitive detection of a microorganism of interest.

26 Claims, 31 Drawing Sheets

(56) References Cited

FOREIGN PATENT DOCUMENTS

WO    2017/127434    7/2017

OTHER PUBLICATIONS

Billard, P. and DuBow, M., "Bioluminescence-Based Assays for Detection and Characterization of Bacteria and Chemicals in Clinical Laboratories", Clinical Biochemistry, 31(1):1-14 (1998).
Edgar, R. et al., :High-sensitivity bacterial detection using biotin-tagged phage and quantum-dot nanocomplexes, Proc. Natl. Acad. Sci. USA, 2006, 103(13):4841-5. Epub Mar. 20, 2006.
Elena et al., "Expression of codon optimized genes in microbial systems: current industrial applications and perspectives. Art. 21", Frontiers in Microbiology, vol. 5, Feb. 1, 2014, pp. 1-8.
Gomez-Torres et al., "Development of a Specific Fluorescent Phage Endolysin for in Situ Detection of Clostridium Species Associated with Cheese Spoilage", Microbial Biotechnology, vol. 11, No. 2, Nov. 21, 2017, pp. 332-345.
Goodridge, L., et al., "Reporter Bacteriophage Assays as a Means to Detect Foodborne Pathogenic Bacteria", Food Research International, vol. 35, No. 9, Jan. 1, 2002, pp. 863-870.
Hagens, S. et al., "Reporter bacteriophage A511::celB transduces a hyperthermostable glycosidase from Pyrococcus furiosus for rapid and simple detection of viable Listeria cells," Bacteriophage, 2011, 1(3):143-151. Epub May 1, 2011.
Hagens, S. et al., "Bacteriophage for Biocontrol of foodborne pathogens: calculations and considerations," Curr. Pharm. Biotechnol., 2010, 11(1):58-68.
He, Y. et al., "Monoclonal antibodies for detection of the H7 antigen of *Escherichia coli*," Appl. Environ Microbiol., 1996, 62(9):3325-32.
Inouye, S. et al., "Overexpression, purification and characterization of the catalytic component of Oplophorus luciferase in the deep-sea shrimp, Oplophorus gracilirostris," Protein Expr. Purif., 2007, 56(2):261-8.
Jacobs, W. et al., "Rapid Assessment of Drug Susceptibilities of *Mycobacterium tuberculosis* by Means of Luciferase Reporter Phases," Science 260(5109):819-822 (1993).
Kodikara, C. et al., "Near on-line detection of enteric bacteria using lux recombinant bacteriophage," FEMS Microbiol. Lett., 1991, 67(3):261-5.
Kong et al., "A Novel and Highly Specific Phage Endolysin Cell Wall Binding Domain for Detection of Bacillus Cereus", European Biophysics Journal, vol. 44, No. 6, Jun. 5, 2015, pp. 437-446.
Kong et al., "Lateral Flow Assay-Based Bacterial Detection using Engineered Cell Wall Binding Domains of a Phage Endolysin", Biosensors and Bioelectronics, vol. 96, May 4, 2017, pp. 173-177.
Kretzer et al., "Use of High-Affinity Cell Wall-Binding Domains of Bacteriophage Endolysins for Immobilization and Separation of Bacterial Cells", Applied and Environmental Microbiology, vol. 73, No. 6, Mar. 15, 2007, pp. 1992-2000.
Kutter et al., "Characterization of a Vil-like Phage 11-20 Specific to *Escherichia coli* 0157:H7", Virology Journal, Biomed Central, London, GB, vol. 8, No. 1, Sep. 7, 2011, pp. 430.
Loessner, M. et al., "Construction of luciferase reporter bacteriophage A511::luxAB for rapid and sensitive detection of viable Listeria cells," Appl. Environ. Microbiol., 1996, 62(4):1133-40.
Loessner, M. et al., "Evaluation of luciferase reporter bacteriophage A511::luxAB for detection of Listeria monocytogenes in contaminated foods," Appl. Environ. Microbiol., 1997, 63(8):2961-5.
Lu, T. et al., "Advancing bacteriophage-based microbial diagnostics with synthetic biology," Trends Biotechnol., 2013, 31(6):325-7.
MacDonald et al., "Regulation of a new bacteriophage T4 gene, 69, that spans an origin of DNA replication", The EMBO Journal, vol. 3 No. 12, 1984, pp. 2863-2871, 8 pages.
Miyanaga et al., "Detection of *Escherichia coli* in the sewage influent by fluorescent labeled T4 phage", Biochemical Engineering Journal, vol. 29, Issues 1-2, Apr. 2006, pp. 119-124, 6 pages.
Noguera, P. et al., "Carbon nanoparticles in lateral flow methods to detect genes encoding virulence factors of Shiga toxin-producing," Anal Bioanal. Chem., 2011, 399(2): 831-838.
Rees C.,The Use of Phage of Diagnostic Systems, Division of Food Sciences, School of Biosciences, University of Nottingham, Sutton Bonington Campus Loughborough, Leicestershire LE12 5RD, UK; The Bacteriophages, 2nd edition (2006) Richard Calendar—Oxford University Press.
Rees et al., "The Use of Phage for Detection, Antibiotic Sensitivity Testing and Enumeration," InTech, In Understanding Tuberculosis-Global Experiences and Innovative Approaches to the Diagnosis, Feb. 15, 2012, 14 pages.
Schofield, D. et al., "Phage-based platforms for the clinical detection of human bacterial pathogens," Bacteriophage, 2012, 2(2):105-283.
Smietana, M. et al., "Detection of bacteria using bacteriophages as recognition elements immobilized on long-period fiber gratings," Opt Express., 2011, 19(9):7971-8.
Tanji et al., "*Escherichia coli* Detection by GFP-labeled Lysozyme-inactivated T4 Bacteriophage", J Biotechnology, vol. 114, No. 1-2, Oct. 19, 2004, pp. 11-20, 10 pages.
Ulitzur, N. et al., "New rapid and simple methods for detection of bacteria and determination of their antibiotic susceptibility by using phage mutants," Appl. Environ. Microbiol., 2006, 72(12 ):7455-7459.
Wu, L. et al., "Trace detection of specific viable bacteria using tetracysteine-tagged bacteriophages," Anal Chem. 2014, 86(1):907-12. Epub Dec. 10, 2013.
Zink, R et al., "Classification of Virulent and Temperate Bacteriophages of *Listeria* spp. on the Basis of Morphology and Protein Analysis," Applied and Environ Microbiol. 58(1):296-302 (1992).
Zuber, S., et al., "Decreasing Enterobacter Sakazakii (*Cronobacter* Spp.) Food Contamination Level With Bacteriophages: Prospects and Problems", Microbial Biotechnology, vol. 1, No. 6, Nov. 1, 2008, pp. 532-543.
PCT/US2019/013543, International Search Report and Written Opinion, dated Apr. 5, 2019, 15 pages.
PCT/US2019/013541, International Search Report and Written Opinion, dated Apr. 5, 2019, 15 pages.
PCT/US2019/013541, International Preliminary Report on Patentability, dated Jul. 23, 2020, 9 pages.
PCT/US2019/013543, International Preliminary Report on Patentability, dated Jul. 23, 2020, 9 pages.
PCT/US2019/021685, International Search Report and Written Opinion, dated Jul. 22, 2019, 19 pages.
PCT/US2019/021685, Invitation to Pay Additional Fees and, Where Applicable, Protest Fee, Jun. 5, 2019, 13 pages.
PCT/US2015/016415, International Search Report and Written Opinion, dated Jun. 22, 2015.
PCT/US13/27155, International Search Report and Written Opinion, dated May 6, 2013.
PCT/US2017/013955, International Preliminary Report on Patentability, dated Aug. 2, 2018, 9 pages.
PCT/US2017/013955, International Search Report and Written Opinion, dated May 15, 2017, 16 pages.
PCT/US2017/013955, Invitation to Pay Additional Fees and Partial Search Report, dated Mar. 20, 2017, 7 pages.
U.S. Appl. No. 13/773,339, Non-Final Office Action, dated Oct. 31, 2014.
U.S. Appl. No. 13/773,339, Final Office Action, dated Jun. 9, 2015.
U.S. Appl. No. 13/773,339, Non-Final Office Action, dated Mar. 3, 2016, 26 pages.
U.S. Appl. No. 14/625,481, Non-Final Office Action, dated Oct. 18, 2016, 10 pages.
U.S. Appl. No. 14/625,481, Non-Final Office Action, dated Jan. 25, 2018, 8 pages.
U.S. Appl. No. 14/625,481, Non-Final Office Action, dated Apr. 26, 2017, 9 Pages.
U.S. Appl. No. 14/625,481, Final Office Action, dated Jun. 13, 2019, 11 pages.
U.S. Appl. No. 15/263,619, Non-Final Office Action, dated Mar. 26, 2018, 19 pages.

(56) References Cited

OTHER PUBLICATIONS

U.S. Appl. No. 15/263,619, Non-Final Office Action, dated May 13, 2019, 21 pages.
U.S. Appl. No. 15/263,619, Final Office Action, dated Feb. 12, 2020, 27 pages.
U.S. Appl. No. 15/409,258, Final Office Action, dated Sep. 17, 2019, 11 pages.
U.S. Appl. No. 15/409,258, Non-Final Office Action, dated Apr. 20, 2020, 6 pages.
AU 2013222411, First Examination Report, dated Nov. 2, 2017, 4 pages.
CA 2,865,308, Office Action, dated Jun. 4, 2019, 3 pages.
CA 2,865,308, Office Action, dated May 1, 2020, 3 pages.
CN 201710263366.1, Office Action, dated Jul. 31, 2019, 10 pages.
CN 201380019483, Office Action, dated Jul. 7, 2015.
CN 201380019483, Office Action, dated Feb. 4, 2016.
CN 201380019483, Office Action, dated Jul. 18, 2016.
EP 13751965.8, Extended European Search Report, dated Sep. 30, 2015, 7 pages.
EP 13751965.8, Communication Pursuant to Article 94(3) EPC, dated Apr. 11, 2017, 6 pages.
EP 13751965.8, Communication Pursuant to Article 94(3) EPC, dated Jan. 30, 2018, 6 pages.
EP 19152164.0, Extended European Search Report, dated Jul. 10, 2019, 6 pages.
EP 17703002.0, Office Action, dated Dec. 18, 2019, 5 pages.
EP 13751965, Extended European Search Report, dated Sep. 30, 2015.
JP 2017-016551, Notice of Reasons for Rejection, dated Jan. 19, 2018, 5 pages.
JP 2017-016551, Office Action, dated Dec. 21, 2018, 12 pages.
JP 2014-558827, Reasons for Rejection, dated Nov. 1, 2016, 9 pages.
JP 2017-16551, Reasons for Rejection, dated Jan. 19, 2018, 5 pages.
JP Application No. 2017-16551, Notice of Allowance, dated Nov. 20, 2019, 3 pages.
JP 2017-16551, Office Action, dated Sep. 6, 2019, 4 pages.
JP 2014-558827, Notice of Reasons for Rejection, dated Nov. 1, 2016.
MX/A/2014/010069, Office Action, dated Apr. 25, 2017, 2 pages.

Plate Layout (Cells/well)

|   | #1 | #2 | #3 | #4 | #5 | #6 | #7 | #8 | #9 | #10 |
|---|---|---|---|---|---|---|---|---|---|---|
| A | 0 | 0 | 0 | 0 | 0 | 0 | X | X | X | X |
| B | 1 | 1 | 1 | 1 | 1 | 1 | 1 | 1 | 1 | 1 |
| C | 2 | 2 | 2 | 2 | 2 | 2 | 2 | 2 | 2 | 2 |
| D | 5 | 5 | 5 | 5 | 5 | 5 | 5 | 5 | 5 | 5 |
| E | 10 | 10 | 10 | 10 | 10 | 10 | 10 | 10 | 10 | 10 |
| F | 100 | 100 | 100 | 100 | 100 | 100 | 100 | 100 | 100 | 100 |
| G | 1000 | 1000 | 1000 | 1000 | 1000 | 1000 | X | X | X | X |
| H | 10000 | 10000 | 10000 | 10000 | 10000 | 10000 | X | X | X | X |

Results (RLU)

|   | #1 | #2 | #3 | #4 | #5 | #6 | #7 | #8 | #9 | #10 |
|---|---|---|---|---|---|---|---|---|---|---|
| A | 80 | 68 | 79 | 57 | 42 | 50 | X | X | X | X |
| B | 109 | 70 | 54 | 96 | 72 | 180 | 218 | 80 | 166 | 62 |
| C | 146 | 122 | 68 | 79 | 126 | 132 | 58 | 128 | 130 | 127 |
| D | 156 | 180 | 559 | 83 | 292 | 159 | 65 | 384 | 124 | 449 |
| E | 543 | 294 | 558 | 244 | 326 | 222 | 345 | 340 | 521 | 230 |
| F | 4378 | 3834 | 4951 | 3576 | 3297 | 3453 | 3976 | 2847 | 3892 | 3483 |
| G | 34534 | 31634 | 34886 | 32652 | 30445 | 33955 | X | X | X | X |
| H | 303135 | 352484 | 367682 | 356626 | 354338 | 364952 | X | X | X | X |

Analysis

|   | Cells/well | Actual CFU | Avg. | SD | Signal-BG | S/B |
|---|---|---|---|---|---|---|
| A | 0 | n/a | 62.7 | 15.6 | 0.0 | 1.0 |
| B | 1 | 1 | 110.7 | 57.0 | 48.0 | 1.8 |
| C | 2 | 1 | 111.6 | 30.9 | 48.9 | 1.8 |
| D | 5 | 5 | 245.1 | 168.2 | 182.4 | 3.9 |
| E | 10 | 9 | 362.3 | 130.9 | 299.6 | 5.8 |
| F | 100 | 118 | 3768.7 | 589.0 | 3706.0 | 60.1 |
| G | 1000 | 1078 | 33017.7 | 1751.3 | 32955.0 | 526.9 |
| H | 10000 | NA | 349869.5 | 23670.0 | 349806.8 | 5583.0 |

FIG. 4

Plate Layout (Cells/well)

|   | 1 | 2 | 3 | 4 | 5 | 6 | 7 | 8 | 9 | 10 |
|---|---|---|---|---|---|---|---|---|---|----|
| A | 0 | 0 | 0 | 0 | 0 | 0 | X | X | X | X |
| B | 1 | 1 | 1 | 1 | 1 | 1 | 1 | 1 | 1 | 1 |
| C | 2 | 2 | 2 | 2 | 2 | 2 | 2 | 2 | 2 | 2 |
| D | 5 | 5 | 5 | 5 | 5 | 5 | 5 | 5 | 5 | 5 |
| E | 10 | 10 | 10 | 10 | 10 | 10 | 10 | 10 | 10 | 10 |
| F | 100 | 100 | 100 | 100 | 100 | 100 | 100 | 100 | 100 | 100 |
| G | 1000 | 1000 | 1000 | 1000 | 1000 | 1000 | X | X | X | X |
| H | 10000 | 10000 | 10000 | 10000 | 10000 | 10000 | X | X | X | X |

Results (RLU)

|   | 1 | 2 | 3 | 4 | 5 | 6 | 7 | 8 | 9 | 10 |
|---|---|---|---|---|---|---|---|---|---|----|
| A | 25 | 28 | 30 | 39 | 24 | 29 | X | X | X | X |
| B | 31 | 22 | 31 | 23 | 30.5 | 30 | 27 | 28 | 28 | 28 |
| C | 29 | 27 | 38.5 | 24 | 26 | 31 | 30 | 33 | 41 | 22 |
| D | 45 | 85 | 25.5 | 43 | 61.5 | 38 | 68 | 56 | 34 | 64 |
| E | 40 | 30.5 | 95 | 76 | 57 | 90 | 31 | 73 | 111 | 141 |
| F | 591 | 299 | 274 | 529 | 452 | 465 | 249 | 634 | 365 | 574 |
| G | 4875 | 4427.5 | 5033 | 5201 | 4881 | 4108 | X | X | X | X |
| H | 54542 | 53600 | 45881 | 53946 | 43529 | 46620 | X | X | X | X |

Limit of Detection Analysis

| Cells/well | Actual CFU/100 ul | Avg. | SD | Signal-BG | S/B |
|---|---|---|---|---|---|
| 0 | - | 29 | 5 | 0 | 1.0 |
| 1 | 0.75 | 28 | 3 | -1 | 1.0 |
| 2 | 1.5 | 30 | 6 | 1 | 1.0 |
| 5 | 4.25 | 52 | 18 | 23 | 1.8 |
| 10 | 6.25 | 74 | 36 | 45 | 2.6 |
| 100 | 86.5 | 443 | 140 | 414 | 15.3 |
| 1000 | 902.5 | 4754 | 408 | 4725 | 163.9 |
| 10000 | - | 49686 | 4875 | 49657 | 1713.3 |

FIG. 16

Plate Layout (Cells/well)

| | 1 | 2 | 3 | 4 | 5 | 6 | 7 | 8 | 9 | 10 |
|---|---|---|---|---|---|---|---|---|---|---|
| A | 0 | 0 | 0 | 0 | 0 | 0 | X | X | X | X |
| B | 1 | 1 | 1 | 1 | 1 | 1 | 1 | 1 | 1 | 1 |
| C | 2 | 2 | 2 | 2 | 2 | 2 | 2 | 2 | 2 | 2 |
| D | 5 | 5 | 5 | 5 | 5 | 5 | 5 | 5 | 5 | 5 |
| E | 10 | 10 | 10 | 10 | 10 | 10 | 10 | 10 | 10 | 10 |
| F | 100 | 100 | 100 | 100 | 100 | 100 | 100 | 100 | 100 | 100 |
| G | 1000 | 1000 | 1000 | 1000 | 1000 | 1000 | X | X | X | X |
| H | 10000 | 10000 | 10000 | 10000 | 10000 | 10000 | X | X | X | X |

Results (RLU)

| | 1 | 2 | 3 | 4 | 5 | 6 | 7 | 8 | 9 | 10 |
|---|---|---|---|---|---|---|---|---|---|---|
| A | 29 | 34 | 30 | 25 | 36 | 33 | X | X | X | X |
| B | 32 | 34 | 37 | 25 | 80 | 40 | 55 | 24 | 27 | 259 |
| C | 34 | 96 | 36 | 115 | 35 | 36 | 32 | 87 | 99 | 112 |
| D | 323 | 32 | 219 | 55 | 147 | 370 | 181 | 270 | 88 | 46 |
| E | 278 | 241 | 198 | 192 | 132 | 753 | 251 | 612 | 609 | 55 |
| F | 2417 | 1736 | 2063 | 2232 | 1731 | 3370 | 2525 | 3018 | 2356 | 3191 |
| G | 27717 | 22872 | 27152 | 26602 | 30464 | 30332 | X | X | X | X |
| H | 329052 | 264393 | 283932 | 316037 | 366558 | 313098 | X | X | X | X |

Limit of Detection Analysis

| Cells/well | Actual CFU/100 ul | Avg. | SD | Signal-BG | S/B |
|---|---|---|---|---|---|
| 0 | - | 31 | 4 | 0 | 1.0 |
| 1 | 0.5 | 61 | 71 | 30 | 2.0 |
| 2 | 1.25 | 68 | 36 | 37 | 2.2 |
| 5 | 4.25 | 173 | 120 | 142 | 5.6 |
| 10 | 4.5 | 332 | 237 | 301 | 10.7 |
| 100 | 69.5 | 2464 | 573 | 2433 | 79.5 |
| 1000 | 675 | 27523 | 2800 | 27492 | 887.8 |
| 10000 | - | 312178 | 35606 | 312147 | 10070.3 |

FIG. 17

Plate Layout (Cells/well)

|   | 1 | 2 | 3 | 4 | 5 | 6 | 7 | 8 | 9 | 10 |
|---|---|---|---|---|---|---|---|---|---|---|
| A | 0 | 0 | 0 | 0 | 0 | 0 | X | X | X | X |
| B | 1 | 1 | 1 | 1 | 1 | 1 | 1 | 1 | 1 | 1 |
| C | 2 | 2 | 2 | 2 | 2 | 2 | 2 | 2 | 2 | 2 |
| D | 5 | 5 | 5 | 5 | 5 | 5 | 5 | 5 | 5 | 5 |
| E | 10 | 10 | 10 | 10 | 10 | 10 | 10 | 10 | 10 | 10 |
| F | 100 | 100 | 100 | 100 | 100 | 100 | 100 | 100 | 100 | 100 |
| G | 1000 | 1000 | 1000 | 1000 | 1000 | 1000 | X | X | X | X |
| H | 10000 | 10000 | 10000 | 10000 | 10000 | 10000 | X | X | X | X |

Results (RLU)

|   | 1 | 2 | 3 | 4 | 5 | 6 | 7 | 8 | 9 | 10 |
|---|---|---|---|---|---|---|---|---|---|---|
| A | 29 | 35 | 27 | 31 | 32 | 26 | X | X | X | X |
| B | 32 | 30 | 25 | 37 | 33 | 80 | 90 | 26 | 30 | 32 |
| C | 45 | 251 | 39 | 34 | 27 | 27 | 27 | 25 | 24 | 21 |
| D | 49 | 295 | 169 | 36 | 76 | 36 | 49 | 181 | 25 | 28 |
| E | 35 | 23 | 36 | 228 | 309 | 39 | 33 | 210 | 749 | 73 |
| F | 1111 | 996 | 1210 | 692 | 685 | 1444 | 572 | 577 | 1255 | 777 |
| G | 10202 | 8298 | 15759 | 17607 | 6346 | 13115 | X | X | X | X |
| H | 124640 | 177757 | 187668 | 174083 | 120522 | 173233 | X | X | X | X |

Limit of Detection Analysis

| Calculated CFU | Actual CFU (100ul) | Avg. | SD | Signal-BG | S/B |
|---|---|---|---|---|---|
| 0 |  | 27.7 | 4.0 | 0.0 |  |
| 1 | 1 | 39.6 | 21.6 | 11.9 | 1.0 |
| 2 | 0.25 | 49.5 | 63.6 | 21.8 | 1.4 |
| 5 | 2.25 | 91.2 | 85.9 | 63.5 | 1.8 |
| 10 | 2.25 | 164.7 | 210.6 | 137.0 | 3.3 |
| 100 | 30.5 | 911.5 | 292.8 | 883.8 | 6.0 |
| 1000 | 246 | 11656.7 | 4050.7 | 11629.0 | 32.9 |
| 10000 | NA | 156886.8 | 27356.8 | 156859.1 | 421.3 |
|  |  |  |  |  | 5670.6 |

FIG. 23

Plate Layout (Cells/well)

|   | 1 | 2 | 3 | 4 | 5 | 6 | 7 | 8 | 9 | 10 |
|---|---|---|---|---|---|---|---|---|---|----|
| A | 0 | 0 | 0 | 0 | 0 | 0 | x | x | x | x |
| B | 1 | 1 | 1 | 1 | 1 | 1 | 1 | 1 | 1 | 1 |
| C | 2 | 2 | 2 | 2 | 2 | 2 | 2 | 2 | 2 | 2 |
| D | 5 | 5 | 5 | 5 | 5 | 5 | 5 | 5 | 5 | 5 |
| E | 10 | 10 | 10 | 10 | 10 | 10 | 10 | 10 | 10 | 10 |
| F | 100 | 100 | 100 | 100 | 100 | 100 | 100 | 100 | 100 | 100 |
| G | 1000 | 1000 | 1000 | 1000 | 1000 | 1000 | x | x | x | x |
| H | 10000 | 10000 | 10000 | 10000 | 10000 | 10000 | x | x | x | x |

Results (RLU)

|   | 1 | 2 | 3 | 4 | 5 | 6 | 7 | 8 | 9 | 10 |
|---|---|---|---|---|---|---|---|---|---|----|
| A | 32 | 49 | 40 | 43 | 40 | 38 | 49 | 52 | 32 | 56 |
| B | 48 | 78 | 28 | 40 | 32 | 32 | 44 | 26 | 69 | 38 |
| C | 57 | 37 | 51 | 37 | 120 | 37 | 197 | 168 | 64 | 136 |
| D | 107 | 46 | 38 | 43 | 131 | 103 | 129 | 157 | 213 | 72 |
| E | 201 | 45 | 165 | 97 | 56 | 296 | 728 | 925 | 731 | 910 |
| F | 1146 | 668 | 987 | 917 | 1150 | 922 | x | x | x | x |
| G | 9085 | 8972 | 8653 | 7673 | 8366 | 10881 | x | x | x | x |
| H | 93249 | 100319 | 95357 | 82888 | 92392 | 96758 | x | x | x | x |

Limit of Detection Analysis

| Calculated Cells | CFU in 100ul | Avg. | SD | Signal-BG | S/B |
|---|---|---|---|---|---|
| 0 | - | 35 | 7.6 | 0 | 1.0 |
| 1 | 1.75 | 41 | 16.8 | 6 | 1.2 |
| 2 | 3.25 | 49 | 24.2 | 13 | 1.4 |
| 5 | 6.75 | 99 | 51.0 | 64 | 2.8 |
| 10 | 9.5 | 143 | 70.9 | 108 | 4.1 |
| 100 | 103.5 | 891 | 159.3 | 856 | 25.3 |
| 1000 | 1114 | 8767 | 1048.6 | 8731 | 249.3 |
| 10000 | - | 91535 | 6013.6 | 91499 | 2602.9 |

FIG. 24

Plate Layout (Cells/well)

|   | #1 | #2 | #3 | #4 | #5 | #6 | #7 | #8 | #9 | #10 |
|---|----|----|----|----|----|----|----|----|----|-----|
| A | 0 | 0 | 0 | 0 | 0 | 0 | X | X | X | X |
| B | 1 | 1 | 1 | 1 | 1 | 1 | 1 | 1 | 1 | 1 |
| C | 2 | 2 | 2 | 2 | 2 | 2 | 2 | 2 | 2 | 2 |
| D | 5 | 5 | 5 | 5 | 5 | 5 | 5 | 5 | 5 | 5 |
| E | 10 | 10 | 10 | 10 | 10 | 10 | 10 | 10 | 10 | 10 |
| F | 100 | 100 | 100 | 100 | 100 | 100 | 100 | 100 | 100 | 100 |
| G | 1000 | 1000 | 1000 | 1000 | 1000 | 1000 | X | X | X | X |
| H | 10000 | 10000 | 10000 | 10000 | 10000 | 10000 | X | X | X | X |

Results (RLU)

|   | 1 | 2 | 3 | 4 | 5 | 6 | 7 | 8 | 9 | 10 |
|---|---|---|---|---|---|---|---|---|---|----|
| A | 35 | 20 | 22 | 36 | 23 | 14 | X | X | X | X |
| B | 26 | 21 | 26 | 31 | 25 | 80 | 20 | 29 | 29 | 27 |
| C | 169 | 16 | 26 | 125 | 26 | 21 | 24 | 27 | 18 | 20 |
| D | 16 | 18 | 22 | 231 | 48 | 61 | 25 | 121 | 99 | 96 |
| E | 141 | 189 | 204 | 123 | 49 | 32 | 20 | 72 | 23 | 16 |
| F | 753 | 546 | 706 | 1050 | 600 | 247 | 791 | 883 | 1109 | 760 |
| G | 9699 | 12267 | 8815 | 11485 | 9010 | 9119 | X | X | X | X |
| H | 104972 | 96113 | 106547 | 105651 | 95729 | 106068 | X | X | X | X |

Limit of Detection Analysis

| Calculated Cells | CFU in 100ul | Avg. | SD | Signal-BG | S/B |
|---|---|---|---|---|---|
| 0 | - | 22.9 | 7.3 | 0.0 | 1.0 |
| 1 | 0.3 | 29.2 | 17.3 | 6.3 | 1.3 |
| 2 | 0.5 | 43.6 | 47.2 | 20.6 | 1.9 |
| 5 | 2.0 | 71.7 | 63.5 | 48.7 | 3.1 |
| 10 | 2.0 | 87.0 | 68.7 | 64.1 | 3.8 |
| 100 | 44.5 | 733.8 | 242.1 | 710.9 | 32.0 |
| 1000 | 378.0 | 9877.5 | 1370.5 | 9854.6 | 431.0 |
| 10000 | - | 100975.3 | 4992.5 | 100952.3 | 4406.2 |

SEA1 NL / SEA1 Δgp84 NL

| | 1 | 2 | 3 | 4 | 5 | 6 | 7 | 8 | 9 | 10 | 11 | 12 |
|---|---|---|---|---|---|---|---|---|---|---|---|---|
| A | 0 | 0 | 0 | 0 | 0 | | | 0 | 0 | 0 | 0 | 0 |
| B | 100 | 100 | 100 | 100 | 100 | | | 100 | 100 | 100 | 100 | 100 |
| C | 1000 | 1000 | 1000 | 1000 | 1000 | | | 1000 | 1000 | 1000 | 1000 | 1000 |
| D | 10000 | 10000 | 10000 | 10000 | 10000 | | | 10000 | 10000 | 10000 | 10000 | 10000 |
| E | 100000 | 100000 | 100000 | 100000 | 100000 | | | 100000 | 100000 | 100000 | 100000 | 100000 |
| F | 1000000 | 1000000 | 1000000 | 1000000 | 1000000 | | | 1000000 | 1000000 | 1000000 | 1000000 | 1000000 |

FIG. 26B

2 HR infection

SEA1 NL / SEA1 Δgp84 NL

| | 1 | 2 | 3 | 4 | 5 | 6 | 7 | 8 | 9 | 10 | 11 | 12 |
|---|---|---|---|---|---|---|---|---|---|---|---|---|
| A | 71 | 55 | 66 | 56 | 72 | | | 51 | 35 | 36 | 55 | 36 |
| B | 9937 | 9637 | 4418 | 1815 | 4597 | | | 1378 | 1537 | 1295 | 1142 | 1232 |
| C | 73843 | 58131 | 41784 | 64706 | 56376 | | | 13968 | 15445 | 12165 | 12844 | 13520 |
| D | 612361 | 636019 | 729363 | 651893 | 580340 | | | 127094 | 128227 | 111629 | 117828 | 138147 |
| E | 19650722 | 14914036 | 19539928 | 18658164 | 19378944 | | | 1404799 | 1353055 | 1347055 | 1294745 | 1513352 |
| F | 417424544 | 406561920 | 418884352 | 419535424 | 420428736 | | | 11741632 | 11411666 | 11183100 | 11142558 | 9569444 |

FIG. 26C

4 HR infection

SEA1 NL / SEA1 Δgp84 NL

| | 1 | 2 | 3 | 4 | 5 | 6 | 7 | 8 | 9 | 10 | 11 | 12 |
|---|---|---|---|---|---|---|---|---|---|---|---|---|
| A | 141 | 143 | 132 | 159 | 320 | | | 461 | 54 | 55 | 50 | 40 |
| B | 1109967 | 250866 | 170519 | 159412 | 244933 | | | 26384 | 31132 | 38565 | 31632 | 36183 |
| C | 5147272 | 8892522 | 4472434 | 7823383 | 7304102 | | | 9921931 | 907629 | 986124 | 1150128 | 960973 |
| D | 377321952 | 370685120 | 382118080 | 387855456 | 394670112 | | | 57480038 | 4952572 | 4879371 | 4987050 | 5245521 |
| E | 112546192 | 116390504 | 112606816 | 111494808 | 108956848 | | | 15495047 | 14872736 | 15232083 | 14316026 | 13108235 |
| F | 86901776 | 82345528 | 83474256 | 82243568 | 77366704 | | | 11078324 | 11021947 | 10750794 | 11729693 | 10968523 |

US 11,739,363 B2

DEVICES AND METHODS FOR DETECTING MICROORGANISMS USING RECOMBINANT REPRODUCTION-DEFICIENT INDICATOR BACTERIOPHAGE

INCORPORATION BY REFERENCE

The present application claims priority to U.S. Provisional Application No. 62/891,701, filed on Aug. 26, 2019. The disclosures of the following U.S. patent applications are hereby incorporated by reference in their entirety: U.S. application Ser. No. 16/247,490, filed on Jan. 14, 2019, U.S. patent application Ser. No. 16/247,486, filed on Jan. 14, 2019, U.S. application Ser. No. 16/298,695, filed on Mar. 11, 2019, U.S. provisional Application No. 62/640,793, filed on Mar. 9, 2018, U.S. provisional Application No. 62/798,980, filed on Jan. 30, 2019, U.S. application Ser. No. 13/773,339, filed on Feb. 21, 2013, U.S. application Ser. No. 14/625,481, filed on Feb. 18, 2015, U.S. application Ser. No. 15/263,619, filed on Sep. 13, 2016, U.S. application Ser. No. 15/409,258, filed on Jan. 18, 2017, U.S. provisional Application No. 62/616,956, filed on Jan. 12, 2018, U.S. provisional Application No. 62/628,616, filed on Feb. 9, 2018, U.S. provisional Application No. 62/661,739, filed on Apr. 24, 2018, U.S. provisional Application No. 62/640,793, filed on Mar. 9, 2018, and U.S. provisional Application No. 62/798,980, filed on Jan. 30, 2019.

FIELD OF THE INVENTION

The disclosure relates to methods, apparatuses, systems for detection of microorganism of interest using recombinant infections agents.

BACKGROUND

There is a strong interest in improving speed and sensitivity for detection of bacteria, viruses, and other microorganisms in biological, food, water, and clinical samples. Microbial pathogens can cause substantial morbidity among humans and domestic animals, as well as immense economic loss. Detection of microorganisms is a high priority for the Food and Drug Administration (FDA) and Centers for Disease Control (CDC) given outbreaks of life-threatening or fatal illness caused by ingestion of food contaminated with certain microorganisms, for example, *Staphylococcus* spp., *Escherichia coli* or *Salmonella* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, to-date, methods reducing the time requirement have drawbacks. For example, techniques involving direct immunoassays or gene probes generally require an overnight enrichment step in order to obtain adequate sensitivity, and therefore lack the ability to deliver same-day results. Polymerase chain reaction (PCR) tests also include an amplification step and therefore are capable of both very high sensitivity and selectivity; however, the sample size that can be economically subjected to PCR testing is limited. Dilute bacterial suspensions capable of being subjected to PCR will be free of cells and therefore purification and/or lengthy enrichment steps are still required.

The time required for traditional biological enrichment is dictated by the growth rate of the target bacterial population of the sample, by the effect of the sample matrix, and by the required sensitivity. In practice, most high sensitivity methods employ an overnight incubation and take about 24 hours overall. Due to the time required for cultivation, these methods can take up to three days, depending upon the organism to be identified and the source of the sample. This lag time is generally unsuitable as such delays allow contaminated food or water or other products to make its way into livestock or humans. In addition, increases in antibiotic-resistant bacteria and biodefense considerations make rapid identification of bacterial pathogens in water, food, and clinical samples critical priorities worldwide.

Therefore, there is a need for more rapid, simple and sensitive detection and identification of microorganisms, such as bacteria and other potentially pathogenic microorganisms.

SUMMARY

Embodiments of the disclosure comprise devices, compositions, methods, apparatuses, systems, and kits for the detection of microorganisms, such as, but not limited to bacteria. The disclosure may be embodied in a variety of ways. Some exemplary embodiments of the present application are discussed below.

An exemplary embodiment of the present disclosure is a recombinant phage comprising an indicator gene in a late gene region of genome of the phage, wherein the recombinant phage is reproduction-deficient, and wherein the recombinant phage is capable of specifically infecting a microorganism of interest. In some embodiments, the recombinant bacteriophage is reproduction-deficient due to an alteration in a late gene required for virion assembly. In some embodiments of the recombinant bacteriophage, the indicator gene is inserted into a sequence of a late gene of the recombinant phage, rendering the late gene non-functional and the recombinant phage reproduction-deficient. In some embodiments of the recombinant bacteriophage, the indicator gene replaces at least a portion of a sequence of a late gene of the recombinant phage, rendering the recombinant phage reproduction deficient, wherein the late gene is required for virion assembly. recombinant phage is derived from a phage specific for *E. coli*, or *Salmonella*, or *Listeria*, or *Staphylococcus*. In some embodiments, the recombinant phage is derived from a phage specific for *E. coli*. In other embodiments, the recombinant phage is derived from a phage specific for *Salmonella*. In some embodiments of the recombinant bacteriophage, the late gene is required for virion assembly.

An exemplary embodiment of the present disclosure is a composition comprising at least two recombinant phages, each comprising an indicator gene in a late gene region of genome of the phage, wherein the recombinant phages are reproduction-deficient, and wherein the recombinant phages are capable of specifically infecting one or more microorganism of interest. In some embodiments of the composition, each of the at least two recombinant phages comprises a different indicator gene. In some embodiments of the composition, each of the at least two recombinant phages is capable of specifically infecting a different microorganism of interest. In some embodiments of the composition, the at least two recombinant phages are capable of infecting a plurality of microorganisms of interest. In some embodiments of the composition, the plurality of the microorganisms of interest comprises at least two different categories of bacteria. In some embodiments of the composition, the at least two different categories of bacteria comprise one or more of at least two different genera of bacteria, at least two different species of bacteria, at least two different strains of bacteria or at least two different serotypes of bacteria.

An exemplary embodiment of the present disclosure is a method of preparing a recombinant phage. Such method may comprise the steps of: selecting a parent phage that specifically infects a target microorganism; altering a gene of the parent page to generate a recombinant reproduction-deficient phage; transforming an engineered strain of the target microorganism capable of expressing a product of the gene mutated in the reproduction-deficient phage with a homologous recombination (HR) plasmid comprising an indicator gene and HR sequences flanking the indicator gene and homologous to a desired sequence in the parent phage; infecting the transformed target microorganism with the parent phage or the reproduction-deficient parent phage, allowing HR to occur between the HR plasmid and the genome or the parent phage or the recombinant reproduction-deficient phage; and isolating a particular clone of recombinant phage that is both reproduction-deficient and is capable of expressing a product of the indicator gene. In some embodiments of a method of preparing a recombinant phage, the altering of the gene of the parent page to generate the reproduction-deficient phage is accomplished by the HR occurring between the HR plasmid and the genome of the parent phage, wherein the gene of the parent phage is altered by a replacement of at least a part of the parent phage by the indicator gene. In some embodiments, altering of the gene comprises deletion of a gene of the parent phage in-part or in-whole. Thus, in some embodiments, the method comprises altering the genome of the parent phage, wherein at least one gene of the parent phage is deleted. In some embodiments, at least two, three, four, or five gens are deleted.

Some embodiments of a method of preparing a recombinant phage may further comprise a step of generating the engineered strain of the target microorganism. In some embodiments, the step of generating of the engineered strain of the target microorganism may comprise a step of transforming the target microorganism with a plasmid encoding and capable of expressing the gene altered in the recombinant reproduction-deficient phage ("trans plasmid"). Some embodiments of a method of preparing a recombinant phage may further comprise, prior to the transforming step, a step of preparing the homologous recombination plasmid comprising the indicator gene. In some embodiments, the step of generating the engineered strain of the target microorganism may comprise a step of transforming the target microorganism with the trans plasmid and the HR plasmid comprising the indicator gene. In some embodiments of a method of preparing a recombinant phage, the altering of the gene of the parent page to generate the reproduction-deficient phage is accomplished by the infection with a wild-type parent phage of an engineered target microorganism containing both trans plasmid and the HR plasmid, so HR may occur between the HR plasmid and the genome of the parent phage, wherein the gene of the parent phage is altered by replacement of at least a part of the parent phage by the indicator gene, while the plasmid containing the gene altered in the reproduction-deficient recombinant phage (trans plasmid) provides the gene in trans, complementing the missing or altered gene in the reproduction-deficient phage. In further embodiments of a method of preparing a recombinant phage, the deleting of the gene of the parent page to generate the reproduction-deficient phage is accomplished by the infection with a wild-type parent phage of an engineered target microorganism containing both trans plasmid and the HR plasmid, so HR may occur between the HR plasmid and the genome of the parent phage, wherein the genome of the parent phage is altered by replacement of at least a part of the parent phage by the indicator gene, while the plasmid containing the gene altered in the reproduction-deficient recombinant phage (trans plasmid) provides the gene in trans, complementing the missing or altered gene in the reproduction-deficient phage.

In some embodiments of a method of preparing a recombinant phage, the altering of the gene of the parent page to generate the reproduction-deficient phage is accomplished by the infection with a wild-type parent phage of an engineered target microorganism not containing a plasmid encoding and capable of expressing the gene altered in the reproduction-deficient phage, yet containing the HR plasmid so HR may occur between the HR plasmid and the genome of the parent phage, wherein the gene of the parent page is altered by a replacement of at least a part of the parent phage by the indicator gene, while wild-type parental phage infecting or co-infecting the bacteria provides the said gene in trans, complementing the missing or altered gene in the reproduction-deficient phage.

In some embodiments, the step of isolating the particular clone of recombinant phage that is both reproduction-deficient and is capable of expressing the product of the indicator gene may comprise performing a limiting dilution assay for isolating a clone that demonstrates expression of the indicator gene. recombinant phage is derived from a phage specific for *E. coli*, or *Salmonella*, or *Listeria*, or *Staphylococcus*. In some embodiments of a method of preparing a recombinant phage, the recombinant phage is derived from a phage specific for *Escherichia coli*. In some embodiments of a method of preparing a recombinant phage, the recombinant phage is derived from a phage specific for *Salmonella*.

An exemplary embodiment of the present disclosure is a method of detecting the microorganism of interest in a sample, comprising the steps of: incubating a sample with the recombinant phage according to the embodiments of the present disclosure; and, detecting a product of the indicator gene, wherein positive detection of the product of the indicator gene indicates that the microorganism of interest is present in the sample. In some embodiments of a method of detecting the microorganism of interest in a sample, the sample may be a food, environmental, water, or commercial sample. In some embodiments of a method of detecting the microorganism of interest in a sample, the method detects as few as 10, 9, 8, 7, 6, 5, 4, 3, 2, or a single microorganism in the sample. In some embodiments of a method of detecting the microorganism of interest in a sample, the microorganism of interest is *Escherichia coli*. In some embodiments of a method of detecting the microorganism of interest in a sample, the microorganism of interest is *Salmonella*.

Also included among the exemplary embodiments of the present disclosure is a kit for detecting the microorganism of interest in a sample, the kit comprising the recombinant phage according to the embodiments of the present disclosure and a substrate for reacting with a product of the indicator gene to detect the product of the indicator gene. Also included among the exemplary embodiments of the present disclosure is a system for detecting the microorganism of interest comprising the recombinant phage of claim 1 and a components for detecting a product of the indicator gene.

BRIEF DESCRIPTION OF THE FIGURES

The present disclosure may be better understood by referring to the following non-limiting figures.

FIG. 4 is a table illustrating the limit of detection of CBA120.Δgp22.NanoLuc reproduction-deficient indicator phage in stationary phase *E. coli* O157:H7 ATCC 43888.

FIG. 16 is a table illustrating the limit of detection of SP1.Δgp22.NanoLuc reproduction-deficient indicator phage in stationary phase *Salmonella typhimurium* ATCC 19585.

FIG. 17 is a table illustrating the limit of detection of SP1.Δgp22.NanoLuc reproduction-deficient indicator phage in log phase *Salmonella typhimurium* ATCC 19585.

FIG. 23 is a table illustrating the limit of detection of SEA1.Δgp84.NanoLuc reproduction-deficient indicator phage in log phase *Salmonella newport* ATCC 27869 transformed with AmpR pUC57 SEA1.Trans gp84.

FIG. 24 is a table illustrating the limit of detection of SEA1.Δgp84.NanoLuc reproduction-deficient indicator phage in stationary phase *Salmonella chloreaesuis* ATCC 7001.

FIG. 25 is a table illustrating the limit of detection of SEA1.Δgp84.NanoLuc reproduction-deficient indicator phage in log phase *Salmonella chloreaesuis* ATCC 7001.

FIG. 26A is a table illustrating the approximate number of SEA1.NanoLuc replicating phage and SEA1.Δgp84.NanoLuc non-replicating CFUs per well. FIG. 26B is a table illustrating the RLU signal results of the detection assay using the replicating phage and SEA1.Δgp84.NanoLuc compared to reproduction-deficient indicator phage compared to SEA1.NanoLuc replicating phage specific for *Salmonella typhimurium* following a 2 hour infection. FIG. 26C is a table illustrating the RLU signal results of the detection assay using the replicating phage and SEA1.Δgp84.NanoLuc compared to reproduction-deficient indicator phage compared to SEA1.NanoLuc replicating phage specific for *Salmonella typhimurium* following a 4 hour infection.

DETAILED DESCRIPTION OF THE INVENTION

Definitions

Figure 1:
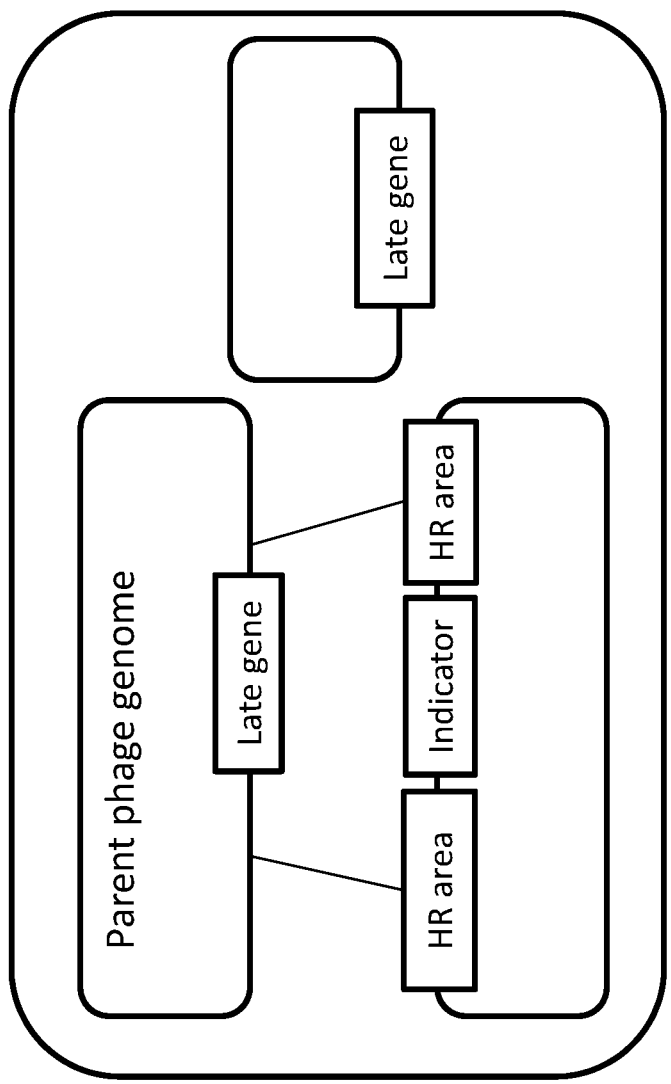
FIG. 1 schematically illustrates an exemplary method for preparing a recombinant reproduction-deficient indicator phage, in which the introduction of the reproduction-deficiency and of the indicator gene into the parent phage is accomplished in a one-step recombination process.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well-known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (that is, such as a microtiter plate or multi-well plate), or the solid support may be a location on a filter, an array, or a mobile support, such as a bead or a membrane (for example, a filter plate or lateral flow strip).

The term "binding agent" refers to a molecule that can specifically and selectively bind to a second (that is, different) molecule of interest. The interaction may be non-covalent, for example, as a result of hydrogen bonding, van der Waals interactions, or electrostatic or hydrophobic interactions, or it may be covalent. The term "soluble binding agent" refers to a binding agent that is not associated with (that is, covalently or non-covalently bound) to a solid support.

As used herein, the terms "reproduction defective" or "reproduction deficient" or "replication defective" or "replication deficient" refer to an impairment in the ability of bacteriophage to reproduce. That is, reproduction defective bacteriophage may be unable to generate new bacteriophage particles, for example due to missing proteins needed for assembly of the capsid. A variety of deletions, insertions, or substitutions in the bacteriophage genome can render the bacteriophage reproduction defective.

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator" or "indicator moiety" refers to a molecule or a compound produced by a molecule (such as an enzyme) that can be measured in a quantitative assay. For example, an indicator or indicator moiety may comprise an enzyme that may be used to convert a substrate to a product that can be measured. An indicator or indicator moiety may be an enzyme that catalyzes a reaction that generates bioluminescent emissions (for example, luciferase). Or, an indicator or indicator moiety may be a radioisotope that can be quantified. Or, an indicator moiety may be a fluorophore. Or, other detectable molecules may be used. The term "indicator gene" is used to refer to a gene encoding an indicator, such as a protein, for example, an enzyme.

As used herein, "phage" includes one or more of a plurality of viruses that can invade living bacteria, fungi, *mycoplasma*, protozoa, yeasts, and other microscopic living organisms. In this disclosure, the term and "phage" and the related terms include viruses such as bacteriophages, which can invade bacteria and archaea, mycobacteriophages, which can invade mycobacteria (a family bacteria, which includes the mycobacteria of *Mycobacterium tuberculosis* complex, including the causative agents of tuberculosis, and the mycobacteria of *Mycobacterium avis* complex, including the causative agents of tuberculosis), mycophages, which can invade fungi, *mycoplasma* phages, as well as the viruses that my infect protozoa, yeasts, and other microscopic living organisms. Here, "microscopic" means that the largest dimension is one millimeter or less. Bacteriophages are viruses that have evolved in nature to use bacteria, mycobacteria or archaea as a means of replicating themselves. In nature, phage attaches itself to a microorganism and injects its DNA (or RNA) into that microorganism, and then can induce the microorganism to replicate the phage hundreds or even thousands of times. This is referred to as phage amplification. For example, well-studied phages of *Escherichia coli* include T1, T2, T3, T4, T5, T7, and lambda; other *E. coli* phages available in the ATCC collection, for example, include phiX174, S13, Ox6, MS2, phiV1, fd, PR772, and ZIK1. *Salmonella* phages include TSP1, TSP11, SPN1S, 10, epsilon15, SEA1, TSP1, and P22. *Listeria* phages include P100, LMA8, LMA4, LPES1, LipZ5, P40, vB_LmoM_AG20, P70, P100, LP-JS3, LP-ES1, and A511. *Staphylococcus* phages include staph phage ISP, P4 W, virus K, Twort, phi11, 187, P68, and phiWMY.

As used herein, "late gene region" refers to a region of a viral genome that is transcribed late in the viral life cycle. The late gene region typically includes the most abundantly expressed genes (for example, structural proteins assembled into the bacteriophage particle). Late genes of bacteriophages are synonymous with class III genes and include genes with structure and assembly functions. For example, the late genes (synonymous with class III,) are transcribed in phage T7, for example, from 8 minutes after infection until lysis, class I (for example, RNA polymerase) is early from 4-8 minutes, and class II from 6-15 minutes, so there is overlap in timing of II and III. A late promoter is one that is naturally located and active in such a late gene region.

As used herein, "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for periods of time may be employed in some embodiments of methods described herein.

As used herein "recombinant" refers to genetic (that is, nucleic acid) modifications as usually performed in a laboratory to bring together genetic material that would not otherwise be found. This term is used interchangeably with the term "modified" herein. As used herein "RLU" refers to relative light units as measured by a luminometer (for example, GLOMAX® 96) or similar instrument that detects light. For example, the detection of the reaction between luciferase and appropriate substrate (for example, NANO-LUC® with NanoGlo) is often reported in RLU detected.

Overview

Disclosed herein are compositions, methods and systems that demonstrate surprising sensitivity for detection of a microorganism of interest, such as bacteria and archaea, in test samples (for example, biological, food, water, and environmental). Some non-limiting examples of the microorganisms of interest are *Bacillus* spp., *Bordetella pertussis*, *Brucella* spp., *Camplylobacter* spp. (such as *Campylobacter jejuni*), *Chlamydia pneumoniae*, *Cronobacter* spp., *Clostridium perfringens*, *Clostridium botulinum*, *Enterobacter* spp., *Escherichia* spp. (such as *Escherichia coli*, for example, *E. coli* O157:H7 and other Shiga toxin—and enterotoxin-producing strains of *Escherichia coli*), *Klebsiella pneumoniae*, *Klebsiella oxytoca*, *Listeria* spp. (such as *Listeria monocytogenes*), *Mycoplasma pneumoniae*, *Pseudomonas* spp., *Salmonella* spp. (for example, *Salmonella typhi*, *Salmonella typhimurium* or *Salmonella enteritidis*), *Shigella sonnei*, *Yersinia* spp., *Vibrio* spp. *Staphylococcuss* spp. (for example, *Staphylococcus aureus*), and *Streptococcus* spp. Detection can be achieved in a shorter timeframe than was previously thought possible using genetically modified phages in assays performed without culturing for enrichment, or in some embodiments with minimal incubation times during which microorganisms could potentially multiply. Also surprising is the success of using a potentially high multiplicity of infection (MOI), or high concentrations of plaque forming units (PFU), for incubation with a test sample. Such high phage concentrations (PFU/mL) were previously purported to be detrimental in bacterium detection assays, as they were purported to cause "lysis from without." However, a high concentration of phage can facilitate finding, binding, and infecting a low number of target cells.

The compositions, methods, systems and kits of the invention may comprise recombinant phages for use in detection of a microorganism of interest. In certain embodiments, the invention may comprise a composition comprising a recombinant phage having an indicator gene inserted into a late gene region of the phage. Such recombinant phage is referred to as "indicator phage." In certain embodiments, expression of the indicator gene following infection of a host microorganism results in production of a soluble indicator protein product. In certain embodiments, the indicator gene may be inserted into a late gene (that is, class III) region of the bacteriophage. The recombinant bacteriophages according to the embodiments of the present invention can be derived from podoviruses such as T7, T7-like, myoviruses such as T4, T4-like, siphoviruses, such as T5, P70, Saka6, and related phages, ViI, ViI-like (or Vi1 virus, per GenBank/NCBI), *Cronobacter* spp, -specific bacteriophages, such as Saka2 or Saka4, *Salmonella* phage SPN1S, *Salmonella* phage 10, *Salmonella* phage epsilon 15, *Salmonella* phage SEA1, *Salmonella* phage Spn1s, *Salmonella* phage P22, *Listeria* phage LipZ5, *Listeria* phage P40, *Listeria* phage vB_LmoM_AG20, *Listeria* phage P70, *Listeria* phage A511, *Staphylococcus* phage P4 W, *Staphylococcus* phage K, *Staphylococcus* phage Twort, *Staphylococcus* phage SA97, *Escherichia coli* O157:H7 phage CBA120, or another wild-type or engineered bacteriophage.

Indicator phages according to the embodiments of the invention are reproduction-deficient, meaning that they are unable to reproduce efficiently or at all after infecting a microorganism of interest being detected. Reproduction-deficient indicator phages according to the embodiments of the present invention are rendered reproduction-deficient due to alteration of one or more of the suitable genes, for example, late genes required for virion assembly. In some embodiments, the reproduction-deficient indicator phages according to the embodiments of the present invention are rendered reproduction-deficient by introducing a mutation in a suitable gene separately from introduction of the indicator gene. In some other embodiments, the reproduction-deficient indicator phages according to the embodiments of the present invention are rendered reproduction-deficient by replacing at least a part of a suitable gene by an indicator gene. Reproduction-deficient indicator phages according to the embodiments of the present invention can be propagated or reproduced in host microorganisms engineered to produce a product of the mutated gene needed for phage reproduction. Such engineered microorganisms are termed "permissive."

Reproduction-deficient indicator phages possess several advantages over the previously described indicator phages. Since reproduction-deficient indicator phages require special engineered microorganisms for reproduction, the potential for their production and distribution by unexperienced and/or untrained providers is limited. Production and distribution of tainted and low-quality reagents is a serious problem in the field of diagnostics. By limiting the production and distribution of indicator phages to entities possessing certain qualifications and meeting certain standards (for example, through official certification processes), providing reproduction-deficient indicator phages reduces the risks of low-quality or tainted indicator phages being produced and distributed to diagnostic operators. Furthermore, being unable to reproduce in the host microorganisms found in the environment, reproduction-deficient indicator phages eliminate the risk that standardized diagnostic reagents containing defined concentrations and/or amounts of indicator phages would be contaminated by host microorganisms prior to the performance of the diagnostic procedures, which can lead to undetected increases in the concentration or amount of the indicator phages in the reagents and, as a consequence, to inaccurate detection data. This issue is particularly important during quantitative or semi-quantitative detection, when the concentration or amount of the indicator phage being used correlates with the strength of the signal being detected. Still further, due to inability to reproduce in a microorganism of interest during the diagnostic process, reproduction-deficient indicator phages according to the embodiments of the present invention allow for more accurate quantitative or semi-quantitative detection of the microorganisms of interest in a sample. The improvements in accuracy result from the ability to control the amounts of reproduction-deficient indicator phages found in the sample throughout the detection process. Since no new viable indicator phages are being generated during the detection process, only the initially used reproduction-deficient indicator phages are capable of expressing the indicator gene product post-infection. Deletion of and replacement of a late gene compared to an early gene assures high expression of the indicator gene, both due to the high expression levels inherent in late genes, and because deletion of an early gene often results in no genome replication, reducing the copy number of the indicator gene in each cell. Reproduction of the indicator pages post-infection can introduce significant variability into the amounts of the indicator signal being produced during the diagnostic process. Thus, using reproduction-deficient indicator phages according to the embodiments of the present invention leads to easier standardization of quantitative and semi-quantitative detection, improving the accuracy of the detection results.

In some aspects, the invention comprises a method for detecting a microorganism of interest. The method may use a phage for detection of the microorganism of interest. Thus, in certain embodiments, the method may comprise detection of a microorganism of interest in a sample by incubating the sample with a recombinant reproduction-deficient indicator phage that infects the microorganism of interest. In some embodiments, a recombinant reproduction-deficient indicator phage is a bacteriophage. The indicator gene may, in certain embodiments, be inserted into a late gene region of the bacteriophage, such that the expression of the indicator gene following infection of host microorganism results in production of an indicator gene product. The method may comprise detecting the indicator gene product, wherein positive detection of the indicator gene product indicates that the microorganism of interest is present in the sample. In some embodiment the indicator gene product is a protein. In some embodiment the indicator gene product is a soluble protein.

In certain embodiments, the invention may comprise a system. The system may contain at least some of the compositions of the invention. Also, the system may comprise at least some of the components for performing the method. In certain embodiments, the system is formulated as a kit. Thus, in certain embodiments, the invention may comprise a system for rapid detection of a microorganism of interest in a sample, comprising: a component for incubating the sample with a reproduction-deficient indicator phage specific for the microorganism of interest, wherein the reproduction-deficient indicator phage comprises an indicator gene; and a component for detecting the indicator. In yet other embodiments, the invention comprises software for use with the methods or systems.

Some embodiments of the present invention solve a need in the field of microorganism detection by using bacterio-phage-based methods for amplifying a detectable signal indicating the presence of bacteria. In certain embodiments as little as a single bacterium is detected. The principles applied herein can be applied to the detection of a variety of microorganisms. Because of numerous binding sites for phages on the surface of a microorganism and the potential for high level expression of an encoded indicator, the indicator can be more readily detectable than the microorganism itself. In this way, embodiments of the present invention can achieve tremendous signal amplification from even a single infected cell.

Some embodiments of the invention disclosed and described herein utilize the fact that a single microorganism is capable of binding multiple recombinant reproduction-deficient indicator phages according to the embodiments of the present invention. Following infection by the recombinant reproduction-deficient indicator phages, they are detected via an indicator encoded by the recombinant reproduction-deficient indicator phages and expressed in the microorganism. This principle allows amplification of indicator signal from one or a few cells based on specific recognition of microorganism surface receptors. For example, by exposing even a single cell of a bacterium to a plurality of reproduction-deficient indicator phages, thereafter allowing expression of an encoded indicator gene product, the indicator signal is amplified such that a microorganism of interest is detectable with high sensitivity. For example, a single bacterium present in a sample may be detectable using the embodiments of the present invention. Embodiments of the present invention utilize the high specificity of phages that can bind to particular microorganisms as a way to detect and/or quantify specific microorganism in a sample. In some embodiments, the present invention utilizes high specificity of the reproduction-deficient indicator phages.

Embodiments of the methods and systems of the invention can be applied to detection and quantification of a variety of microorganisms (such as, but not limited to, bacteria and archaea) in a variety of circumstances, including but not limited to detection of pathogens from food, water, and commercial samples. The methods of the present invention provide high detection sensitivity and specificity and rapid detection.

Samples

Each of the embodiments of the compositions, methods, kits, and systems of the invention allows for the rapid detection and/or quantification of microorganisms of interest in a sample. For example, methods according to the embodiments of present invention can be performed in a shortened time period with superior results.

Microorganism detectable in samples using embodiments of the present invention include, but are not limited to, bacteria that are food- or water-borne pathogens. Bacteria detectable by the present invention include, but are not limited to, *Bacillus* spp., *Bordetella pertussis*, *Brucella* spp., *Camplylobacter* spp. (such as *Campylobacter jejuni*), *Chlamydia pneumoniae*, *Cronobacter* spp., *Clostridium perfringens*, *Clostridium botulinum*, *Enterobacter* spp., *Escherichia* spp. (such as *Escherichia coli*, for example, *E. coli* O157:H7 and other Shiga toxin—and enterotoxin-producing strains of *Escherichia coli*), *Klebsiella pneumoniae*, *Listeria* spp. (such as *Listeria monocytogenes*), *Mycoplasma pneumoniae*, *Salmonella* spp. (for example, *Salmonella typhi*, *Salmonella typhimurium* or *Salmonella enteritidis*), *Shigella sonnei*, *Yersinia* spp., *Vibrio* spp. *Staphylococcus* spp. (for example, *Staphylococcus aureus*), and *Streptococcus* spp.

A sample may be, but is not limited to, an environmental, sample, a food sample or a water sample. Some embodiments may include medical or veterinary samples. Samples may be liquid, solid, or semi-solid. Samples may be swabs of solid surfaces. Samples may include environmental materials, such as water samples, or the filters from air samples, or aerosol samples from cyclone collectors. Samples may be samples of fish, meet, such as beef, pork or lamb, poultry, processed foods, peanut butter, powdered infant formula, powdered milk, teas, starches, eggs, milk, cheese, or other dairy products. Medical or veterinary samples include, but are not limited to, blood, sputum, cerebrospinal fluid, fecal samples, and irrigation washes. some embodiments, irrigation is used to collect biological samples. Irrigation is the flow of a solution (e.g., saline) across an open wound or implanted prosthetic. Thus in some embodiments, the biological sample is a wound irrigant or prosthetic irrigant. In some embodiments, samples may be different types of swabs.

In some embodiments, samples may be used directly in the detection methods according to the embodiments of the present invention, without preparation, concentration, or dilution. For example, liquid samples, including but not limited to, milk and juices, may be assayed directly. In other embodiments, samples may be diluted or suspended in solution, which may include, but is not limited to, a buffered solution or a bacterial culture medium. A sample that is a solid or semi-solid may be suspended in a liquid by mincing, mixing or macerating the solid in the liquid. In some embodiments, a sample should be maintained within a pH range that promotes recombinant bacteriophage attachment to the host bacterial cell. In some embodiments, the preferred pH range may be one suitable for bacteriophage attached to a bacterial cell. A sample should also contain the appropriate concentrations of divalent and monovalent cations, including but not limited to $Na^+$, $Mg^{2+}$, and $K^+$.

In some embodiments, the sample is maintained at a temperature that maintains the viability of any pathogen cell present in the sample. During steps in which bacteriophages are attaching to bacterial cells, the sample may be maintained at a temperature that facilitates bacteriophage activity. Such temperatures are at least about 25° C. and no greater than about 45° C. In some embodiments the sample is maintained at about 37° C. In some embodiments the samples are subjected to gentle mixing or shaking during recombinant bacteriophage binding or infection.

Embodiments of the present invention may utilize various appropriate control samples. For example, control samples containing no phages or control samples containing phages without microorganisms of interest may be assayed as controls for background signal levels.

Reproduction-Deficient Indicator Phage

As described in more detail herein, the compositions, methods, systems and kits according to the embodiments of the present invention may comprise reproduction-deficient indicator phages for use in detection of pathogenic microorganisms. In certain embodiments, the invention comprises a recombinant reproduction-deficient indicator bacteriophage with a genetic modification or modifications to include an indicator gene and render the phage reproduction-deficient. The above genetic modifications may be introduced during one genetic modification steps or during multiple genetic modification steps (such as two or more genetic modification steps). In some embodiments, the invention may include compositions comprising reproduction-deficient indicator phages.

A recombinant reproduction-deficient indicator phage can include a reporter or indicator gene. In certain embodiments of the infectious agent, the indicator gene does not encode a fusion protein. For example, in certain embodiments, expression of the indicator gene following infection of a host microorganism, such as bacterium, results in a soluble indicator protein product. In certain embodiments, the indicator gene may be inserted into a late gene region of the reproduction-deficient indicator phage. Late genes are generally expressed at higher levels than other phage genes, as they code for structural proteins.

Recombinant reproduction-deficient indicator-phages according to the embodiments of the present invention comprise alterations that make the recombinant pages unable to reproduce upon infecting the host organisms. Suitable genes and alterations are selected according to a number of considerations. Phage gene suitable for alterations are the genes affecting the phages ability to reproduce in the host microorganism post-infection, but not affecting the ability of the recombinant reproduction-deficient phage to infect the host microorganism. In some embodiments, the genes to be altered in order to render a recombinant-phage reproduction-deficient are chosen so that they are not required for genome replication of the phage. This ensures that the recombinant phage genome is replicated to typical high copy numbers, resulting in high copy numbers of the indicator gene. Early and immediate early genes often fall into the category of genes required for genome replication of the phage. Early and immediate early genes (T7 RNA Polymerase for example) may also be required for expression of the genes controlled by late gene promoters, such as the indicator gene in the recombinant phage. Accordingly, immediate early and early genes, also known as Class I or Class II genes, may not be suitable for alterations. In some embodiments, the genes to be altered in order to render a recombinant-phage reproduction-deficient are chosen because they are required for mature phage virion production. For example, the genes suitable for alterations or deletions may be structurally important genes, such as the genes required for virion assembly. In some embodiments, the genes to be altered in order to render a recombinant-phage reproduction-deficient are chosen that are late genes required for mature phage virion production yet are not expressed in high copy number. In some embodiments, a reproduction-deficient indicator phage may comprise more than one (that is, one or more) altered gene. Some examples of the genes that may be suitable for alteration or deletion in order to render a recombinant phage reproduction deficient are as follows: In bacteriophage T4 and related phages and T4 virus (for example, SEA1, Saka4 and TSP12 phages) and closely related Viulikevirus (for example, CBA120, TSP1 phages), some of the genes that may be suitable for alteration are: gp4 encoding head completion protein; gp20 encoding portal vertex protein; gp21 encoding prohead core scaffold protein and protease; gp22 encoding prohead scaffold protein; gp25 encoding baseplate wedge subunit; gp26 encoding baseplate hub subunit; gp53 encoding baseplate wedge component; gp54 encoding. baseplate-tail tube initiator. In podavirus (T7, MP87 phages), some of the genes that may be suitable for alteration are: gp6.7 encoding virion protein; gp7.3 encoding tail protein; gp8 encoding head-tail connector protein; gp9 encoding scaffolding protein; gp13. In siphovirus (T5, P70-related phages), some of the genes that may be suitable for alteration are: Gp150 encoding prohead protease and gp152 encoding portal protein. It is to be understood that the above list is non-limiting and other genes may be altered in a variety of phages.

In some embodiments, the reproduction-deficient indicator phages according to the embodiments of the present invention comprise a mutation in a suitable gene. Such mutations may be amber mutations, ochre mutations, base substitutions, deletions or insertions, or any combinations of the above-types of mutations. The mutations or their combinations may render the gene chosen for alteration dysfunctional by altering the encoded protein structure, suppress transcription or expression (for example, by a change in promotor) of the gene being altered, cause premature termination of transcription or expression, etc. In some other embodiments, in the reproduction-deficient indicator phages a suitable gene is altered by replacing at least a part of a suitable gene by an indicator gene. As a result, the recombinant phage becomes reproduction-deficient and incorporates an indicator gene sequence. In some embodiments, it may be preferable to replace at least a part of a suitable gene in a phage by an indicator gene, rather than introduce one or more mutations into a suitable gene, in order to avoid reversion or suppression of the one or more mutations in the suitable gene and return of the recombinant phage to reproduction competency.

In some embodiments, a reproduction-deficient indicator bacteriophage can be derived from podaviruses such as T7, T7-like, myoviruses such as T4, T4-like, ViI, ViI-like (or Vi1 virus, per GenBank/NCBI), *Cronobacter* spp, -specific bacteriophage, such as Saka2 or Saka4, *Salmonella* phage SPN1S, *Salmonella* phage 10, *Salmonella* phage epsilon 15, *Salmonella* phage SEA1, *Salmonella* phage Spn1s, *Salmonella* phage P22, *Salmonella* phage TSP1, *Salmonella* phage TSP11, *Listeria* phage LipZ5, *Listeria* phage P40, *Listeria* phage vB_LmoM_AG20, *Listeria* phage P70, *Listeria* phage A511, *Listeria* phage LMA4, *Listeria* phage LMA8, *Listeria* phage LPES1, *Listeria* phage LPJP1, *Staphylococcus* phage P4 W, *Staphylococcus* phage K, *Staphylococcus* phage Twort, *Staphylococcus* phage SA97, *Staphylococcus* phage ISP, *Escherichia coli* O157:H7 phage CBA120, or another wild-type or engineered bacteriophage. In some embodiments, an indicator bacteriophage is derived from a bacteriophage with a genome with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% homology to can be derived from podoviruses such as T7, T7-like, myoviruses such as T4, T4-like, ViI, ViI-like (or Vi1 virus, per GenBank/NCBI), *Cronobacter* spp, -specific bacteriophage, such as Saka2 or Saka4, *Salmonella* phage SPN1S, *Salmonella* phage 10, *Salmonella* phage epsilon 15, *Salmonella* phage SEA1, *Salmonella* phage Spn1s, *Salmonella* phage P22, *Listeria* phage LipZ5, *Listeria* phage P40, *Listeria* phage vB_LmoM_AG20, *Listeria* phage P70, *Listeria* phage A511, *Staphylococcus* phage P4 W, *Staphylococcus* phage K, *Staphylococcus* phage Twort, *Staphylococcus* phage SA97, *Escherichia coli* O157:H7 phage CBA120, or another wild-type or engineered bacteriophage In some embodiments, a reproduction-deficient indicator phage is derived from a phage that is highly specific for a particular microorganism. For example, a reproduction-deficient indicator bacteriophage may be prepared from an environmentally derived bacteriophage specific for bacteria found in certain environments.

A selection of an indicator gene to be inserted into a reproduction-deficient indicator phage may be guided by a variety of considerations. For example, most phages can package DNA that is a few percent larger than their natural genome. With this consideration, a smaller indicator gene may be a more appropriate choice for modifying a bacteriophage, especially one with a smaller genome. OpLuc and NANOLUC® proteins are only about 20 kDa (approximately 500-600 bp to encode), while FLuc is about 62 kDa (approximately 1,700 bp to encode). For comparison, the genome of T7 is around 40 kbp, while the T4 genome is about 170 kbp. Moreover, the reporter gene should not be expressed endogenously by the bacteria (that is, is not part of the bacterial genome), should generate a high signal to background ratio, and should be readily detectable in a timely manner. NANOLUC® by PROMEGA® is a modified *Oplophorus gracihrostris* (deep sea shrimp) luciferase. In some embodiments, NANOLUC® combined with Nano-Glo (also by PROMEGA®), an imidazopyrazinone substrate (furimazine), can provide a robust signal with low background. In some embodiments, more than one indicator gene may be inserted into a reproduction-deficient phage. For example, more than one copy (such as two copies) of the same indicator gene may be inserted, which may improve signal intensity and/or signal-to-noise ratio of an assay using a reproduction-deficient indicator phage. In another example, different indicator genes, such as two different indicator genes, may be inserted, which may allow for bimodal signal detection. For instance, NANOLUC® gene may be inserted along with a gene encoding a green fluorescent protein (GFP), or NANOLUC® gene may be inserted along with a gene encoding a different luciferase, such as firefly luciferase.

An indicator gene may encode a variety of biomolecules or, in itself, may be a detectable biomolecule. For example, an indicator gene may encode a detectable polypeptide or protein. In another example, an indicator gene may be a gene that expresses a detectable product or an enzyme that produces a detectable product. In one more example, an indicator gene may encode a detectable nucleic acid or include a detectable nucleic acid. For instance, an indicator gene may encode a detectable aptameric, such us RNA Mango, or an indictor gene may contain a nucleic acid sequence detectable with real-time polymerase chain reaction (RT-PCR). In some embodiments, a product of the indicator gene can be a detectable enzyme. The indicator gene product may generate light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. For example, in some embodiments the indicator gene encodes a luciferase enzyme. Various types of luciferase may be used. The luciferase can be one of *Oplophorus* luciferase, Firefly luciferase, Lucia luciferase, *Renilla* luciferase, or an engineered luciferase. In some embodiments, Firefly luciferase is the indicator moiety. In some embodiments, the luciferase gene is derived from *Oplophorus*. In some embodiments, the indicator gene is a genetically modified luciferase gene, such as NANOLUC®. Other engineered luciferases or other enzymes that generate detectable signals may also be appropriate indicator moieties.

Genetic modifications to reproduction-deficient indicator bacteriophage may include insertions, deletions, or substitutions of a small fragment of nucleic acid, a substantial part of a gene, or an entire gene. In some embodiments, inserted or substituted nucleic acids comprise non-native sequences. For example, a non-native indicator gene may be inserted into a bacteriophage genome such that it is under the control of a bacteriophage promoter. A non-native indicator gene may be inserted so that it replaces at least a part of a sequence of a late phage gene, and the insertion of the indicator gene renders the resulting recombinant phage reproduction-deficient. Including stop codons in all three reading frames of an indicator gene may help to increase expression by reducing read-through, also known as leaky expression. This strategy may also eliminate the possibility of a fusion protein being made at low levels, which would manifest as background signal that cannot be separated from the phage. Thus, in some embodiments, the non-native indicator gene is not part of a fusion protein. That is, in some embodiments, a genetic modification may be configured such that the indicator protein product does not comprise polypeptides of the phage. In some embodiments, the present invention comprises a genetically modified reproduction-deficient indicator bacteriophage comprising a non-bacteriophage indicator gene in the late (class III) gene region. In some embodiments, the non-native indicator gene is under the control of a late promoter. Using a viral late gene promoter insures the reporter gene (for example, luciferase) is not only expressed at high levels, like viral capsid proteins, but also does not shut down as similar endogenous bacterial genes or early bacteriophage genes. In some embodiments, the late promoter is a T4-, T7-, or ViI-like promoter, or another phage promoter similar to that found in wild-type phages.

In some embodiments, expression of the indicator gene of the reproduction-deficient indicator phage in a microorganism of interest, following infection with the reproduction-deficient indicator phage, results in production of soluble protein product. In some embodiments, the non-native indicator gene is not contiguous with a gene encoding a structural phage protein and therefore does not yield a fusion protein. Unlike systems that employ a fusion of a detection moiety to the capsid protein (a fusion protein), some embodiments of the present invention express a soluble indicator or reporter (for example, soluble luciferase). In some embodiments, the indicator or reporter is ideally free of the phage structure. That is, the indicator or reporter is not attached to the phage structure. As such, the gene for the indicator or reporter is not fused with other genes in the genome of the reproduction-deficient indicator phage. This may greatly increase the sensitivity of the detection assays in which reproduction-deficient indicator phages according to the embodiments of the present invention are used (the sensitivity may be increased down to detecting a single microorganism in a sample), and simplify the assays, allowing the assays to be completed in two hours or less for some embodiments, as opposed to several hours due to additional purification steps required with constructs that produce detectable fusion proteins. Further, fusion proteins may be less active than soluble proteins due, for example, to protein folding constraints that may alter the conformation of the enzyme active site or access to the substrate. If the concentration is 10 bacterial cells/mL of sample, for example, less than two hours may be sufficient for the assay.

Moreover, fusion proteins by definition limit the number of the moieties attached to subunits of a protein in the bacteriophage. For example, using a commercially available system designed to serve as a platform for a fusion protein would result in about 415 copies of the fusion moiety, corresponding to the about 415 copies of the gene 10B capsid protein in each T7 bacteriophage particle. Without this constraint, infected bacteria can be expected to express many more copies of the detection moiety (for example, luciferase) than can fit on the bacteriophage.

In some embodiments of recombinant reproduction-deficient indicator phages, a late promoter (such as a class III promoter, for example, from T7, T4, ViI or Saka) is used for transcription of an indicator gene. Such later promoter has high affinity for RNA polymerase of the same phage that transcribes genes for structural proteins assembled into the phage particle. These proteins are the most abundant proteins made by the phage, as each phage particle comprises dozens or hundreds of copies of these molecules. The use of a viral late promoter can ensure optimally high level of expression of the indicator gene product, such as luciferase. The use of a late viral promoter derived from, specific to, or active under the original wild-type bacteriophage the reproduction-deficient indicator phage is derived from (for example, a T4, T7, ViI, or Saka late promoter with a T4-, T7-, ViI-, or Saka-based system) can further ensure optimal expression of the detection moiety. The use of a standard bacterial (non-viral/non-bacteriophage) promoter may in some cases be detrimental to expression, as these promoters are often down-regulated during bacteriophage infection (in order for the bacteriophage to prioritize the bacterial resources for phage protein production). Thus, in some embodiments, the reproduction-deficient indicator phage is preferably engineered to encode and express at high level a soluble (free) indicator moiety, using a placement in the genome that does not limit expression to the number of subunits of a phage structural component.

In some embodiments, reproduction-deficient indicator phages are designed to optimize desirable traits for use in assays for detection of microorganisms of interest. In some embodiments, bioinformatics and previous analyses of genetic modifications are employed to optimize desirable traits. For example, in some embodiments, the genes encoding phage tail proteins can be optimized to recognize and bind to particular species of bacteria. In other embodiments the genes encoding phage tail proteins can be optimized to recognize and bind to an entire genus of bacteria, or a particular group of species within a genus. In this way, the phage can be optimized to detect broader or narrower groups of pathogens. In some embodiments, the reproduction-deficient indicator phages may be designed to improve expression of the reporter gene. Additionally and/or alternatively, in some instances, the reproduction-deficient indicator phages may be designed to increase the burst size of the phage to improve detection. Designing the reproduction-deficient indicator phages designed to produce increased copy number of phage genomes upon infection or to increase the expression level of the late genes would lead to an increased burst size.

In some embodiments, the stability of the reproduction-deficient indicator phage may be optimized to improve shelf-life. For example, enzybiotic solubility may be increased in order to increase subsequent phage stability. Additionally and/or alternatively thermostability of the reproduction-deficient indicator phage may be optimized. Thermostable phages better preserve functional activity during storage thereby increasing shelf-life. Thus, in some embodiments, the thermostability and/or pH tolerance may be optimized.

Compositions of the invention may comprise one or more reproduction-deficient indicator bacteriophages and one or more indicator genes. In some embodiments, compositions can include cocktails of different reproduction-deficient indicator phages specific for different microorganisms of interest. Such cocktails can be used for simultaneous detection of multiple microorganisms of interest. In some embodiments, compositions can include cocktails of different reproduction-deficient indicator phages that may encode and express same or different indicator proteins. In some embodiments, the cocktail of reproduction-deficient bacteriophage comprises at least two different types of reproduction-deficient indicator bacteriophages.

Methods of Preparing (Making) Reproduction-Deficient Indicator Bacteriophage

Embodiments of methods for making reproduction-deficient indicator phage according to may begin with selection of a parent phage for genetic modification. For example, some bacteriophages are highly specific for a target microorganism, which may include specificity for a particular strain or serotype of a target microorganism. This presents an opportunity for highly specific detection. Parent phage may be a wild-type phage found in any environment or an engineered phage. The methods according to the embodiments of the present invention utilize the high specificity of binding associated with bacteriophages, which recognize and bind to a particular microorganism of interest as a means to amplify a signal and thereby detect low levels of a microorganism (down to a single microorganism, in some cases) present in a sample. For example, bacteriophages specifically recognize surface receptors of particular microorganisms and thus specifically infect those microorganisms. As such, they are appropriate for targeting a microorganism of interest. Some embodiments of the invention utilize the specificity of binding and high-level genetic expression capacity of indicator bacteriophages for rapid and sensitive targeting to infect and facilitate detection of a microorganism of interest of interest. Accordingly, some embodiments of methods for preparing a recombinant reproduction-deficient indicator phage may include steps related to selecting a parent phage that specifically infects a target microorganism of interest.

Some embodiments of methods for preparing a recombinant reproduction-deficient indicator phage include a step or steps of altering a gene of the parent page to generate a recombinant reproduction-deficient phage. For example, some embodiments may include step of steps of introducing one or more mutations into a suitable gene in order to render the parent phage reproduction-deficient. Such suitable genes and mutations are described elsewhere in this document.

Some embodiments of methods for preparing a recombinant reproduction-deficient indicator phage include a step of altering a gene of the parent page to generate a recombinant reproduction-deficient phage. For reproduction, a reproduction-deficient page requires an engineered strain of the phage's host microorganism (such as a bacterium) capable of expressing a product of the gene altered to render the phage reproduction-deficient. Such engineered strain may be termed "permissive." Accordingly, some embodiments of methods for preparing a recombinant reproduction-deficient indicator phage may include a step of generating such a permissive engineered strain of the host microorganism. Some embodiments of methods for preparing a recombinant reproduction-deficient indicator phage may include a step of infecting a permissive engineered strain of the host microorganism with a reproduction-deficient indicator phage. Some embodiments of methods for preparing a recombinant reproduction-deficient indicator phage may include a step of preparing a homologous recombination plasmid/vector that comprises an indicator gene. Some embodiments of methods for preparing a recombinant reproduction-deficient indicator phage may include a step of transforming the homologous recombination plasmid/vector into a permissive engineered host microorganism infected with the reproduction-deficient indicator phage. Some other embodiments of methods for preparing a recombinant reproduction-deficient indicator phage may include a step of transforming the homologous recombination plasmid/vector into a permissive engineered host microorganism, followed by a step of infecting the transformed permissive engineered host microorganism with the reproduction-deficient indicator phage. In some embodiments, infection of the permissive engineered host microorganism and transformation of the homologous recombination plasmid/vector into the permissive engineered host microorganism may be accomplished in the same step. In other embodiments, infection of the permissive engineered host microorganism and transformation of the homologous recombination plasmid/vector into the permissive engineered host microorganism is accomplished in two steps or more than two steps. Once the permissive engineered host microorganism houses a reproduction-deficient phage and the homologous recombination plasmid/vector, a homologous recombination occurs between the plasmid/vector and the phage genome. A recombinant recombinant-deficient phage including an indicator gene (a reproduction deficient indicator phage) may then be isolated.

In some embodiments, a gene of the parent page that is altered to render the phage reproduction-deficient may be altered by a replacement of at least a part of the parent phage by the indicator gene. Accordingly, some embodiments of methods for preparing a recombinant reproduction-deficient indicator phage include a step of preparing a homologous recombination plasmid/vector that comprises an indicator gene flanked by sequences of a gene targeted for deletion in the parent phage in order to render it reproduction-deficient. The homologous recombination plasmid/vector may be then transformed into a permissive engineered host microorganism infected with the parent phage, thereby allowing homologous recombination to occur between the plasmid/vector and the parent phage genome Some other embodiments of methods for preparing a recombinant reproduction-deficient indicator phage may include a step of transforming the homologous recombination plasmid/vector into a permissive engineered host microorganism, followed by a step of infecting the transformed permissive engineered host organism with the reproduction-deficient indicator phage, thereby allowing homologous recombination to occur between the plasmid/vector and the parent phage genome. In some embodiments, infection of the permissive engineered host microorganism and transformation of the homologous recombination plasmid/vector into the permissive engineered host organism may be accomplished in the same step, thereby allowing homologous recombination to occur between the plasmid/vector and the parent phage genome. A recombinant recombinant-deficient phage including an indicator gene (a reproduction deficient indicator phage) may then be isolated.

In some embodiments of methods for preparing a recombinant reproduction-deficient indicator phage, the introduction of the reproduction-deficiency and of the indicator gene into the parent phage is accomplished in a one-step recombination process. A recombination strategy for such a process is illustrated in FIG. 1. An advantage of embodiments such as this is simplification of the process for generating the reproduction-deficient indicator phage. Another advantage of such embodiments is that they allow for the reporter gene to be used to both detect and isolate the reproduction-deficient indicator phage. If a genetic alteration is introduced to confer reproduction-deficiency in a reproduction-capable phage include an indicator gene (a reproduction-capable indicator phage), then the phages with both with and without reproduction-deficiency alteration would grow, making the screening for the indicator phages more laborious.

Figure 3:
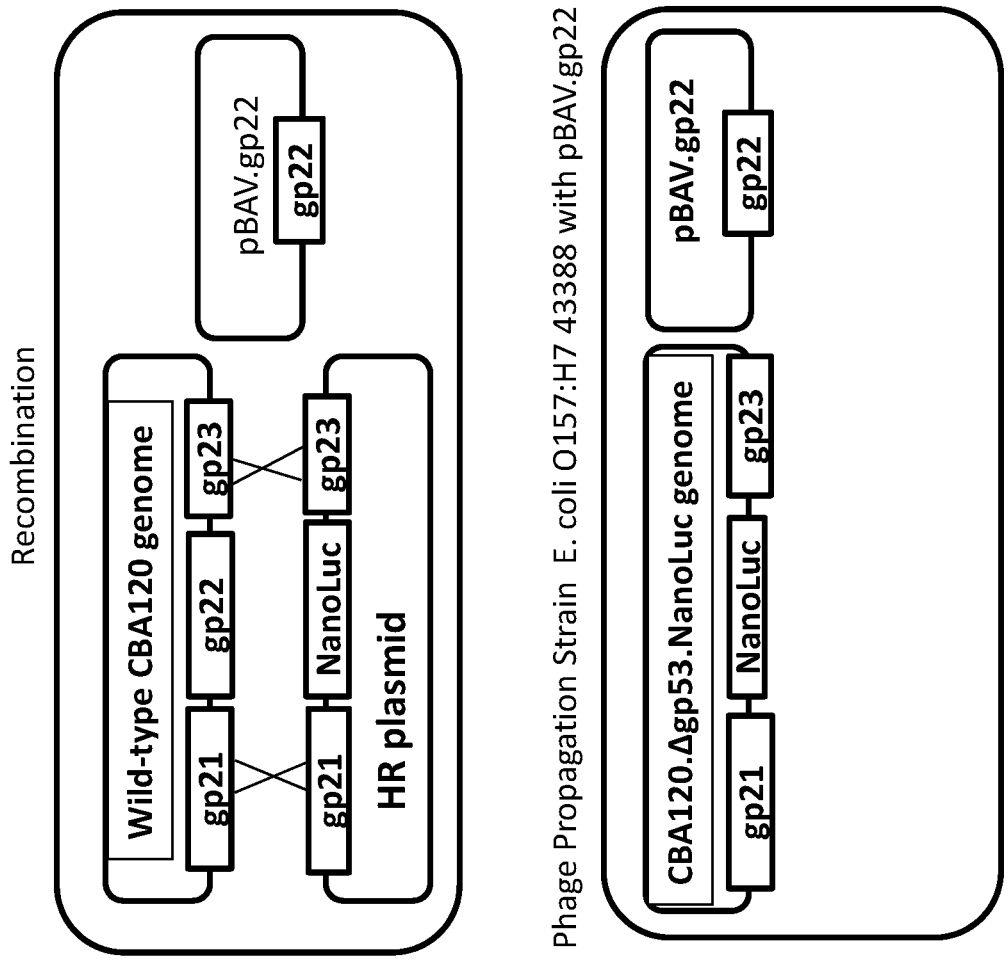
FIG. 3 schematically illustrates homologous recombination with co-infection trans complementation of a CBA120 *E. coli*-specific phage to produce a reproduction-deficient indicator phage CBA120.Δgp22.NanoLuc.

FIG. 3 schematically illustrates a homologous recombination process that occurs between the homologous recombination (HR) plasmid in a parent phase genome in a host microorganism, which leads to generation of an indicator phage according to one of the embodiments of the present invention. In the illustrated homologous recombination process, the phage is CBA120 E. coli phage, and the reporter gene is NANOLUC® reporter gene. Accordingly, the host microorganism is E. coli in the illustrated embodiment. It is to be understood that FIG. 3 is intended to be exemplary and non-limiting, and that other phages, corresponding host organisms and reporter genes may be used. In some embodiments, it may be preferred to utilize phages that have been isolated from the environment for production of the reproduction-deficient indicator phages. In this way, reproduction-deficient indicator phages that are specific to naturally derived microorganisms may be generated.

Various methods for designing and preparing a homologous recombination plasmid are known. Various methods for transforming bacteria with a plasmid are known, including heat-shock, F pilus mediated bacterial conjugation, electroporation, and other methods. Various methods for isolating a particular clone following homologous recombination are also known. Some method embodiments described herein utilize particular strategies.

Some embodiments of methods for preparing reproduction-deficient indicator bacteriophage may include the steps of selecting a parent phage that specifically infects a target microorganism of interest; determining the natural sequence in the late region of the genome of the selected parent phage; annotating the genome and identifying the a suitable late gene of the selected parent phage, wherein the alteration of the suitable late gene is intended to render the parent phage reproduction-deficient; designing a sequence for homologous recombination adjacent to the major late gene and comprising a codon-optimized reporter gene; incorporating the sequence designed for homologous recombination into a plasmid/vector; transforming the plasmid/vector into a target microorganism comprising a plasmid encoding a functional suitable late gene; selecting for the transformed target microorganism; infecting the transformed microorganism with the selected parent phage, thereby allowing homologous recombination to occur between the plasmid and the phage genome; determining the titer of the resulting recombinant phage lysate; and performing a limiting dilution assay to enrich and isolate the recombinant phage. Enrichment of the reproduction-deficient recombinant phage fraction over the parental phage fraction may be performed in whole or in part in permissive target cells, which contain the trans plasmid. Some embodiments comprise further repeating the limiting dilution and titer steps, following the first limiting dilution assay, as needed until the recombinant phage represent a detectable fraction of the mixture. For example, in some embodiments the limiting dilution and titer steps can be repeated until at least 1/30 of the phage in the mixture are recombinant before isolating a particular clone of recombinant phage. A ratio of 1:30 recombinant:parent is expected, in some embodiments, to yield an average of 3.2 transducing units (TU) per 96 plaques (for example, in a 96-well plate). The initial ratio of recombinant to parent phage may be determined by performing limiting dilution assays based on the TCID50 (tissue culture infectious dose 50%) as previously described in U.S. application Ser. No. 15/409,258. By Poisson distribution, a 1:30 ratio generates a 96% chance of observing at least one TU somewhere in the 96 wells.

Some embodiments include designing (and optionally preparing) a sequence for homologous recombination need to insert an indicator gene. In some embodiments, the homologous recombination sequences are designed to replace a late gene in order to render the parent phage reproduction-deficient. In some embodiments, the sequence of the indicator gene comprises a codon-optimized reporter gene preceded by an untranslated region. The untranslated region may include a phage late gene promoter and ribosomal entry site. In some embodiments, the inserted genetic construct further comprises its own exogenous, dedicated promoter to drive expression of the indicator gene. The exogenous promoter is in addition to any endogenous promoter in the phage genome. As phages produce polycistronic mRNA transcripts, only a single promoter is required upstream of the first gene/cistron in the transcript. Conventional recombinant constructs only use the endogenous phage promoter to drive inserted genes. Addition of an additional promoter upstream of the reporter gene and ribosomal binding site may increase gene expression by acting as a secondary initiation site for transcription.

There are numerous known methods and commercial products for preparing plasmids. For example, PCR, site-directed mutagenesis, restriction digestion, ligation, cloning, and other techniques may be used in combination to prepare plasmids. Synthetic plasmids can also be ordered commercially (for example, GeneWiz). Cosmids can also be employed, or the CRISPR/CAS9 system could be used to edit a bacteriophage genome selectively. Some embodiments of methods of preparing an indicator bacteriophage include designing a plasmid that can readily recombine with a starting bacteriophage genome to generate recombinant genomes. In designing a plasmid, some embodiments include addition of a codon-optimized reporter gene, such as a luciferase gene. Some embodiments further include addition of elements into the upstream untranslated region. For example, an upstream untranslated region can be added before the sequence encoding the start codon of the NANO-LUC® reporter gene. The untranslated region can include a promoter, such as a T4, T4-like, T7, T7-like, ViI, or ViI-like promoter. The untranslated region can also include a Ribosomal Entry/Binding Site (RBS), also known as a "Shine-Dalgarno Sequence" with bacterial systems. Either or both of these elements, or other untranslated elements, can be embedded within a short upstream untranslated region made of random sequences comprising about the same GC content as rest of the phage genome. The random region should not include an ATG sequence, as that will act as a start codon.

Figure 2:
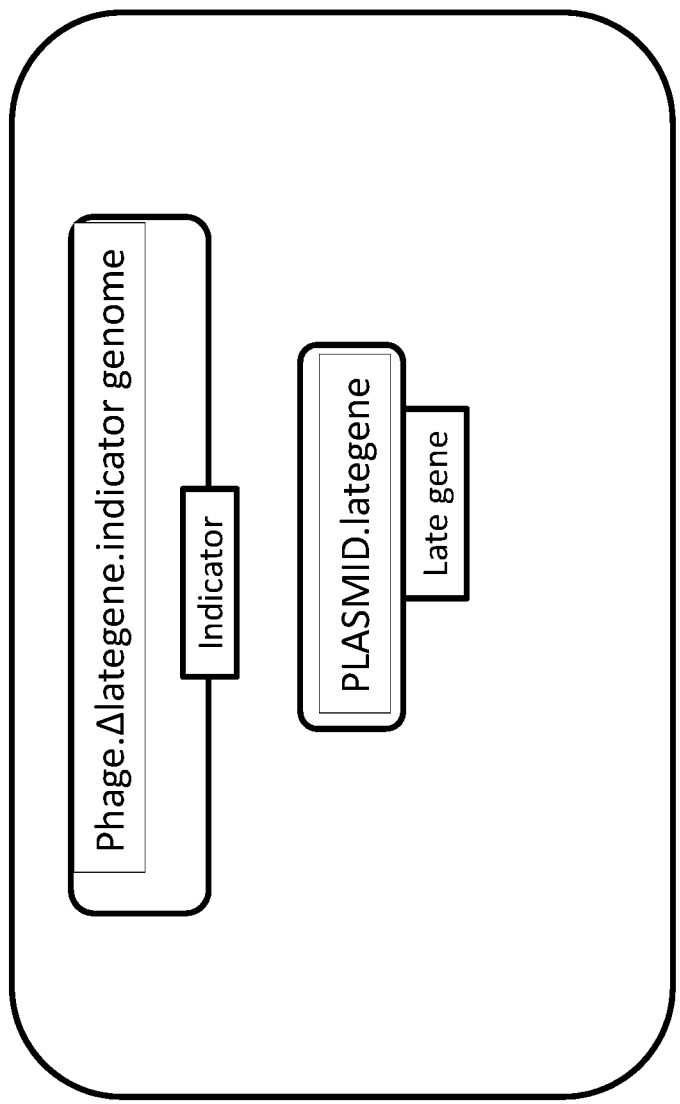
FIG. 2 schematically illustrates a "permissive" microorganism transformed with the plasmid expressing the gene required for phage reproduction and infected with a reproduction-deficient indicator phage.

As discussed elsewhere in this document, isolation and propagation of recombinant reproduction-deficient indicator phages according to the embodiments of the present invention can only be performed in "permissive" host microorganisms expressing the gene or genes that were altered to render the reproduction-deficient indicator phage reproduction-deficient. Such "permissive" microorganisms, for example, bacteria, may be engineered by transforming them with a plasmid expressing the gene required for phage reproduction. FIG. 2 illustrates a cell of such a "permissive" microorganism transformed with the plasmid expressing the gene required for phage reproduction and also infected with a reproduction-deficient indicator phage. The plasmid containing the gene required for phage reproduction is chosen to be compatible with the homologous recombination plasmid used for insertion of an indicator gene into the phage genome. For example, the plasmid expressing the gene required for phage reproduction and the homologous recombination plasmid may be chosen so that they contain different antibiotic resistance marker, so that both plasmids may be maintained simultaneously in a host organism. In another example, the plasmid expressing the gene required for phage reproduction and the homologous recombination plasmid are chosen to contain compatible origins of replication, so as not to interfere with each other. Examples of compatible plasmids are pUC derived plasmids using the ori origin of replication and pBAV1k-T5-GFP plasmids using the RCR (rolling circle replication) origin of replication. Since reproduction-deficient phages require an engineered "permissive" strain of a host microorganism in order to reproduce, some embodiments of methods for preparing a recombinant reproduction-deficient indicator phage include a step or steps of generating an engineered strain of the target microorganism capable of expressing a product of the gene altered in the reproduction-deficient phage in order to render it reproduction-deficient. In some embodiments, generating of the engineered strain of the target microorganism involves transforming the target microorganism with a plasmid encoding and capable of expressing the gene or genes altered in the recombinant reproduction-deficient phage. Alternatively, the required gene may be integrated into target microorganism genome by various other methods, such as via transposon, homologous recombination, site-specific recombination/integration, or others.

Figure 27:
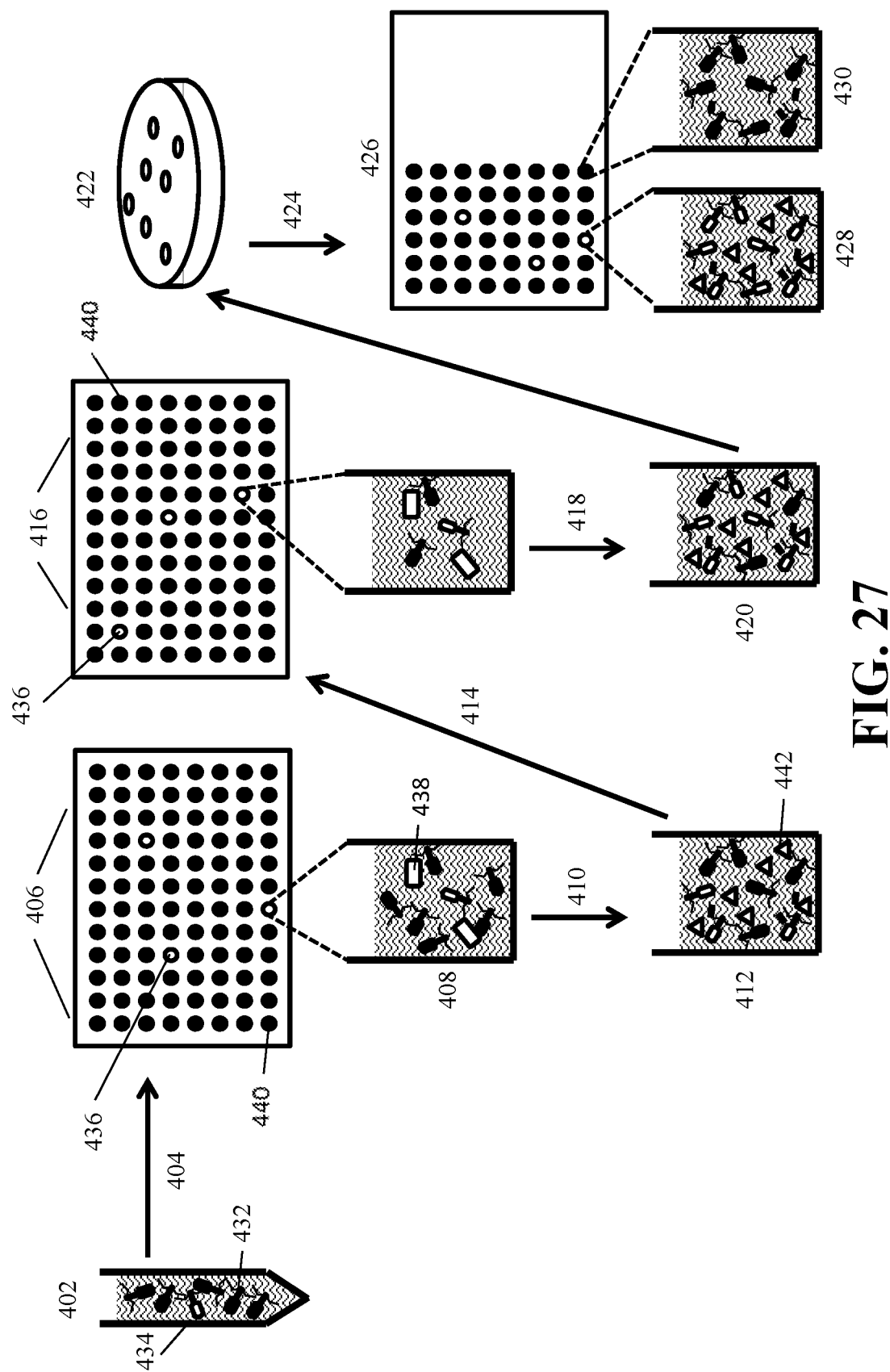
FIG. 27 depicts the isolation of recombinant reproduction-deficient indicator phage using a series of sequential infection and dilution steps to identify reproduction-deficient indicator phage.

FIG. 27 schematically illustrates an example of a process of isolation of reproduction-deficient recombinant phage from the mixture of parent phage and reproduction-deficient indicator phage resulting from the homologous recombination. In the first step 402, permissive host microorganisms transformed with the homologous recombination plasmid and plasmid expressing the required phage gene are infected with the parent phage, resulting in progeny phage with a mixture of parental and reproduction-deficient recombinant indicator phage with very low ratios of parent to reproduction-deficient indicator phage 434. The resulting phage mix is diluted 404 into 96-well plates 406 to give an average of 5 recombinant transducing units (TU) per plate (9.3 PFU/well). The 96-well plate is then assayed, as described below, for reporter gene activity to identify wells 436 containing reproduction-deficient indicator phage as compared to wells 440 containing parent phage. Permissive host microorganisms containing the plasmid expressing the required phage gene 438 are added to each well (408); for example, each well may contain about 50 µL of a turbid bacterial culture, when the host microorganism is a bacterium. This allows the reproduction-deficient indicator phage to replicate and produce the soluble reporter gene product 442. After incubation step 410 (for example, 5 hours of incubation at 37° C.), wells may be screened for the presence of the reporter gene product 442. Any positive wells are likely to have been inoculated with a single reproduction-deficient indicator phage, and at this stage the mixture may contain a ratio of approximately 10 parent phage:1 recombinant, an enrichment over the original ratio. If necessary (for example, if the ratio of recombinant:total is lower than 1:30), progeny from this enriched culture 412 may be subjected to additional limiting dilution assay(s) 414 to increase the ratio and determine the actual concentration of recombinant reproduction-deficient indicator phage transducing units. For example, if the ratio was 1:384 recombinants:PFU (with PFU determined by plaque assay performed on permissive bacteria), about 5 recombinant TU along with 1920 contaminating total phage (5×384=1920) per 96-well plate 416 may be aliquoted 414 from the previous positive well, leading to an approximate inoculation of 20 mostly parent phage per well (1920 PFU/96 wells=20 PFU/well) of a second dilution assay plate 420. Any positive luciferase wells are likely to have been inoculated with a single recombinant reproduction-deficient indicator phage along with 19 parent phage. These wells may be analyzed for presence of luciferase 442.

After addition of host microorganism and incubation 418, soluble reporter gene product and phage are present at approximately 20; 1 420. This ratio may be verified by TU50 titration for recombinants, a limiting dilution assay based on the Tissue Culture Infectious Dose 50 (TCID50) assay scoring for reporter gene product activity instead of cell killing, and plaque assay for total PFU. Finally, a plaque assay may be performed 422 to screen for recombinants that express reporter gene product 446. A small number of individual (for example, n=48) plaques may be individually picked and screened in a third multiwell plate 426 for luciferase activity 436. In some embodiments, this approach should insure that enough plaques be screened so about three indicator bacteriophages are in the mix of plaques being screened based on the known ratio of recombinants to total phage. One plaque may be removed from the plate to each well of a 96-well plate 424 and a reporter gene product assay performed 426 to determine which wells contained phage exhibiting reporter gene product activity 442. Wells 428 demonstrating such activity represent pure recombinant reproduction-deficient indicator phage 434, while wells without such activity 430 represent pure parent phage 432. Individual plaques may then be suspended in buffer (for example, 100 µL of buffer) or media, and an aliquot (for example, about 5 µL) added to a well containing a host microorganism culture, and assayed after incubation (for example, about 45 minutes to 1 hour at 37° C.). Positive wells are expected to contain a pure culture of reproduction-deficient indicator phage. Certain embodiments can include additional rounds of plaque purification. Thus, as illustrated by FIG. 27, reproduction-deficient indicator phage generated by homologous recombination of a plasmid designed for recombination with the parent phage genome can be isolated from a mixture comprising a very small percentage (for example, 0.005%) of indicator bacteriophage.

Following isolation, large scale production may be performed to obtain high titer reproduction-deficient indicator phage stocks appropriate for use in detection methods according to the embodiments of the present invention. Production and preparation of reproduction-deficient indicator phage stocks may include purification of the reproduction-deficient indicator bacteriophage from any free detection moiety produced during the production of reproduction-deficient indicator bacteriophage in bacterial culture. Standard phage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). As a result of the purification procedure, reproduction-deficient indicator phage stock may be substantially free of any reporter product gene generated during production. Removal of residual indicator gene product present in the reproduction-deficient indicator phage stock can substantially reduce background signal observed when the reproduction-deficient indicator phage are used for detecting microorganisms of interest in a sample.

Methods of Using Reproduction-Deficient Indicator Phages for Detecting Microorganisms As noted herein, in certain embodiments, the invention may comprise methods of using reproduction-deficient indicator phages for detecting microorganisms. The methods of using reproduction-deficient indicator phages for detecting microorganisms according to the embodiments of the invention may be embodied in a variety of ways.

In one embodiment, the invention may include a method for detecting a microorganism of interest in a sample, comprising the steps of: incubating the sample with a reproduction-deficient indicator phage that infects the microorganism of interest, wherein the reproduction-deficient indicator phage comprises an indicator gene, such that expression of the indicator gene following infection of the microorganism of interest results in production of an indicator gene product; and detecting the indicator gene product, wherein positive detection (that is, the detection of presence, amount, or level of the indicator gene product) indicates that the microorganism of interest is present in the sample. In one more embodiment, the invention may include a method for detecting a microorganism of interest in a sample, comprising the steps of: incubating the sample with a reproduction-deficient indicator phage that infects the microorganism of interest, wherein the reproduction-deficient indicator phage comprises an indicator gene, such that expression of the indicator gene following infection of the microorganism of interest results in production of a soluble indicator gene product; and detecting the soluble indicator gene product, wherein positive detection (that is, the detection of presence, amount, or level of the soluble indicator gene product) indicates that the microorganism of interest is present in the sample. In one more embodiment, the invention may include a method for detecting a microorganism of interest in a sample, comprising the steps of: incubating the sample with a reproduction-deficient indicator phage that infects the microorganism of interest, wherein the reproduction-deficient indicator phage comprises an indicator gene, such that expression of the indicator gene following infection of the microorganism of interest results in production of a soluble indicator gene product; and detecting the soluble indicator gene product, wherein positive detection (that is, the detection of presence, amount, or level of the soluble indicator gene product protein) indicates that the microorganism of interest is present in the sample. In variations of the above embodiments, the microorganism of interest may be a bacterium of interest. For example, in an exemplary embodiment, the invention may include a method for detecting a bacterium of interest in a sample comprising the steps of: incubating the sample with a reproduction-deficient indicator phage that infects the bacterium of interest, wherein the reproduction-deficient indicator phage comprises an indicator gene, such that expression of the indicator gene following infection of the bacterium of interest results in production of a soluble indicator gene product; and detecting the indicator gene product, wherein positive detection of the indicator gene product indicates that the bacterium of interest is present in the sample.

In certain embodiments, a method of using reproduction-deficient indicator phage for detecting a microorganism of interest (such method may be referred to as an "assay") may be performed to utilize a general concept that can be modified to accommodate different sample types or sizes and assay formats. Embodiments employing reproduction-deficient indicator bacteriophage of the invention (that is, indicator bacteriophage) may allow rapid detection of specific bacterial strains with total assay times under 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12, 12.5, 13.0, 13.5, 14.0, 14.5, 15.0, 15.5, 16.0, 16.5, 17.0, 17.5, 18.0, 18.5, 19.0, 19.5, 20.0, 21.0, 21.5 22.0, 22.5, 23.0, 23.5, 24.0, 24.5 25.0, 25.5, or 26.0 hours, depending on the sample type, sample size, and assay format. For example, the amount of time required may be somewhat shorter or longer depending on the strain of bacteriophage and the strain of bacteria to be detected in the assay, type and size of the sample to be tested, conditions required for viability of the target, complexity of the physical/chemical environment, and the concentration of "endogenous" non-target bacterial contaminants.

Figure 28:
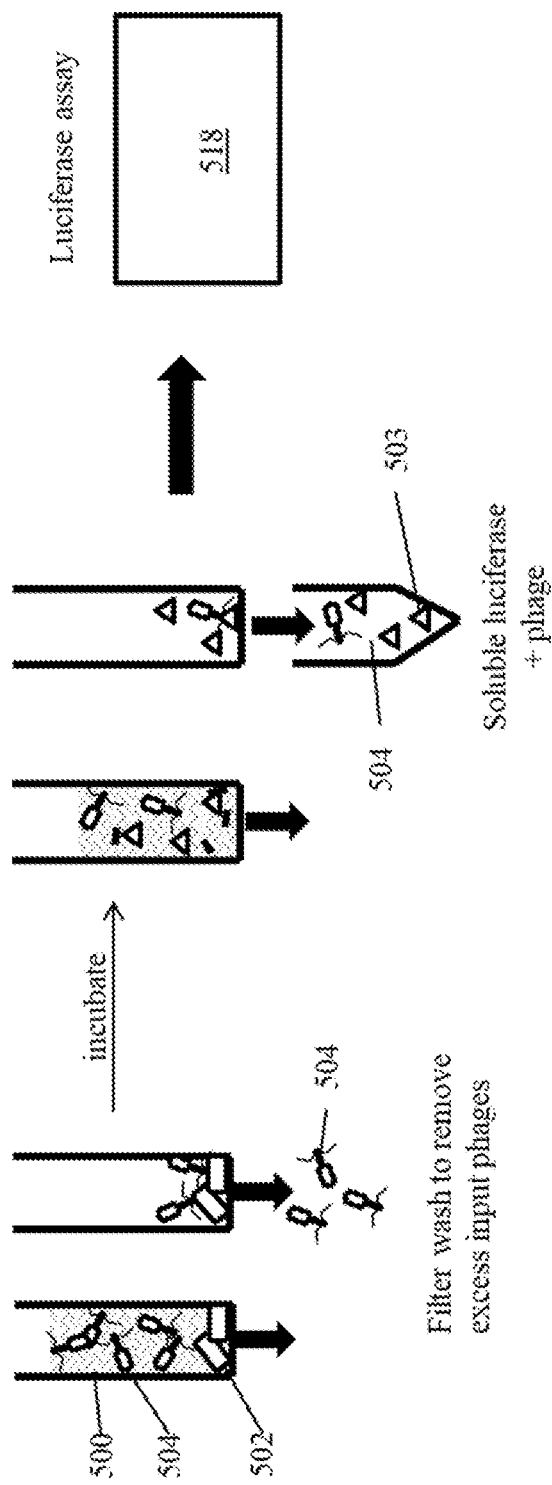
FIG. 28 depicts the use of recombinant reproduction-deficient indicator phage encoding a soluble luciferase to detect a microorganism of interest via detection of luciferase according to an embodiment of the disclosure.

FIG. 28 shows a strategy of using reproduction-deficient indicator phage that produces soluble luciferase according to an embodiment of the invention. In this method, reproduction-deficient indicator phage may be engineered to express a soluble luciferase. Expression of luciferase is driven by a viral capsid promoter (for example, the bacteriophage T7 or T4 late promoter), yielding high expression. In an embodiment illustrated in FIG. 28, at least a part of the sample 500 comprising the microorganism 502 to be detected is placed in a spin column filter and centrifuged to remove excess liquid, and an appropriate multiplicity of reproduction-deficient indicator phage 504 genetically engineered to express soluble luciferase 503 are added. The infected cells may be incubated for a time sufficient for infection to occur (for example, 30-240 minutes at 37° C.). In some embodiments, cell lysis may occur. In other embodiments, cells may not lyse. The reproduction-deficient indicator phage 504 plus free luciferase 503 in the lysate may then be collected, for example, by centrifugation, and the level of luciferase in the filtrate quantified using a luminometer 518. Alternatively, a high throughput method may be employed where the samples are applied to a 96-well filter plate, and after all manipulations listed above are performed, may be directly assayed for luciferase in the original 96-well filter plate without a final centrifugation step. Or other simplified or self-contained formats may be employed, as previously described. Such methods may not require centrifugation or other separation of any components following infection with reproduction-deficient indicator phage. In some embodiments a single device with 2, 3, 4, or more compartments may be used to perform the infection and incubation steps of the assay, followed by detection with an appropriate device, for example detection of luminescence with a handheld luminometer.

Figure 29:
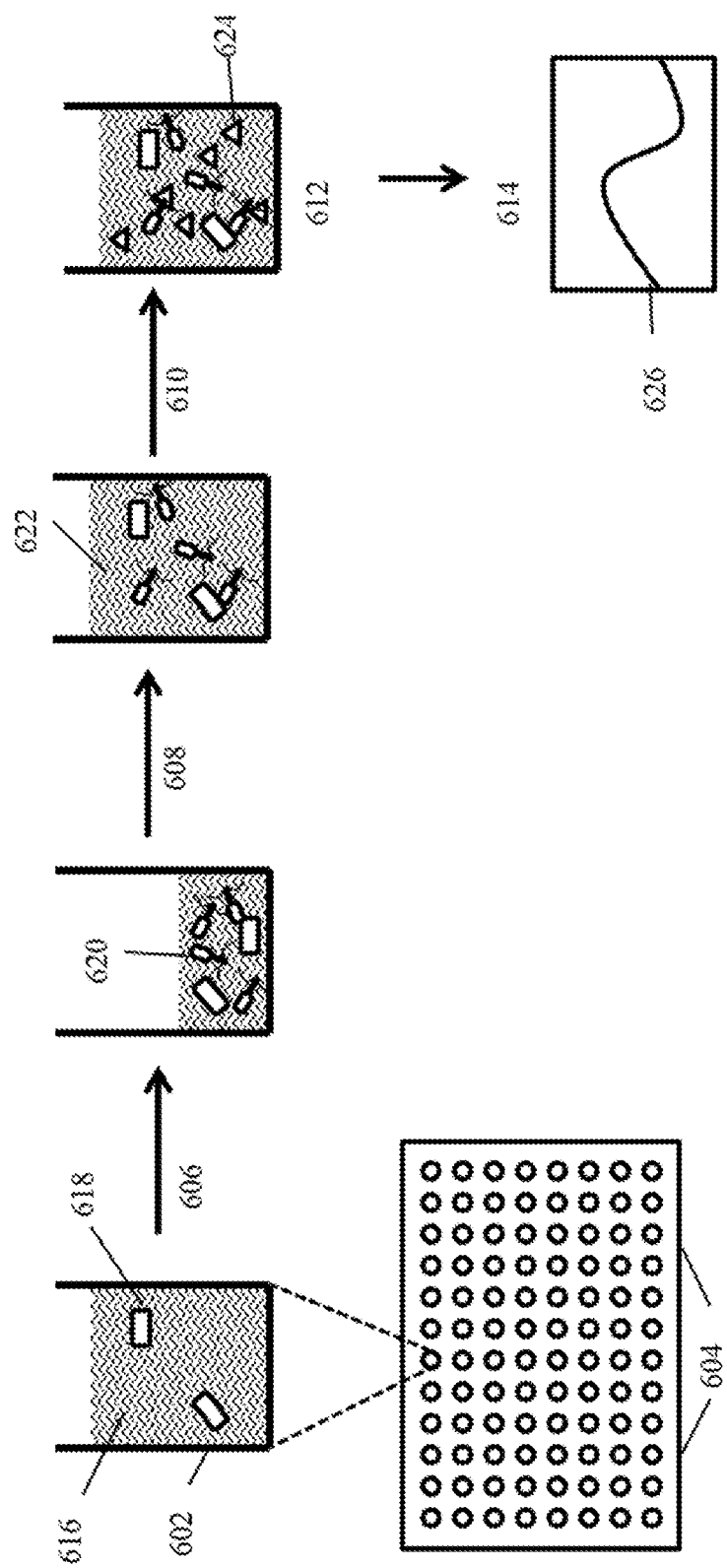
FIG. 29 depicts a filter plate assay for detecting a microorganism of interest using a recombinant reproduction-deficient indicator phage according to an embodiment of the disclosure, in which the microorganism of interest and recombinant reproduction-deficient indicator phage are incubated on filter plates and the indicator protein is detected directly without removal of the incubation medium.

FIG. 29 depicts a filter plate assay for detecting microorganisms of interest using a reproduction-deficient indicator phage according to an embodiment of the invention. Briefly, samples 616 that include a microorganism of interest 618 may be added to wells 602 of a multi-well filter plate 604 and spun 606 to concentrate the samples by removal of liquid from the sample. Reproduction-deficient indicator phage 620 is added to wells and incubated with additional media added for enough time sufficient for adsorption 608 followed by infection of target microorganism of interest and advancement of the phage life cycle 610 (for example, ~45 minutes-2 hours) in order for the reproduction-deficient indicator phage to achieve late gene production, which usually happens late in the infection cycle (but without the production of any mature virus particles by the reproduction-deficient indicator phage). Finally, luciferase substrate is added and reacts with any luciferase present 624. The resulting emission is measured in a luminometer 614 which detects luciferase activity 626.

Figure 30:
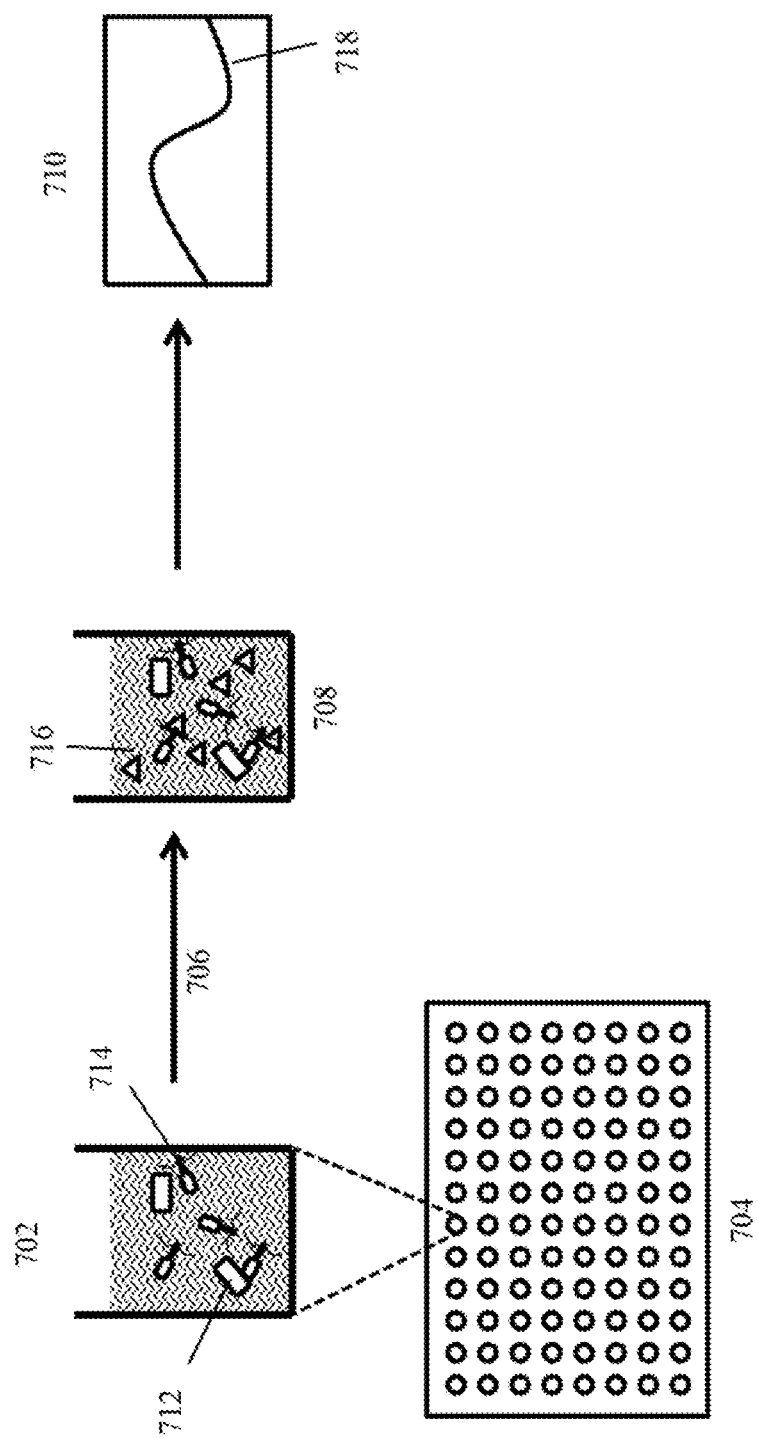
FIG. 30 depicts a "No Concentration Assay" for detecting a microorganism of interest using a recombinant reproduction-deficient indicator phage according to an embodiment of the disclosure.

In certain embodiments, the assay may be performed without concentrating the microorganism of interest on or near the capture surface. FIG. 30 illustrates a "No Concentration Assay" for detecting a microorganism of interest using a reproduction-deficient indicator phage according to an embodiment of the invention. Aliquots of reproduction-deficient indicator phage 714 are distributed to the individual wells 702 of a multi-well plate 704, and then test sample aliquots containing microorganisms of interest 712 are added and incubated 706 (for example, 45 minutes at 37° C.) for a period of time sufficient for phage to generate soluble indicator 716 (for example, luciferase). The plate wells 708 containing soluble indicator and the reproduction-deficient indicator phage may then be assayed 710 to measure the indicator activity on the plate 718 (for example, luciferase assay). In this embodiment, the test samples are not concentrated (for example, by centrifugation) but are simply incubated directly with the reproduction-deficient indicator phage for a period of time and subsequently assayed for luciferase activity.

In some embodiments, the sample may be enriched prior to testing by incubation in conditions that encourage growth. In such embodiments, the enrichment period can be 1, 2, 3, 4, 5, 6, 7, 8, 9, 10, 11, 12, 13, 14, 15, or 16 hours or longer, depending on the sample type and size.

In some embodiments, the reproduction-deficient indicator phage comprises a detectable indicator moiety, and infection of a single pathogenic cell (for example, bacterium) can be detected by an amplified signal generated via the indicator moiety. Thus the method may comprise detecting an indicator moiety produced during reproduction-deficient indicator phage infection, wherein detection of the indicator indicates that a microorganism of interest, such as a bacterium of interest, is present in the sample. In an exemplary embodiment, the invention may comprise a method for detecting a bacterium of interest in a sample comprising the steps of: incubating the sample with a reproduction-deficient indicator phage that infects the bacterium of interest, wherein the reproduction-deficient indicator phage comprises an indicator gene inserted into a late gene region of the phage such that expression of the indicator gene following infection of the bacterium of interest results in production of a soluble indicator gene product; and detecting the indicator gene product, wherein positive detection (that is, the detection of presence, level or amount) of the indicator gene product indicates that the bacterium of interest is present in the sample. In some embodiments, the amount of indicator moiety detected corresponds to the amount of the bacterium of interest present in the sample.

As described in more detail herein, the methods and systems according to the embodiments of the invention may utilize a range of concentrations of reproduction-deficient indicator phage to infect microorganisms of interest (such as bacteria) that may be present in the sample. In some embodiments the reproduction-deficient indicator phage is added to the sample at a concentration sufficient to rapidly find, bind, and infect target microorganisms (such as bacteria) that are present in very low numbers in the sample, such as a single cell. In some embodiments, the concentration of reproduction-deficient indicator phage can be sufficient to find, bind, and infect the target bacteria in less than one hour. In other embodiments, these events can occur in less than two hours, or less than three hours, following addition of reproduction-deficient indicator phage to the sample. For example, in certain embodiments, the reproduction-deficient indicator phage concentration for the incubating step is greater than $1\times10^5$ PFU/mL, greater than $1\times10^6$ PFU/mL, greater than $1\times10^7$ PFU/mL, or greater than $1\times10^8$ PFU/mL.

In some embodiments of the methods for detecting a microorganism of interest in a sample, prior to the step of incubating the sample with a reproduction-deficient indicator phage that infects the microorganism of interest, the reproduction-deficient indicator phage may be purified so as to be free of any residual indicator protein that may be generated upon production of the infectious agent stock. Thus, in certain embodiments, the methods may include a step of purifying the reproduction-deficient indicator phage. The recombinant reproduction-deficient indicator phage may be purified by various methods, for example, by using cesium chloride isopycnic density gradient centrifugation prior to incubation with the sample. The purification may have the added benefit of removing phages that do not have DNA (that is, empty phages or "ghosts").

In some embodiments of the methods of the invention, the microorganism may be detected without any isolation or purification of the microorganisms from a sample. For example, in certain embodiments, a sample containing one or a few microorganisms of interest may be applied directly to an assay container such as a spin column, a microtiter well, or a filter and the assay is conducted in that assay container. Various embodiments of such assays are disclosed herein.

In many embodiments of the methods, multi-well plates are used to conduct the assays. For example, aliquots of a test sample may be distributed directly into wells of a multi-well plate, reproduction-deficient indicator phages added to the wells, and, after a period of time sufficient for infection, a lysis buffer may be added as well as a substrate for the indicator moiety (for example, luciferase substrate for a luciferase indicator) and assayed for detection of the indicator signal. Some embodiments of the method can be performed on filter plates. Some embodiments of the method can be performed with or without concentration of the sample before infection with reproduction-deficient indicator phage.

The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

Methods according to the embodiments of the invention may comprise various other steps to increase sensitivity. For example, as discussed in more detail herein, a method may comprise a step for washing the captured and infected microorganism (such as a bacterium), after adding the reproduction-deficient indicator phage but before incubating, to remove excess reproduction-deficient indicator phage and/or luciferase or other reporter protein contaminating the reproduction-deficient indicator phage preparation.

Methods according to the embodiments of the present invention may include one or more steps related to sample preparation, which can be referred to as "sampling" or "sampling steps." In some embodiments, samples may be used directly in the methods according to the embodiments of the present invention, without preparation, concentration, or dilution. For example, liquid samples may be assayed directly. In other embodiments, samples may be diluted or suspended in solution, which may include, but is not limited to, a buffered solution or a bacterial culture medium. A sample that is a solid or semi-solid may be suspended in a liquid by mincing, mixing or macerating the solid in the liquid. In some embodiments, a sample should be maintained within a pH range that promotes the attachment of the reproduction-deficient indicator phage to a microorganism of interest, such as a bacterium of interest. In some embodiments, the preferred pH range may be one suitable for the reproduction-deficient indicator phage to attach to a bacterial cell. A sample should also contain the appropriate concentrations of divalent and monovalent cations, including but not limited to Na+, Mg2+, and K+.

Preferably throughout detection assays, the sample is maintained at a temperature that maintains the viability of any microorganisms of interest potentially present in the sample. During steps in which reproduction-deficient indicator phages attaching to bacterial cells, it is preferable to maintain the sample at a temperature that facilitates the activity of the reproduction-deficient indicator phage. Such temperatures are at least about 25° C. and no greater than about 45° C. In some embodiments, the samples are maintained at about 37° C. In some embodiments the samples are subjected to gentle mixing or shaking during binding or attachment of reproduction-deficient indicator phage to a microorganism of interest.

Sampling can be performed using a variety of ways. In some embodiments, the samples (for example, food samples) are first liquefied and the solid support, for example, the solid support or bead, is dipped into the liquid sample. In some embodiments, the solid support is first soaked in the culture media in the tube before sampling. In some embodiments, the solid support is dry before sampling. In some embodiments, the liquid sample is first cultured for a period of time ("culture enrichment"), for example, less than 24 hours, less than 12 hours, less than an enrichment period of 9 hours or less, 8 hours or less, 7 hours or less, 6 hours or less, 5 hours or less, 4 hours or less, 3 hours or less, or 2 hours or less. In other embodiments, the sample may be enriched following capture of the microorganisms of interest on the solid support. In some embodiments, the solid support with microorganisms can be incubated in growth media to allow the microorganism to expand in number. This step is referred to as "incubation enrichment." In such embodiments, the enrichment period can be 1, 2, 3, 4, 5, 6, 7, or up to 8 hours or longer, depending on the sample type and size.

In some embodiments, detection of the microorganism of interest may be completed without the need for culturing the sample as a way to increase the population of the microorganisms. For example, in certain embodiments the total time required for detection is less than 26.0, 25.0, 24.0, 23.0, 22.0, 21.0, 20.0, 19.0, 18.0, 17.0, 16.0 hours, 15.0 hours, 14.0 hours, 13.0 hours, 12.0 hours, 11.0 hours, 10.0 hours, 9.0 hours, 8.0 hours, 7.0 hours, 6.0 hours, 5.0 hours, 4.0 hours, 3.0 hours, 2.5 hours, 2.0 hours, 1.5 hours, 1.0 hour, 45 minutes, or less than 30 minutes. Minimizing time to result is critical in various applications, for example, food and environmental testing for pathogens.

The methods according to the embodiments of the present invention may include the steps indented to cause a reproduction-deficient indicator phage to infect a microorganism of interest. For example, a reproduction-deficient indicator phage can be contacted or brought in contact with a microorganisms of interest by known methods, some of which are described in the present document. Upon contacting the of interest microorganism, the reproduction-deficient indicator phages infect the microorganism of interest and express the indicator gene. The infection time, that is, a time period between the time point when the sample is first contacted with a reproduction-deficient indicator phage and the time point when the detection steps are started (for example, a substrate for the enzymatic indicator moiety is added to the sample contacted with the reproduction-deficient indicator phage) may vary, depending on the type of reproduction-deficient indicator phage and concentration of the microorganism of interest in the sample. Using the apparatus in which the microorganisms of interest, such as bacteria, are captured on solid support can significantly reduce the time required for infection, for example, the infection time can be one hour or less, while in a standard assay, where no solid support is used to capture the bacteria, the infection is typically at least 4 hours, In certain embodiments, the time of infection for the methods disclosed herein is less than 6.0 hours, 5.0 hours, 4.0 hours, 3.0 hours, 2.5 hours, 2.0 hours, 1.5 hours, 1.0 hour, 45 minutes, or less than 30 minutes. In some embodiments, the time of infection is about 1 hour, about 2 hours, or about 3 hours.

The methods according to the embodiments of the present invention can include one more steps related to detecting the signal produced by the indicator. The indicator, produced by expression of the indicator gene, can be detected using known methods. For example, one or more signal producing components can be reacted with the indicator to generate a detectable signal. In some embodiments, the indicator can be a bioluminescent compound. If the indicator is an enzyme, then amplification of the detectable signal is obtained by reacting the enzyme with one or more substrates or additional enzymes and substrates to produce a detectable reaction product. In another signal producing system, the indicator can be a fluorescent compound where no enzymatic manipulation of the indicator is required to produce the detectable signal. Fluorescent molecules including, for example, fluorescein and rhodamine and their derivatives and analogs are suitable for use as indicators in such a system. In yet another embodiment, the indicator moiety can be a cofactor, then amplification of the detectable signal is obtained by reacting the cofactor with the enzyme and one or more substrates or additional enzymes and substrates to produces a detectable reaction product. In some embodiments, the detectable signal is colorimetric. It is noted that the selection of a particular indicator is not critical to the present invention, but the indicator will be capable of generating a detectable signal either by itself, or be instrumentally detectable, or be detectable in conjunction with one or more additional signal producing components, such as an enzyme/substrate signal producing system. In some embodiments, the detecting step will require addition of a substrate for the indicator enzyme to act on. Substrate can be added in a variety of ways. In some embodiments, the reaction of indicator (for example, luciferase) with substrate may continue for 30 minutes or more, and detection at various time points may be desirable for optimizing sensitivity. In some embodiments, luminometer readings may be taken initially and at 3-, or 5-, or 10-, or 15-minute intervals until the reaction is completed.

Some embodiments of the methods of the present invention include one or more steps related to detecting a signal of the indicator, which can be referred to as "detection." Detecting the a product indicator gene may include detecting its enzymatic activity. Detecting a product of the indicator gene may include detecting emissions of light or detecting optical density. In some embodiments the compartment of the apparatus or vessel in which the substrate is mixed with the test sample is transparent, such that any optical signal resulting from the infection and subsequent incubation with substrate is detectable without having to remove the sample from the compartment of the apparatus or the vessel. In this case, the signal can be detected through the wall of the compartment of the apparatus or the vessel. In some embodiments, the apparatus or the vessel containing the reacted sample is inserted into an instrument for detecting the signal that results. In other embodiments, a detecting instrument is used to scan the apparatus containing the reacted sample.

In some embodiments, a luminometer may be used to detect the reaction of indicator (for example, luciferase) with a substrate. The detection of RLU can be achieved with a luminometer, or other machines or devices may also be used, some examples being GLOMAX® 20/20 and GLOMAX® from PROMEGA® (Madison, Wis.). In some embodiments, a spectrophotometer, CCD camera, or CMOS camera may detect color changes and other light emissions. Absolute RLU are important for detection, but the signal to background ratio also needs to be high (for example, >2.0, >2.5, or >3.0) in order for single cells or low numbers of cells to be detected reliably. The background signal can be obtained by measuring control sample that does not contain microorganism using the same procedure as described above. In some embodiments, detection of signal from the reporter or indicator gene may include, for example, use of an instrument that employs photodiode or PMT (photomultiplier tube) technology. In some embodiments, a handheld luminometer may be employed for detection of signal. Suitable PMT handheld luminometers are available from 3M (Maplewood, Minn.), BIOCONTROL® (Seattle, Wash.), and CHARM SCIENCES® (Lawrence, Mass.). Suitable photodiode handheld luminometers are available from HYGIENA® (Camarillo, Calif.) and NEOGEN® (Lansing, Mich.). These handheld luminometers typically produce much lower readings as compared to traditional luminometers (such as GLOMAX® or GLOMAX® 20/20) for the same sample, but multiple experiments showed that the signals produced were sufficient to be detected by these handheld luminometers. Being able to use these handheld devices to detect the microorganism also offers convenience and flexibility that is often lacking with detection methods using traditional, non-handheld detection devices.

In some embodiments, the reproduction-deficient indicator phage is genetically engineered to contain the gene for an enzyme, such as a luciferase, which is only produced upon infection of the microorganism that the phage specifically recognizes and infects. In some embodiments, the indicator moiety is expressed late in the viral life cycle. In some embodiments, as described herein, the indicator is a soluble protein (for example, soluble luciferase) and is not fused with a phage structural protein that limits its copy number. Thus in some embodiments utilizing reproduction-deficient indicator phage, the invention comprises a method for detecting a microorganism of interest comprising the steps of capturing at least one sample microorganism of interest; incubating the at least one microorganism of interest with a plurality of reproduction-deficient indicator phages; allowing time for infection and expression of soluble indicator moiety; and detecting the indicator moiety, wherein detection of the indicator moiety demonstrates that the microorganism of interest is present in the sample.

For example, in some embodiments the test sample microorganism of interest may be captured by binding to the surface of a plate, or by filtering the sample through a bacteriological filter (for example, 0.45 µm pore size spin filter or plate filter). In an embodiment, the reproduction-deficient indicator phage is added in a minimal volume to the captured sample directly on the filter. In an embodiment, the microorganism captured on the filter or plate surface is subsequently washed one or more times to remove excess unbound reproduction-deficient indicator phage. In an embodiment, a medium (for example, Luria-Bertani Broth, also called LB herein, Buffered Peptone Water, also called BPW herein, or Tryptic Soy Broth or Tryptone Soy Broth, also called TSB herein) may be added for further incubation time, to allow sufficiently high level expression of the gene encoding the indicator moiety. In some embodiments, the incubation step with the reproduction-deficient indicator phage only needs to be long enough to achieve sufficient levels of expression of the gene encoding the indicator moiety to allow for a specified levels of signal detectable from the indicator moiety (for example, about 100-10000 RLU/s or about 200-5000 RLU/s), or specified levels of single-to-noise ratio (for example, 1-500, 5-200 or 10-100).

In some embodiments, aliquots of a test sample comprising microorganism of interest may be applied to a spin column and, after infection with a reproduction-deficient indicator phage and an optional washing to remove any excess reproduction-deficient indicator phage, the amount of soluble indicator detected will be proportional to the amount of reproduction-deficient indicator phage in the infected microorganism of interest.

Soluble indicator (for example, luciferase) released into the surrounding liquid upon lysis of the bacteria may then be measured and quantified. In an embodiment, the solution is spun through the filter, and the filtrate collected for assay in a new receptacle (for example, in a luminometer) following addition of a substrate for the indicator enzyme (for example, luciferase substrate). Alternatively, the indicator signal may be measured directly on the filter. Thus, in an exemplary embodiment, the indicator substrate (for example, luciferase substrate) may be incubated with the portion of the sample that remains on a filter or bound to a plate surface. Accordingly, in some embodiments the solid support is a 96-well filter plate (or regular 96-well plate), and the substrate reaction may be detected by placing the plate directly in the luminometer. For example, in an embodiment, the invention may comprise a method for detecting a microorganism of interest of interest comprising the steps of: infecting cells of the microorganism of interest captured on a 96-well filter plate with a plurality of reproduction-deficient indicator phage capable of expressing luciferase upon infection; washing excess reproduction-deficient indicator phage away; adding LB broth and allowing time for reproduction-deficient indicator phage to express luciferase and lyse the microorganism of interest (for example, 30-120 minutes, 60-120 min or 80-100 min, for example, about 90 min); and detecting the indicator luciferase by adding luciferase substrate and measuring luciferase activity directly in the 96-well plate, wherein detection of luciferase activity indicates that the bacterium of interest is present in the sample.

In another embodiment, the invention may comprise a method for detecting a microorganism of interest of interest comprising the steps of: infecting cells in liquid solution or suspension in a 96-well plate with a plurality of reproduction-deficient indicator phages capable of expressing luciferase upon infection; allowing time for reproduction-deficient indicator phages to express luciferase and to lyse the microorganism of interest (for example, 30-120 minutes; 60-120 min or 80-100 min, for example, about 90 min); and detecting the indicator luciferase by adding luciferase substrate and measuring luciferase activity directly in the 96-well plate, wherein detection of luciferase activity indicates that the microorganism of interest is present in the sample. In such an embodiment no capturing step is necessary. In some embodiments, the liquid solution or suspension may be a consumable test sample, such as a vegetable wash. In some embodiments, the liquid solution or suspension may be vegetable wash fortified with concentrated LB Broth, Tryptic/Tryptone Soy Broth, Peptone Water or Nutrient Broth. In some embodiments, the liquid solution or suspension may be bacteria diluted in LB Broth.

In some embodiments, lysis of the microorganism of interest may occur before, during, or after the detection step. Infected unlysed cells may be detectable upon addition of luciferase substrate in some embodiments. Luciferase may exit cells and/or luciferase substrate may enter cells without complete cell lysis. Thus, for embodiments utilizing the spin filter system, where only luciferase released into the lysate (and not luciferase still inside intact bacteria) is analyzed in the luminometer, lysis is required for detection. However, for embodiments utilizing filter plates or 96-well plates with sample in solution or suspension, where the original plate full of intact and lysed cells is directly assayed in the luminometer, lysis is not necessary for detection.

In some embodiments, the reaction of indicator moiety (for example, luciferase) with substrate may continue for 30 minutes or more, and detection at various time points may be desirable for optimizing sensitivity. For example, in embodiments using 96-well filter plates as the solid support and luciferase as the indicator, luminometer readings may be taken initially and at 10- or 15-minute intervals until the reaction is completed.

Surprisingly, high concentrations of reproduction-deficient indicator phage utilized for infecting test samples successfully achieve detection of very low numbers of target microorganism in a very short timeframe. The incubation of phage with a test sample in some embodiments need only be long enough for a single phage life cycle. In some embodiments, the reproduction-deficient indicator phage concentration for this incubating step is greater than $7 \times 10^6$, $8 \times 10^6$, $9 \times 10^6$, $1.0 \times 10^7$, $1.1 \times 10^7$, $1.2 \times 10^7$, $1.3 \times 10^7$, $1.4 \times 10^7$, $1.5 \times 10^7$, $1.6 \times 10^7$, $1.7 \times 10^7$, $1.8 \times 10^7$, $1.9 \times 10^7$, $2.0 \times 10^7$, $3.0 \times 10^7$, $4.0 \times 10^7$, $5.0 \times 10^7$, $6.0 \times 10^7$, $7.0 \times 10^7$, $8.0 \times 10^7$, $9.0 \times 10^7$, or $1.0 \times 10^8$ PFU/mL.

Embodiments of the methods of the present invention can detect individual microorganisms. Thus, in certain embodiments, the method may detect <10 cells of the microorganism (that is, 1, 2, 3, 4, 5, 6, 7, 8, 9 microorganisms) present in a sample. For example, in certain embodiments, a reproduction-deficient indicator phage is highly specific for a bacterium of interest. In an embodiment, the reproduction-deficient indicator phage can distinguish the bacterium of interest in the presence of other types of bacteria. In certain embodiments, the reproduction-deficient indicator phage can be used to detect a single bacterium of the specific type in the sample. In certain embodiments, the reproduction-deficient indicator phage detects as few as 2, 3, 4, 5, 6, 7, 8, 9, 10, 15, 20, 30, 40, 50, 60, 70, 80, 90, or 100 of the specific bacteria in the sample.

Large numbers of phages utilized for infection were previously associated with "lysis from without," which killed target cells and thereby prevented generation of useful signal. The clean-up of prepared stocks of reproduction-deficient indicator phage, as described herein, may help to alleviate this problem (for example, clean-up by cesium chloride isopycnic density gradient ultracentrifugation). In addition to removing any contaminating luciferase associated with the reproduction-deficient indicator phage, this clean-up may also remove ghost particles (particles that have lost DNA). The ghost particles can lyse bacterial cells via "lysis from without," killing the cells prematurely and thereby preventing generation of indicator signal. Electron microscopy demonstrates that a crude phage lysate (that is, before cesium chloride clean-up) may have greater than 50% ghosts. These ghost particles may contribute to premature death of the microorganism through the action of many phage particles puncturing the cell membrane. Thus ghost particles may have contributed to previous problems where high PFU concentrations were reported to be detrimental. Moreover, a purified preparation of reproduction-deficient indicator phage allows for the as assays to be performed with no wash steps, which makes the assays possible to perform without an initial concentration step. It is to be understood, however, that some embodiments of the methods of the present invention do include an initial concentration step, and in some embodiments this concentration step allows a shorter enrichment incubation time.

Some embodiments of the methods of the present invention may further include confirmatory assays. A variety of assays are known in the art for confirming an initial result, usually at a later point in time. For example, the samples can be cultured (for example, CHROMAGAR®, DYNABEADS® assay as described in the Examples, PCR can be utilized to confirm the presence of the microbial DNA, or other confirmatory assays can be used to confirm the initial result.

In certain embodiments, the methods of the present invention combine the use of a binding agent (for example, antibody) to purify and/or concentrate a microorganism of interest, such as a bacterium of interest, from the sample in addition to detection with an infectious agent. For example, in certain embodiments, the present invention comprises a method for detecting a microorganism of interest in a sample comprising the steps of: capturing the microorganism from the sample on a prior support using a capture antibody specific to the microorganism of interest, such as a bacterium of interest; incubating the sample with a reproduction-deficient indicator phage that infects the bacterium of interest, wherein the reproduction-deficient indicator phage comprises an indicator gene inserted into a late gene region of the reproduction-deficient indicator phage, such that expression of the indicator gene following infection the bacterium of interest results in a soluble indicator protein product; and, detecting the indicator protein product, wherein positive detection of the indicator protein product indicates that the bacterium of interest is present in the sample.

Figure 31:
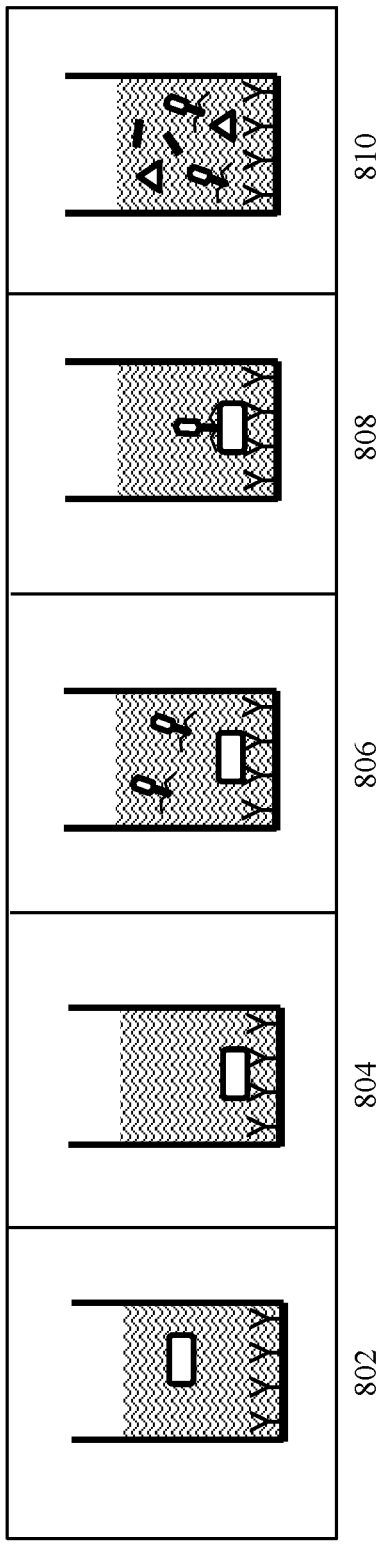
FIG. 31 depicts a Hybrid Immuno-Phage (HIP) Assay for detecting a microorganism of interest using a recombinant reproduction-deficient indicator phage according to an embodiment of the disclosure, in which antibodies to the microorganism of interest are used to capture the microorganism on the surface of the assay well prior to incubation with a recombinant reproduction-deficient indicator phage.

For example, FIG. 31 depicts a Hybrid Immuno-Phage (HIP) Assay for detecting a microorganism of interest using a reproduction-deficient indicator phage according to an embodiment of the invention. The sample is first applied to the microtiter plate well coated with microorganism-specific antibodies 802. The plate is then washed to facilitate binding of the microorganism of interest to the capture antibodies 804. Following sufficient time to allow for complete capture, a solution containing microorganism-specific reproduction-deficient indicator phage is added to each sample 806. Incubation with the phage results in the binding and attachment of a single or multiple phages to the captured microorganism 808. Finally, the sample is incubated to facilitate luciferase expression, which leads to cell lysis and release of soluble luciferase 810.

Systems and Kits

In some embodiments, the invention comprises systems (for example, automated systems or kits) comprising components for performing the methods disclosed herein. In some embodiments, reproduction-deficient indicator phages are comprised in systems or kits according to the invention. Methods described herein may also utilize such reproduction-deficient indicator phage systems and/or kits. Some embodiments described herein are particularly suitable for automation and/or kits, given the minimal amount of reagents and materials required to perform the methods. In certain embodiments, each of the components of a kit may comprise a self-contained unit that is deliverable from a first site to a second site.

In some embodiments, the invention comprises systems or kits for rapid detection of a microorganism of interest in a sample. The systems or kits may in certain embodiments comprise a component for incubating the sample with a reproduction-deficient indicator phage specific for the microorganism of interest, wherein the reproduction-deficient indicator phage comprises an indicator moiety and a component for detecting the indicator moiety. In some embodiments of both the systems and the kits of the invention, the reproduction-deficient indicator phage is capable of specifically infecting a bacterium of interest and comprises an indicator gene inserted into a late gene region of the reproduction-deficient indicator phage as the indicator moiety, such that expression of the indicator gene during the infection of the microorganism results in a soluble indicator protein product. Some systems further comprise a component for capturing the microorganism of interest on a solid support. The systems or kits may in certain embodiments comprise: an apparatus comprising a solid support, which comprises a cell-binding component, and a signal detecting component, wherein the signal detecting component can detect the indicator gene product produced from infecting a microorganism in a sample with the reproduction-deficient indicator phage. In some embodiments, the signal detecting component is a luminometer, which can be a handheld device.

In other embodiments, the invention comprises a method, system, or kit for rapid detection of a microorganism of interest in a sample, comprising a reproduction-deficient indicator phage component that is specific for the microorganism of interest, wherein the reproduction-deficient indicator phage comprises an indicator moiety, and a component for detecting the indicator moiety. In certain embodiments, the reproduction-deficient indicator phage is highly specific for a particular microorganism, such as a bacterium. In some embodiments, the reproduction-deficient indicator phage can distinguish a microorganism of interest, such as a bacterium, in the presence of other types of microorganisms. In certain embodiments, a system or kit detects as few as 2, 3, 4, 5, 6, 7, 8, 9, 10, 15, 20, 30, 40, 50, 60, 70, 80, 90, or 100 specific microorganisms of interest in the sample.

In certain embodiments, the invention may comprise a system or kit for rapid detection of a microorganism of interest in a sample, comprising an apparatus having a first compartment comprising a reproduction-deficient indicator phage. The apparatus may further comprise a second compartment that contain substrate, and/or a third compartment that contain media. One or more of these compartments are sealed and separate from the other portion of the apparatus by a snap-action seal, and the breaking the snap-action seal causes the contents from the compartment to leave the compartment and mix with the sample. Alternatively, a system or a kit may further comprise separate vessels that contain substrate and/or media.

In certain embodiments, a system and/or a kit may further comprise a component for washing the captured microorganism sample. Additionally or alternatively, the systems and/or kits may further comprise a component for determining amount of the indicator moiety, wherein the amount of indicator moiety detected corresponds to the amount of microorganism in the sample. For example, in certain embodiments, the system or kit may comprise a luminometer or other device for measuring a luciferase enzyme activity.

In some embodiments, a system and/or a kit may comprise a component for isolating the microorganism of interest from the other components in the sample. In some systems and/or kits, the same component may be used for multiple steps. In some systems and/or kits, the steps are automated or controlled by the user via computer input and/or wherein a liquid-handling robot performs at least one step. In a computerized system, the system may be fully automated, semi-automated, or directed by the user through a computer (or some combination thereof)

Thus in certain embodiments, the invention may comprise a system or kit for rapid detection of a microorganism of interest in a sample, comprising: a component for incubating the sample with a reproduction-deficient indicator phage specific for the microorganism of interest, wherein the reproduction-deficient indicator phage comprises an indicator moiety; a component for capturing the microorganism of interest from the sample on a solid support; a component for washing the captured microorganism of interest to remove unbound reproduction-deficient indicator phage; and a component for detecting the indicator moiety. In some embodiments, the same component may be used for steps of capturing and/or incubating and/or washing (for example, a filter component). Some embodiments additionally comprise a component for determining amount of the microorganism of interest in the sample, wherein the amount of indicator moiety detected corresponds to the amount of microorganism in the sample. Such systems can include various embodiments and subembodiments analogous to those described above for methods of rapid detection of microorganisms. In an embodiment, the microorganism is a bacterium. In a computerized system, the system may be fully automated, semi-automated, or directed by the user through a computer (or some combination thereof). In some embodiments, the system may comprise a component for isolating the microorganism of interest from the other components in the sample.

In an embodiment, the disclosure comprises a system or kit comprising components for detecting a microorganism of interest comprising: a component for isolating at least one microorganism from other components in the sample; a component for infecting at least one microorganism with a plurality of reproduction-deficient indicator phages; a component for lysing the at least one infected microorganism to release reproduction-deficient indicator phage present in the microorganism; and a component for detecting the reproduction-deficient indicator phage, or, possibly with greater sensitivity, a soluble protein encoded and expressed by the reproduction-deficient indicator phage, wherein detection of the reproduction-deficient indicator phage or a soluble protein product of the reproduction-deficient indicator phage indicates that the microorganism is present in the sample. The reproduction-deficient indicator phage may be a NANOLUC® reproduction-deficient indicator phage carrying the NANOLUC® indicator gene.

In other embodiments, the disclosure may comprise a kit for rapid detection of a microorganism of interest in a sample, the system comprising: a component for incubating the sample with a reproduction-deficient indicator phage specific for the microorganism of interest, wherein the reproduction-deficient indicator phage comprises an indicator moiety; a component for capturing the microorganism of interest from the sample on a solid support; a component for washing the captured microorganism of interest to remove unbound reproduction-deficient indicator phage; and a component for detecting the indicator moiety. In some embodiments, the same component may be used for steps of capturing and/or incubating and/or washing. Some embodiments additionally comprise a component for determining amount of the microorganism of interest in the sample, wherein the amount of indicator moiety detected corresponds to the amount of microorganism of interest in the sample. Such kits can include various embodiments and subembodiments analogous to those described above for methods of rapid detection of microorganisms. In an embodiment, the microorganism is a bacterium. In some embodiments, a kit may comprise a component for isolating the microorganism of interest from the other components in the sample.

These systems and kits of the disclosure include various components. As used herein, the term "component" is broadly defined and includes any suitable apparatus or collections of apparatuses suitable for carrying out the recited method. The components need not be integrally connected or situated with respect to each other in any particular way. The disclosure includes any suitable arrangements of the components with respect to each other. For example, the components need not be in the same room. But in some embodiments, the components are connected to each other in an integral unit. In some embodiments, the same components may perform multiple functions.

Computer Systems and Computer Readable Media

In certain embodiments, the disclosure may comprise a system. The system may include at least some of the compositions of the disclosure. Also, the system may comprise at least some of the components for performing the method. In certain embodiments, the system is formulated as a kit. Thus, in certain embodiments, the disclosure may comprise a system for rapid detection of a microorganism of interest in a sample. The system may include at least some of the compositions of the disclosure. Also, the system may comprise at least some of the components for performing the method. In certain embodiments, the system is formulated as a kit. Thus, in certain embodiments, the disclosure may comprise a system for rapid detection of a microorganism of interest in a sample, comprising an apparatus as described above. For example, the apparatus may comprise a first compartment comprising recombinant bacteriophage having a genetic construct inserted into a bacteriophage genome, wherein the construct comprises a promoter and an indicator gene; wherein the solid support comprises a cell binding component. In some embodiments, the system also comprises a handheld detection device.

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

A computer system may comprise a computer, an input device, a display unit, and/or the Internet. The computer may further comprise a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit allows the computer to connect to other databases and the Internet through an I/O interface. The communication unit allows the transfer to, as well as reception of data from, other databases. The communication unit may include a modem, an Ethernet card, or any similar device which enables the computer system to connect to databases and networks such as LAN, MAN, WAN and the Internet. The computer system thus may facilitate inputs from a user through input device, accessible to the system through I/O interface.

A computing device typically will include an operating system that provides executable program instructions for the general administration and operation of that computing device, and typically will include a computer-readable storage medium (for example, a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (for example, a mouse, keyboard, controller, touch screen, or keypad), and at least one output device (for example, a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (for example, a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may comprise a single type of computer-readable medium such as random access memory (RAM). In other embodiments, the computing device may comprise two or more types of computer-readable medium such as random access memory (RAM), a disk drive, and cache. The computing device may be in communication with one or more external computer-readable mediums such as an external hard disk drive or an external DVD or Blu-Ray drive.

As discussed above, the embodiment comprises a processor which is configured to execute computer-executable program instructions and/or to access information stored in memory. The instructions may comprise processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif.). In an embodiment, the computing device comprises a single processor. In other embodiments, the device comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device comprises a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, the computing device may include a data store in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device may be in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present disclosure has been disclosed with references to certain embodiments, numerous modifications, alterations and changes to the described embodiments are possible without departing from the scope and spirit of the present disclosure, as defined in the appended claims. Accordingly, it is intended that the present disclosure not be limited to the described embodiments, but that it have the full scope defined by the language of the following claims, and equivalents thereof.

EXAMPLES

The following examples describe detection of a low number of cells, even a single bacterium, in a shortened time to results and are to illustrate but not limit the disclosure.

Figure 5:
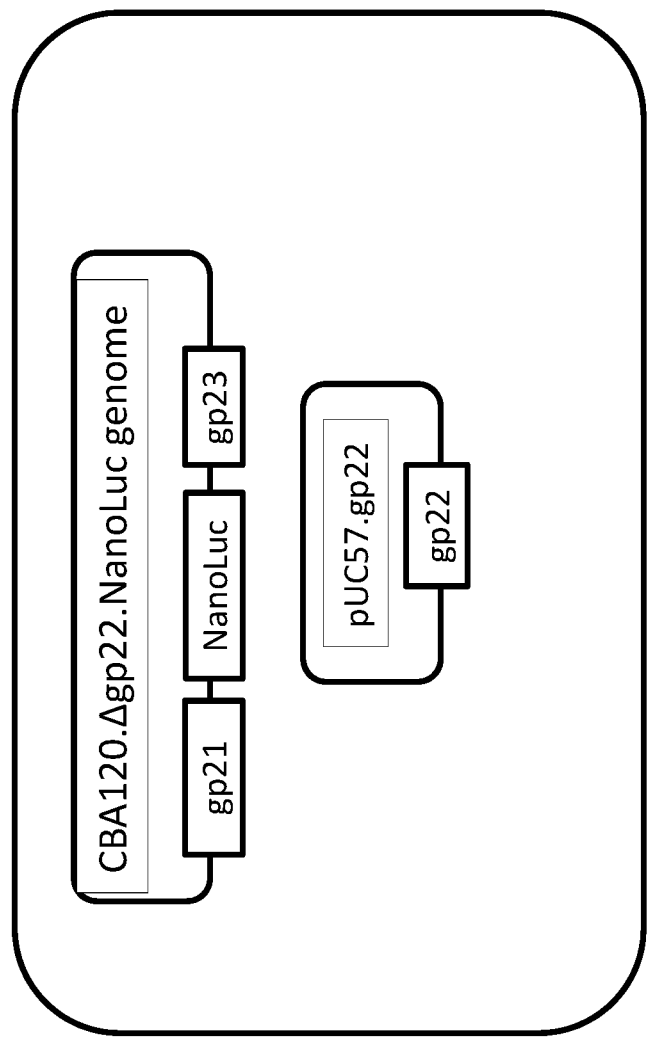
FIG. 5 schematically illustrates propagation of a recombinant reproduction-deficient indicator phage specific for *E. coli* O157:H7 serotype performed in an engineered *E. coli* O157:H7 strain transformed with the plasmid expressing gp22 prohead scaffold protein ("permissive" *E. coli* O157:H7 strain).
Figure 6:
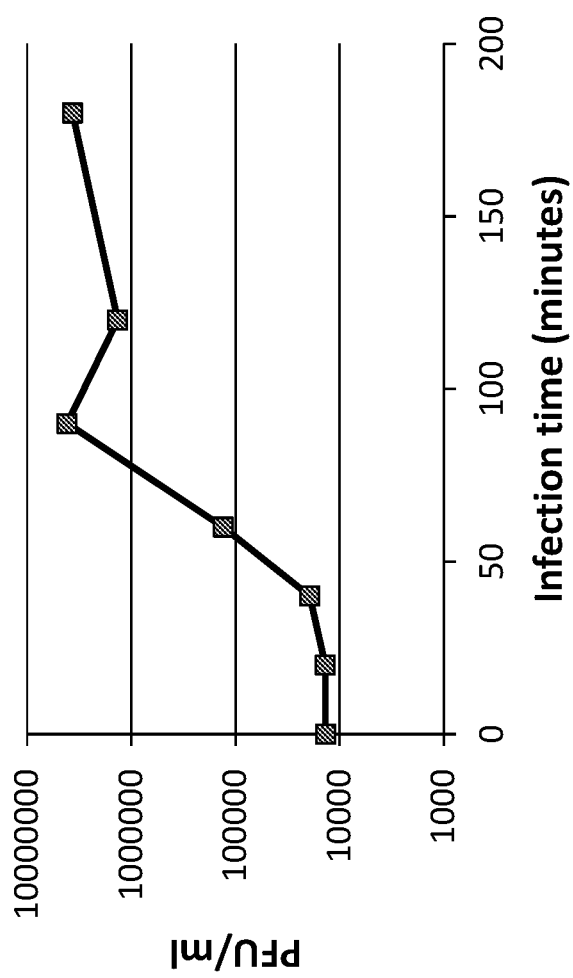
FIG. 6 shows an exemplary growth curve of the reproduction-deficient indicator phage, where the phage was successfully grown in the permissive *E. coli* O157:H7 strain.

Example 1. Creation and Isolation of Reproduction-Deficient Indicator Phage from a Bacteriophage Specific For *E. coli* O157:117 Serotype Reproduction-deficient indicator phage specific for *E. coli* O157:H7 serotype was constructed from a parent phage specific for *E. coli* O157:H7 serotype by using homologous recombination as illustrated in FIG. 3. To generate the Reproduction-deficient indicator phage, the coding sequence of gp22 prohead scaffold protein of the parent phage was replaced with NANOLUC® coding sequence. *E. coli* O157:H7 were transformed with the both the Homologous Recombination plasmid (HR plasmid in FIG. 3) containing the NANOLUC® gene flanked by matching bacterial genomic sequences flanking gp22, and a plasmid containing an expression cassette for gp22 (pBAV.gp22 in FIG. 3), each under a separate antibiotic selection to insure transformed bacteria contain both plasmids. These doubly transformed bacteria were infected with the parent phage to allow for homologous recombination with the HR plasmid, deleting the phage's copy of gp22, which is then provided in trans by the gp22-encoding plasmid. Following homologous recombination, a series of titer and enrichment steps was used to isolate specific recombinant bacteriophages that express NANOLUC®. Large-scale production was performed to obtain high titer stocks of reproduction-deficient indicator phage appropriate for use in the detection assays. Due to the inability of the reproduction-deficient indicator phage (termed CBA120Δgp22 NanoLuc) to propagate in wild-type *E. coli* O157:H7, the propagation was performed in an engineered *E. coli* O157:H7 strain transformed with the high copy pUC based plasmid expressing gp22 prohead scaffold protein ("permissive" *E. coli* O157:H7 strain) as illustrated in FIG. 5. As illustrated by the growth curve shown in FIG. 6, the reproduction-deficient indicator phage was successfully grown in the permissive *E. coli* O157:H7 strain. Cesium chloride isopycnic density gradient centrifugation was used to separate phage particles from contaminating luciferase protein to reduce background.

Figure 7:
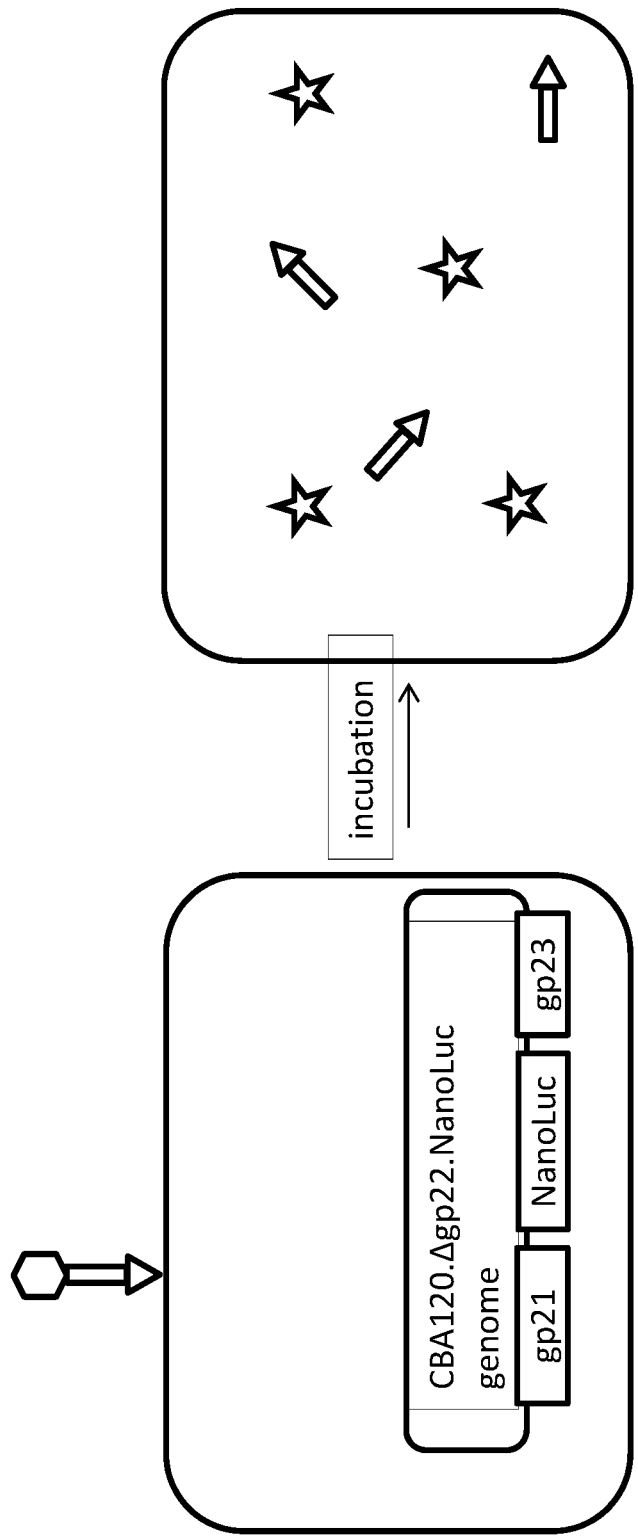
FIG. 7 schematically illustrates the strategy of using the reproduction-deficient indicator phage specific for *E. coli* O157:H7 serotype.

Example 2. Testing of Reproduction-Deficient Indicator Phage Specific for *E. coli* O157:117 Serotype in a Detection Assay The strategy of using the reproduction-deficient indicator phage CBA120Δgp22 NanoLuc specific for *E. coli* O157:H7 serotype is shown in FIG. 7. Upon infection of *E. coli* O157:H7, the reproduction-deficient indicator phage produced soluble luciferase. The reproduction-deficient indicator phage was unable to form phage heads due to missing gp22 protein. The reproduction-deficient indicator phage produced no viable daughter phage.

To assess the activity of CBA120Δgp22 NanoLuc reproduction-deficient indicator phage, its detection activity was compared to that of CBA120 NanoLuc, a reproduction-capable indicator phage specific for *E. coli* O157:H7, with the NANOLUC® gene inserted after gp23, the major capsid protein gene under the control of T4 late gene promoter. Log- and stationary-phase cultures of *E. coli* O157:H7 (ATCC 43888) were diluted to obtain approximately the number of CFUs indicated on the x-axes of FIGS. 8-11 when 100 μl of sample was used. Each sample was infected with either CBA120 NanoLuc or CBA120Δgp22 NanoLuc for 2 hours at 37° C. Lysis buffer and luciferase substrate were added and the samples were read on a luminometer. Five replicates of the measurements were performed at each CFU level for each phage. RLU values for each CFU were averaged. Signal/Background values plotted on the y-axes of FIGS. 8-11 were calculated using average values at each CFU level reading and dividing by the average of 0 CFU readings.

Figure 8:
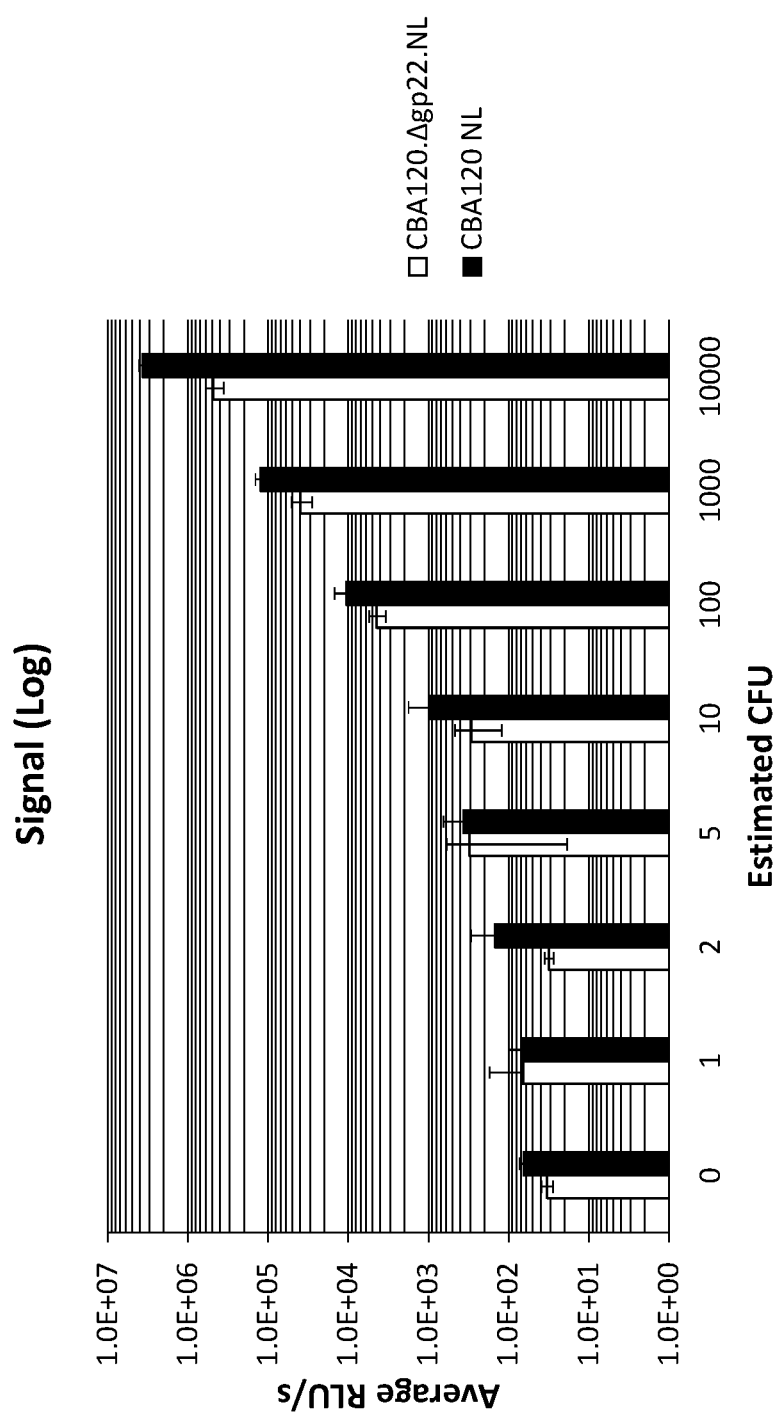
FIG. 8 is a bar graph illustrating the raw signal results of the detection assay using the reproduction-deficient indicator phage compared to reproduction-capable indicator phage specific for *E. coli* O157:H7 serotype performed on *E. coli* O157:H7 in a log phase.
Figure 9:
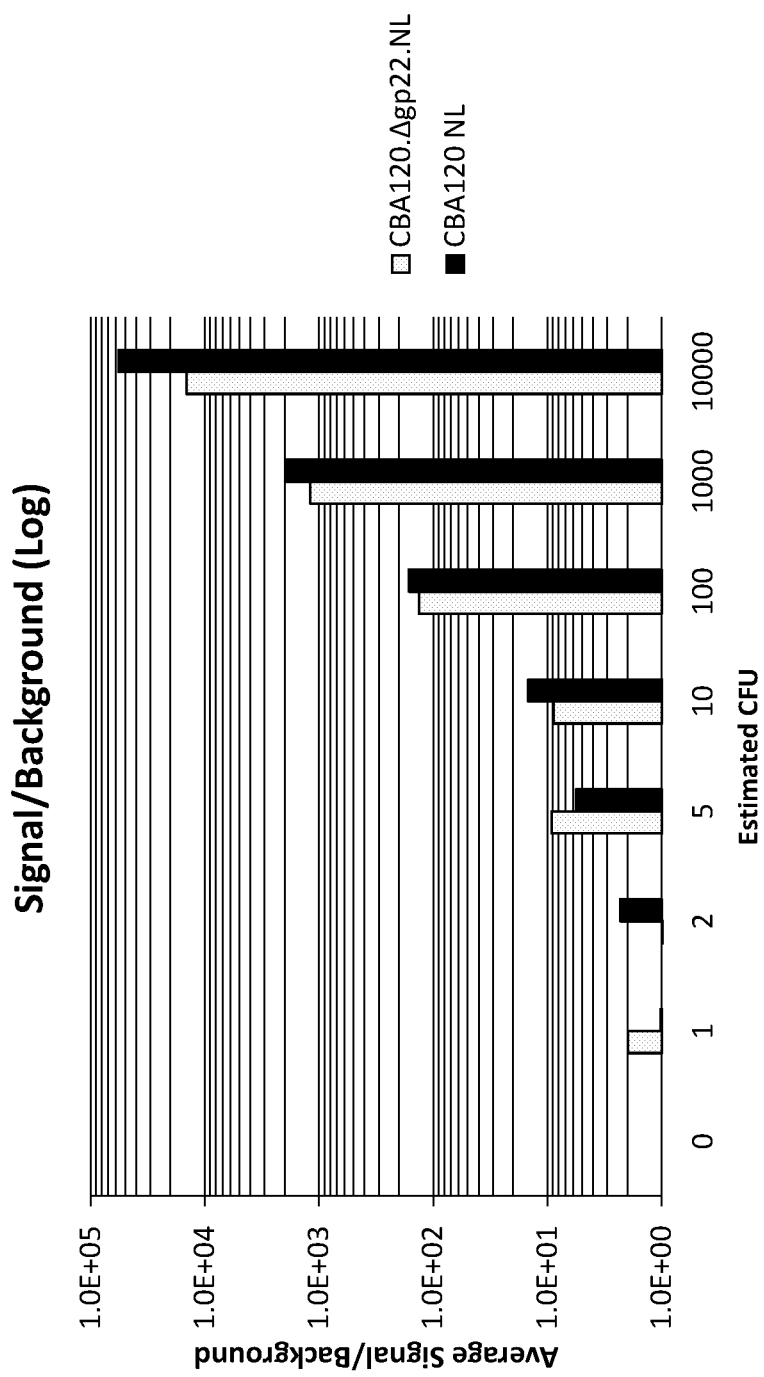
FIG. 9 is a bar graph illustrating the signal to background results of the detection assay using the reproduction-deficient indicator phage compared to reproduction-capable indicator phage specific for *E. coli* O157:H7 serotype performed on *E. coli* O157:H7 in a log phase.
Figure 10:
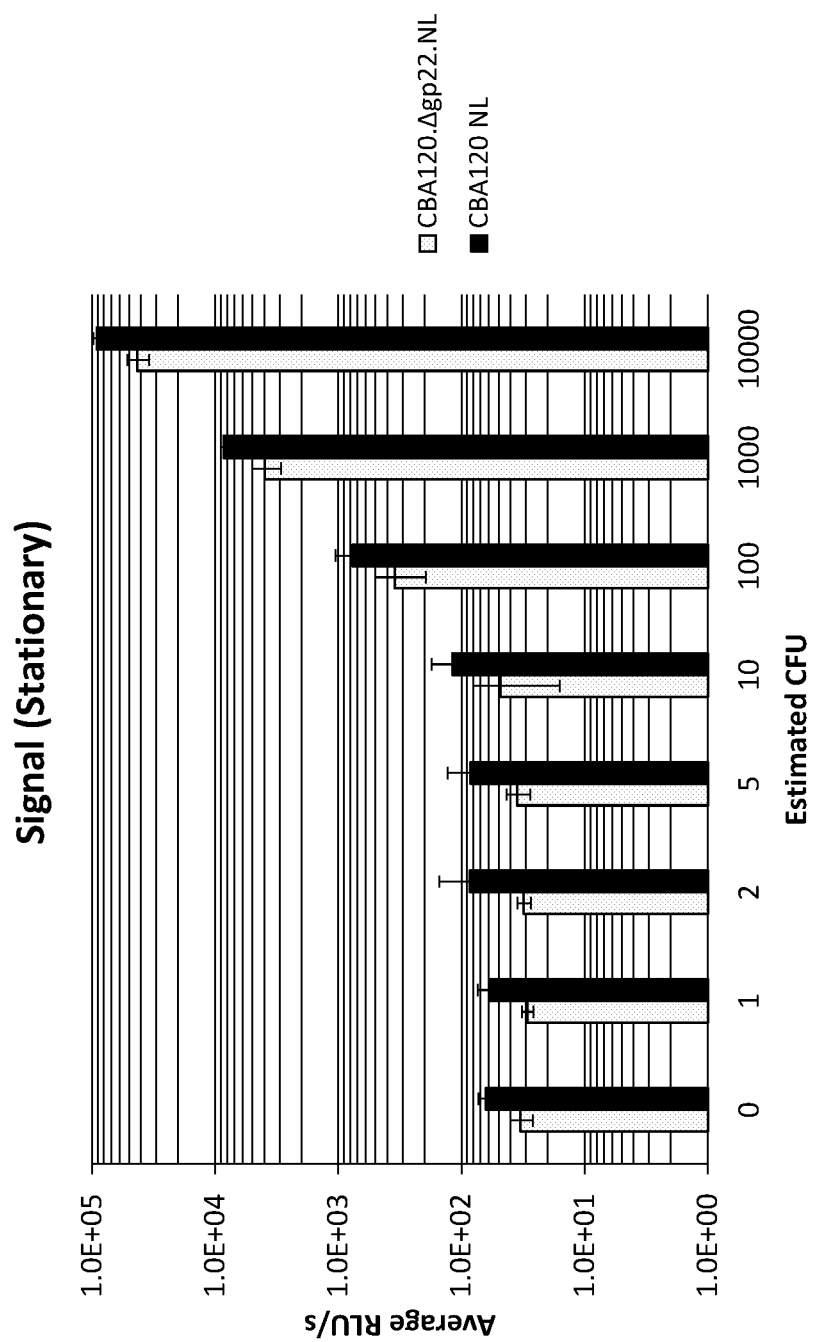
FIG. 10 is a bar graph illustrating the raw signal results of the detection assay using the reproduction-deficient indicator phage compared to reproduction-capable indicator phage specific for *E. coli* O157:H7 serotype performed on *E. coli* O157:H7 in a stationary phase.
Figure 11:
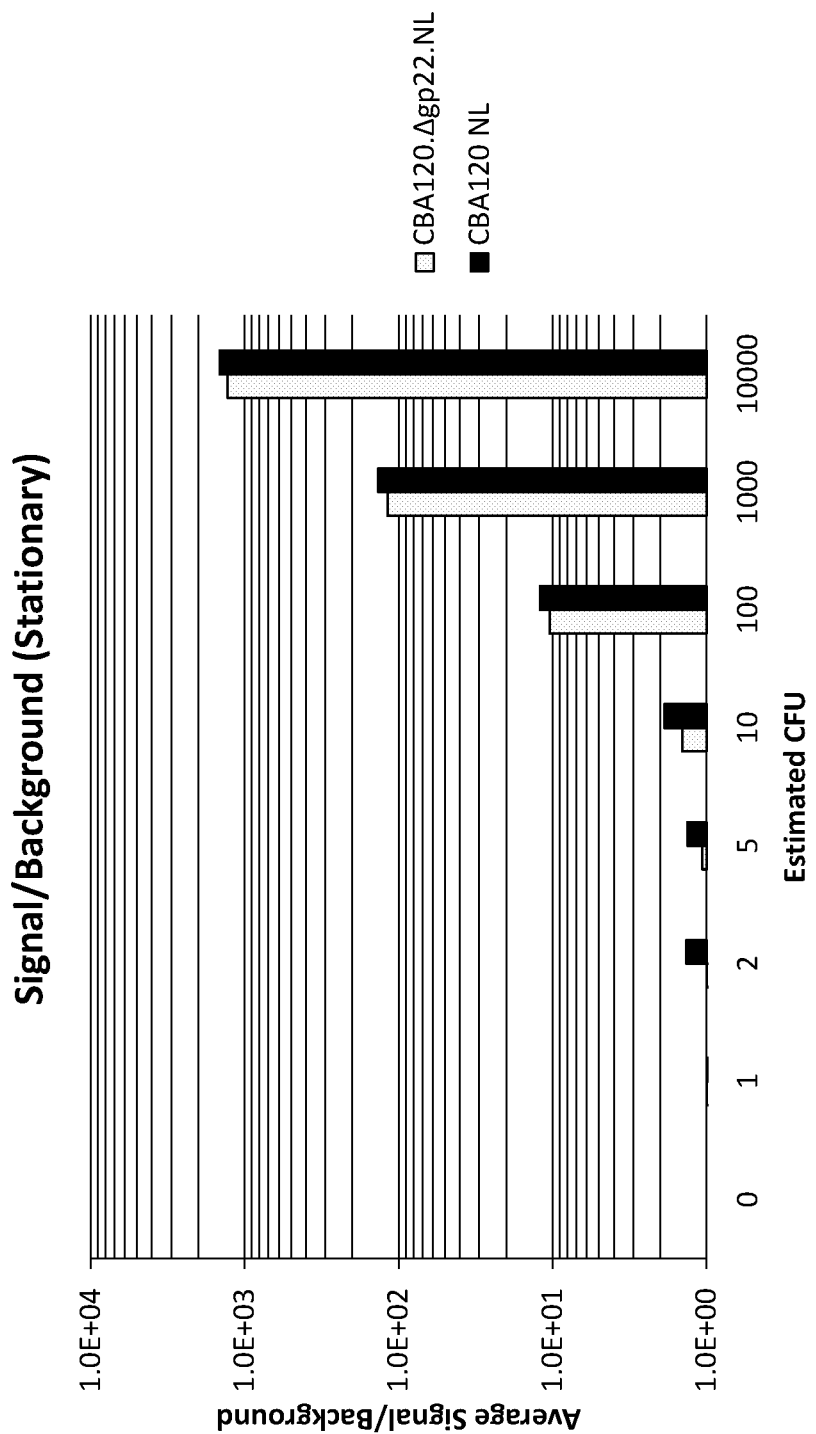
FIG. 11 is a bar graph illustrating the signal to background results of the detection assay using the reproduction-deficient indicator phage compared to reproduction-capable indicator phage specific for *E. coli* O157:H7 serotype performed on *E. coli* O157:H7 in a stationary phase.

The above experiments were performed on *E. coli* O157:H7 culture samples in log phase, in which the bacterial cells typically generate higher signal levels due to high levels of transcription and protein expression. The results are illustrated in FIGS. 8 and 9. The above experiments were performed on *E. coli* O157:H7 culture samples in stationary phase, in which the bacterial cells typically generate lower signal levels due to lower levels of transcription and protein expression. The results are illustrated in FIGS. 10 and 11. In FIGS. 8 and 9, the white bars indicate the results obtained for the reproduction-deficient indicator phage (labelled CBA12.Δgp22.NL), and the filled bars indicate the results for the positive control (labelled CBA120NL). FIGS. 8-11 show that the reproduction-deficient indicator phage performed comparably to the positive control.

Figure 12:
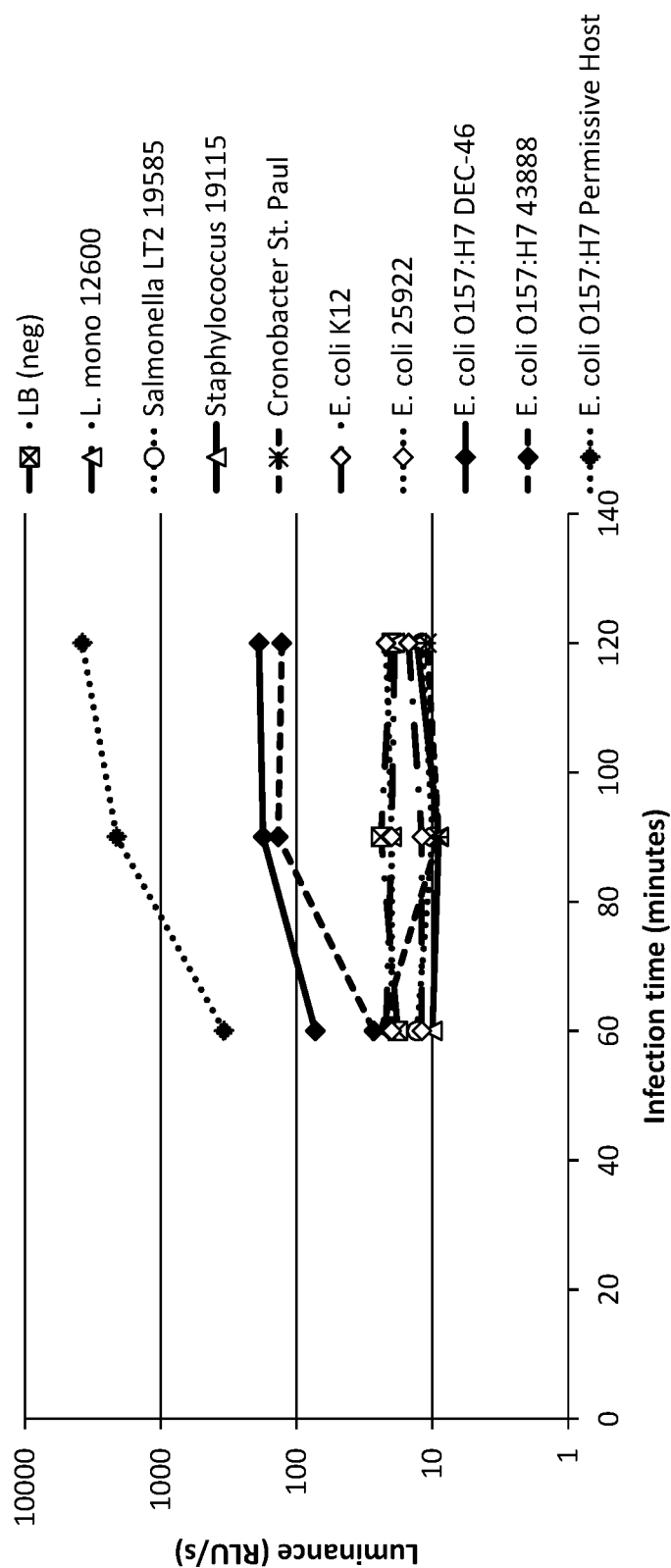
FIG. 12 is a line plot illustrating the results of the specificity determination of the reproduction-deficient indicator phage specific for *E. coli* O157:H7 serotype.

Example 3. Testing Specificity of Reproduction-Deficient Indicator Phage Specific For *E. coli* O157:117 Serotype Specificity of the reproduction-deficient indicator phage specific for *E. coli* O157:H7 serotype was tested. The detection assay was performed as described in the previous example to detect a range of bacteria. The results are illustrated in FIG. 12. The luciferase signal was produced during the detection of *E. coli* O157:H7 or engineered permissive *E. coli* O157:H7. No luciferase signal was detected during the attempted detection of non-target bacterial, including several *E. coli* serotypes.

Example 4. Creation and Isolation of Reproduction-Deficient Indicator Phage from a TSP1 Bacteriophage Specific For *Salmonella*

Figure 13:
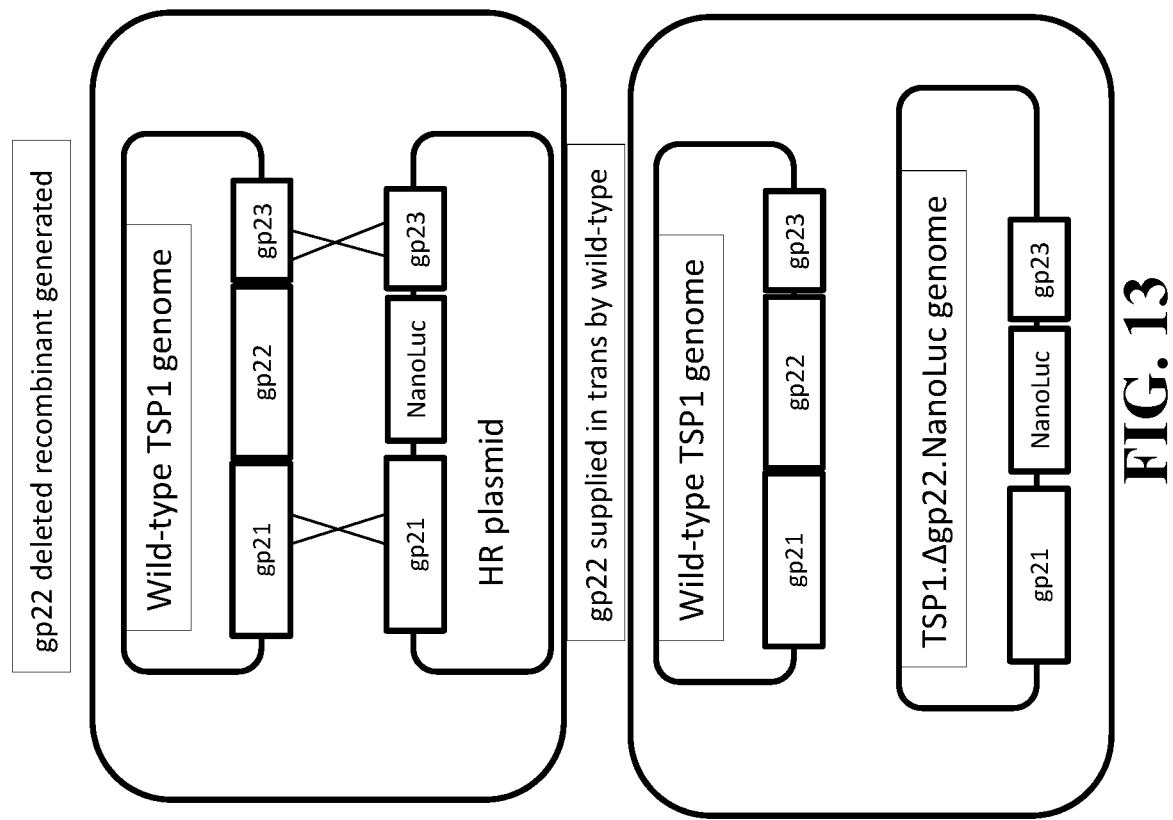
FIG. 13 schematically illustrates homologous recombination with co-infection trans complementation of a TSP1 *Salmonella*-specific phage to produce a reproduction-deficient indicator phage TSP1.Δgp22.NanoLuc.
Figure 14:
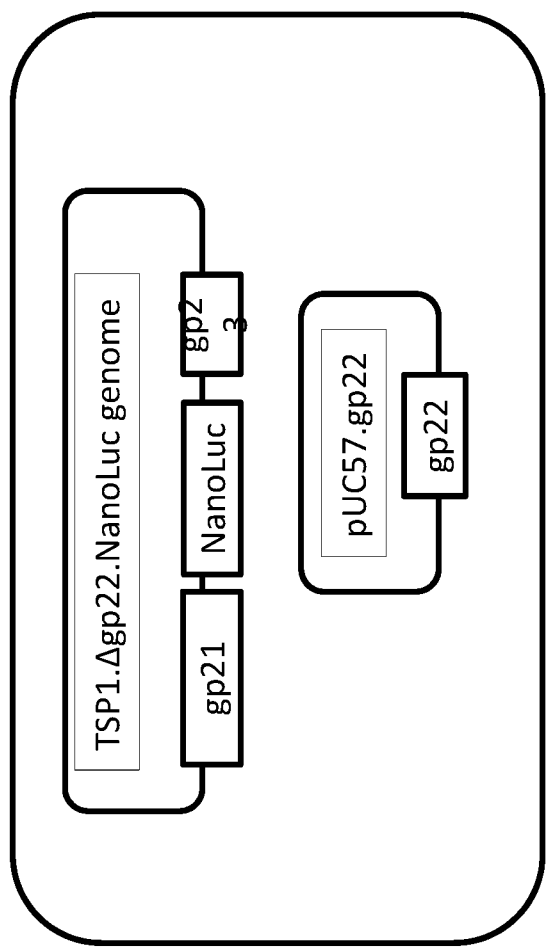
FIG. 14 schematically illustrates propagation of a recombinant reproduction-deficient indicator phage specific for *Salmonella* performed in an engineered *Salmonella* strain transformed with the plasmid expressing gp22 prohead scaffold protein ("permissive" *Salmonella* strain).

A reproduction-deficient indicator phage specific for *Salmonella* was constructed from a parent phage specific for *Salmonella* by using homologous recombination as illustrated in FIG. 13. To generate the reproduction-deficient indicator phage, the coding sequence of gp22 prohead scaffold protein of the parent phage was replaced with NANOLUC® coding sequence in wild-type TSP1. *Salmonella* ATCC 19585 were transformed with the Homologous Recombination (HR) plasmid containing the NanoLuc gene flanked by matching bacterial genomic sequences flanking gp22 (i.e., the gp21 prohead core and protease and gp23 major capsid protein) (FIG. 13). The transformed bacteria were infected with the parent phage to allow for homologous recombination with the HR plasmid, deleting the phage's copy of gp22, thereby, simultaneously creating reproduction-deficient mutants and inserting the indicator gene (i.e., NANOLUC®) to create reproduction-deficient indicator phage. Infected cells produced a mix of wild-type and recombinant bacteriophages at a ratio of approximately 1:8 recombinant:wild-type phages. Co-infecting wild-type phages supports recombinant replication by complementing the missing gp22 gene in trans. Following homologous recombination, a series of titer and enrichment steps was used to isolate specific recombinant bacteriophages that express NANOLUC®. Large-scale production was performed to obtain high titer stocks of reproduction-deficient indicator phage appropriate for use in the detection assays. Due to the inability of the reproduction-deficient indicator phage (termed TSP1.Δgp22 NanoLuc) to propagate in wild-type *Salmonella* 19585, the propagation was performed in an engineered *Salmonella* strain transformed with the high copy pUC based plasmid expressing gp22 prohead scaffold protein ("permissive" *Salmonella* strain) as illustrated in FIG. 14.

Figure 15:
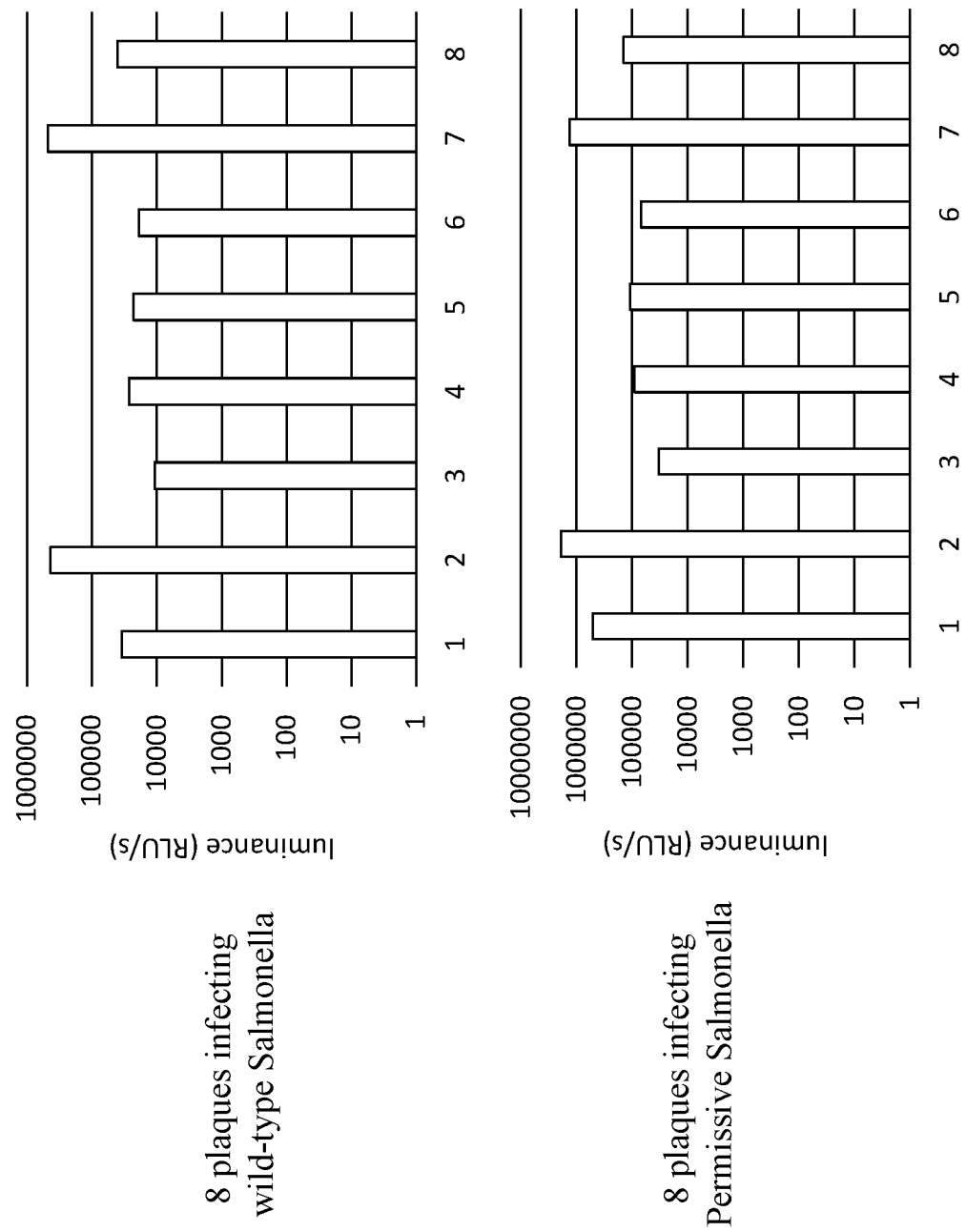
FIG. 15 is a bar graph illustrating the raw signal results of the detection assay using the reproduction-deficient indicator phage in wild-type *Salmonella* compared to permissive *Salmonella*.

Isolated TSP1.Δgp22.NanoLuc plaques were suspended in TMS buffer, inoculated into either wild-type or permissive *Salmonella* 19585 cultures, and incubated for 3 hours at 37° C. NanoGlo (PROMEGA®) assays were performed on 10 μl samples. TSP1.Δgp22.NanoLuc infection of both wild-type and permissive *Salmonella* resulted in high signal over background (100 RLU/s) (FIG. 15).

Example 5. Testing of Reproduction-Deficient TSP1 Indicator Phage Specific for *Salmonella* Limit of Detection To assess the limit of detection of TSP1.Δgp22.NanoLuc reproduction-deficient indicator phage in stationary phase *Salmonella*, *Salmonella Typhimurium* ATCC 19585 was grown 18-20 hours to stationary phase. The stationary phase culture was diluted in TSB and cells were transferred to a 96-well plate according to the plate layout shown in FIG. 16. TSP1.Δgp22.NanoLuc phages were added to the *Salmonella* stationary phase culture and incubated for two hours at 37° C. Following infection with the phages, lysis buffer, assay buffer, and substrate were added and the plate was read for 1 second in a luminometer. Results are shown in FIG. 16.

To assess the limit of detection of TSP1.Δgp22.NanoLuc reproduction-deficient indicator phages in log phase *Salmonella*, *Salmonella Typhimurium* ATCC 19585 was grown 18-20 hours to stationary phase. Stationary phase cell cultures were then diluted in TSB and grown to early log phase. The log phase *Salmonella* culture was then diluted in TSB, and cells were transferred to a 96-well plate according to the layout shown in FIG. 17. TSP1.Δgp22.NanoLuc phages were added to the *Salmonella* log culture and incubated for two hours at 37° C. Following infection with the phages, lysis buffer, assay buffer, and substrate were added and the plate was read for 1 second in a luminometer. Results are shown in FIG. 17.

Example 6. Creation and Isolation of Reproduction-Deficient SEA1 Indicator Phage from a Bacteriophage Specific for *Salmonella*

Figure 18:
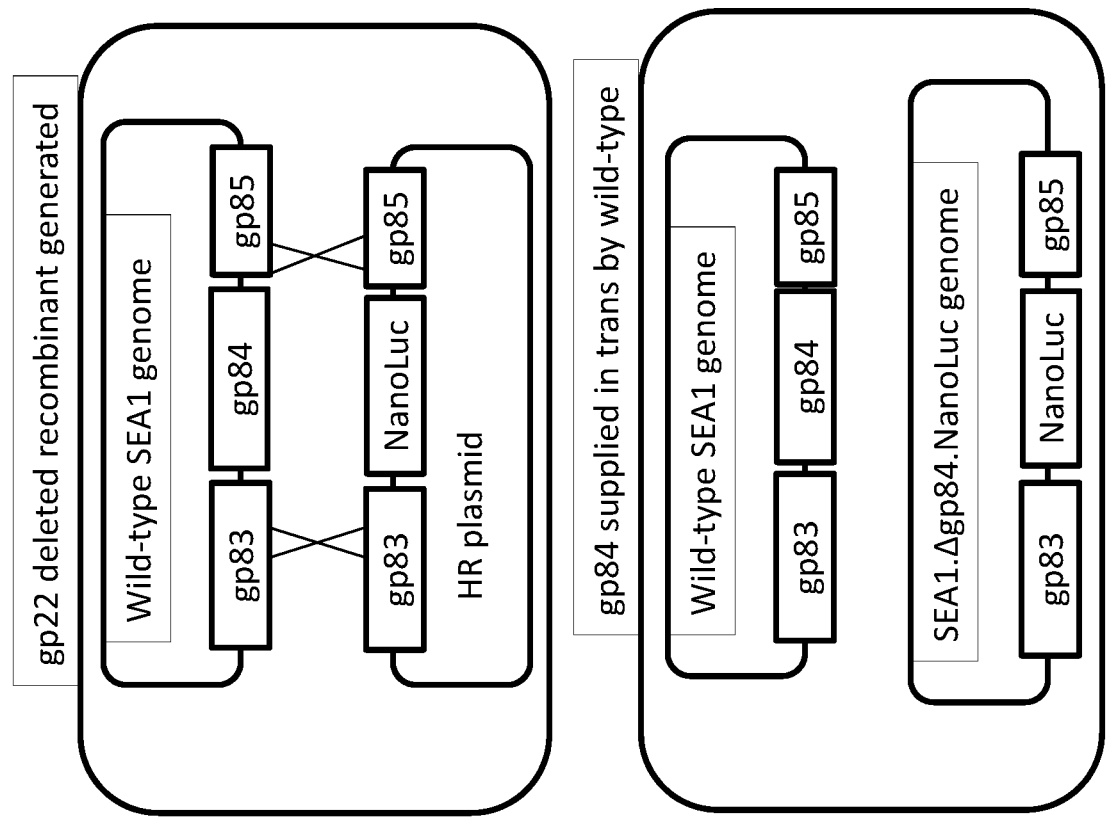
FIG. 18 schematically illustrates homologous recombination with co-infection trans complementation of a SEA1 *Salmonella*-specific phage to produce a reproduction-deficient indicator phage SEA1.Δgp84.NanoLuc.
Figure 19:
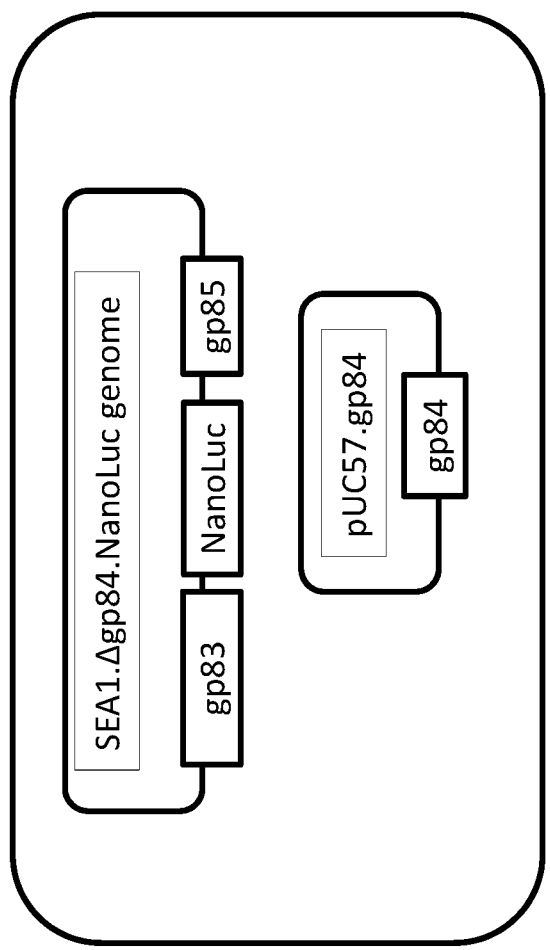
FIG. 19 schematically illustrates propagation of a recombinant reproduction-deficient indicator phage specific for *Salmonella* performed in an engineered *Salmonella* strain transformed with the plasmid expressing gp84 baseplate wedge protein ("permissive" *Salmonella* strain).

A reproduction-deficient indicator phage specific for *Salmonella* was constructed from a parent phage specific for *Salmonella* by using homologous recombination as illustrated in FIG. 18. To generate the reproduction-deficient indicator phage, the coding sequence of gp84 baseplate wedge subunit protein of the parent phage was replaced with NANOLUC® coding sequence in wild-type SEA1. *Salmonella* 27869 were transformed with both the Homologous Recombination (HR) plasmid containing the NanoLuc gene flanked by matching bacterial genomic sequences flanking gp84 (i.e., the gp83 head completion protein and gp85 baseplate hub subunit and tail lysozyme) (FIG. 18). These transformed bacteria were then infected with the parent phage to allow for homologous recombination with the HR plasmid, deleting the phage's copy of gp84, thereby, simultaneously creating reproduction-deficient mutants and inserting the indicator gene (i.e., NANOLUC®) to create reproduction-deficient indicator phage. Infected cells produced a mix of wild-type and recombinant bacteriophages. Co-infecting wild-type phages supports recombinant replication by complementing the missing gp84 gene in trans. Following homologous recombination, a series of titer and enrichment steps was used to isolate specific recombinant bacteriophages that express NANOLUC®. Large-scale production was performed to obtain high titer stocks of reproduction-deficient indicator phage appropriate for use in the detection assays. Due to the inability of the reproduction-deficient indicator phage (termed SEA1.Δgp84.NanoLuc) to propagate in wild-type *Salmonella* 27869, the propagation was performed in an engineered *Salmonella* strain transformed with the high copy pUC based plasmid expressing gp84 baseplate wedge subunit protein ("permissive" *Salmonella* strain) as illustrated in FIG. 19.

Example 7. Testing of Reproduction-Deficient SEA1 Indicator Phage Specific for Wild-Type and Permissive *Salmonella*

Figure 20:
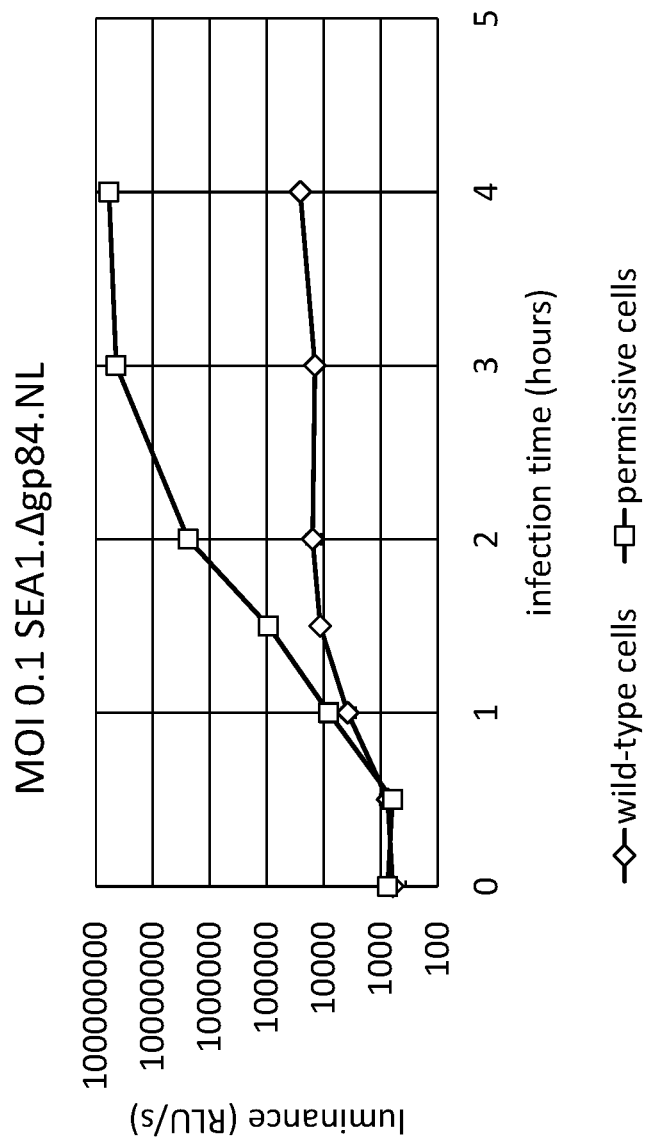
FIG. 20 is a line graph illustrating the raw signal results of the detection assay using the SEA1.Δgp84.NanoLuc reproduction-deficient indicator phage in wild-type *Salmonella* compared to permissive *Salmonella*.

Time course infection of wild-type *Salmonella* 27869 was compared to pUC57.trans.SEA1.gp84 transformed 27869 permissive cells. 1.0×10⁶ cells/well of either wild-type *Salmonella* 27869 (in 200 µl of TSB) or pUC57.trans.SEA1.gp84 transformed 27869 permissive cells (in 200 µl of TSB+carb) were incubated with recombinant bacteriophages (MOI of 0.1) in triplicate. NanoGlo assays were performed on 10 µl samples over 4 hours at 37° C. The signal produced by reproduction deficient recombinant phages in wild-type *Salmonella* plateaued early and low, demonstrating a lack of sustained growth of phage in wild-type *Salmonella* (FIG. 20). However, the signal in permissive *Salmonella* continued to increase over time, indicating that multiple rounds of infection and continued growth (FIG. 20).

Figure 21:
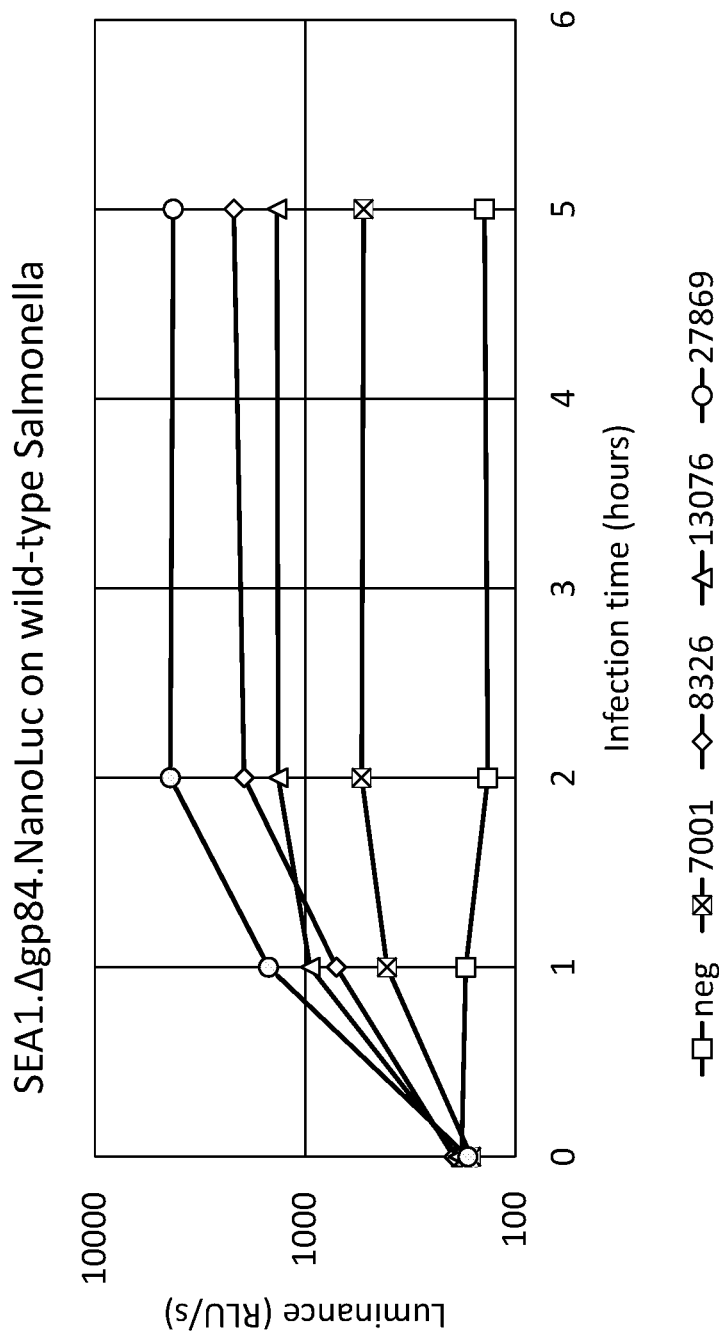
FIG. 21 is a line graph illustrating the raw signal results of the detection assay using the SEA1.Δgp84.NanoLuc reproduction-deficient indicator phage in wild-type *Salmonella* strains 7001, 8326, 13076, and 27869.

Next, a time course infection of wild-type *Salmonella* strains 7001, 8326, 13076, and 27869 was performed. 1.0× 10⁶ cells/well of each wild-type *Salmonella* strain was incubated with recombinant bacteriophages (MOI of 0.01) in 100 µl of TSB. NanoGlo assays were performed on 10 µl samples at 0, 1, 2, and 5 hours at 37° C. The signal produced by reproduction deficient recombinant phages in wild-type *Salmonella* plateaued early and low (FIG. 21).

Figure 22:
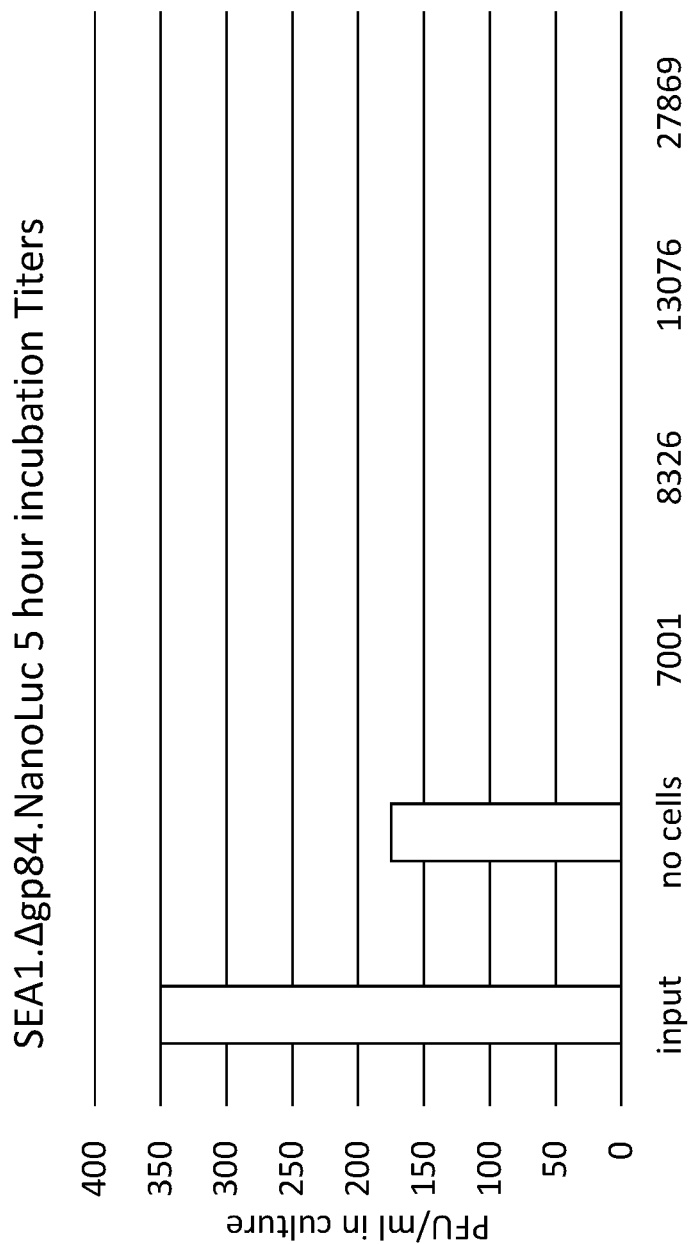
FIG. 22 is a bar graph illustrating a plaque assay of replication of SEA1.Δgp84.NanoLuc reproduction-deficient indicator phage on wild-type *Salmonella* strains 7001, 8326, 13076, and 27869.

Replication of SEA1.Δgp84.NanoLuc bacteriophages on wild-type *Salmonella* strains was assessed by performing plaque assays of 5 hour wild-type cultures (40 µl culture). No plaques formed from cultures of wild-type *Salmonella* strains 7001, 8326, 13076, and 27869 (FIG. 22) confirming a lack of replication of SEA1.Δgp84.NanoLuc on wild-type *Salmonella* strains.

Example 8. Testing of Reproduction-Deficient SEA1 Indicator Phage Specific for *Salmonella* Limit of Detection To assess the limit of detection of SEA1.Δgp84.NanoLuc reproduction-deficient indicator phage, *Salmonella* Newport ATCC 27869 was transformed with AmpR puc57.SEA1.Trans gp84. Log phase culture was diluted in TSB and cells were transferred to a 96 well plate according to the plate layout shown in FIG. 23. SEA1.Δgp84.NanoLuc phage were added to the *Salmonella* log phase culture and incubated for two hours at 37° C. Following infection with the phage, lysis buffer, assay buffer, and substrate were added, and the plate was read for 1 second in a luminometer. Results are shown in FIG. 23.

To assess the limit of detection of SEA1.Δgp84.NanoLuc reproduction-deficient indicator phage in stationary phase *Salmonella*, *Salmonella chloreaesuis* ATCC 27869 was grown 18-20 hours to stationary phase. Stationary phase cells were then diluted in TSB and cells were transferred to a 96 well plate according to the plate layout shown in FIG. 24. SEA1.Δgp84.NanoLuc phage were added to the *Salmonella* stationary phase culture and incubated for two hours at 37° C. Following infection with the phage, lysis buffer, assay buffer, and substrate were added, and the plate was read for 1 second in a luminometer. Results are shown in FIG. 24.

To assess the limit of detection of SEA1.Δgp84.NanoLuc reproduction-deficient indicator phage in log phase *Salmonella*, *Salmonella chloreaesuis* ATCC 27869 was grown 18-20 hours to stationary phase. Stationary phase cells were then diluted in TSB and grown to early log phase. Then the log phase culture was diluted in TSB and cells were transferred to a 96 well plate according to the plate layout shown in FIG. 25. SEA1.Δgp84.NanoLuc phage were added to the Salmonella stationary phase culture and incubated for two hours at 37° C. Following infection with the phage, lysis buffer, assay buffer, and substrate were added, and the plate was read for 1 second in a luminometer. Results are shown in FIG. 25.

Example 9. Testing of Reproduction-Deficient SEA1 Indicator Phage Specific for *Salmonella* in a Detection Assay To assess the activity of SEA1. Δp84.NanoLuc reproduction-deficient indicator phage, its detection activity was compared to that of SEA1 NanoLuc, a reproduction-capable indicator phage specific for *Salmonella*, with the NANO-LUC® gene inserted after gp84. Each sample was infected with either SEA1 NanoLuc or SEA1. Δp84.NanoLuc for 2 hours and 4 hours at 37° C. Lysis buffer and luciferase substrate were added and the samples were read on a luminometer. Five replicates of the measurements were performed at each CFU level for each phage as shown in FIG. 26A. RLU values for each CFU are shown in FIG. 26B (2 hour infection) and FIG. 26C (4 hour infection).

That which is claimed:

1. A reproduction-deficient recombinant phage, comprising an indicator gene inserted into a late gene region of the phage genome, wherein one or more late genes required for virion assembly are deleted or altered in the recombinant phage, thereby rendering the recombinant phage reproduction-deficient, and wherein the recombinant phage is capable of specifically infecting a microorganism of interest.

2. The recombinant phage of claim 1, wherein the indicator gene is inserted into a sequence of a late gene of the recombinant phage, rendering the late gene non-functional and the recombinant phage reproduction-deficient.

3. The recombinant phage of claim 1, wherein the indicator gene replaces at least a portion of a sequence of a late gene of the recombinant phage, rendering the recombinant phage reproduction deficient, wherein the late gene is required for virion assembly.

4. The recombinant phage of claim 1, wherein the recombinant phage is derived from a phage specific for *E. coli*, or *Salmonella*, or *Listeria*, or *Staphylococcus*.

5. A composition comprising at least two reproduction-deficient recombinant phages, each comprising an indicator gene inserted into a late gene region of the phage genome, wherein one or more late genes required for virion assembly are deleted or altered in the recombinant phage, thereby rendering the recombinant phages reproduction-deficient, and wherein the recombinant phages are capable of specifically infecting one or more microorganism of interest.

6. The composition of claim 5, wherein each of the at least two recombinant phages comprises a different indicator gene.

7. The composition of claim 6, wherein each of the at least two recombinant phages is capable of specifically infecting a different microorganism of interest.

8. The composition of claim 6, wherein the at least two recombinant phages are capable of infecting a plurality of microorganisms of interest.

9. The composition of claim 5, wherein the microorganism of interest comprises at least one of *E. coli, Salmonella, Listeria*, and *Staphylococcus*.

10. The composition of claim 8, wherein the plurality of the microorganisms of interest comprises at least two different categories of bacteria.

11. The composition of claim 10, wherein the at least two different categories of bacteria comprise one or more of at least two different genera of bacteria, at least two different species of bacteria, at least two different strains of bacteria or at least two different serotypes of bacteria.

12. A method of preparing a recombinant phage, comprising:
    selecting a parent phage that specifically infects a target microorganism;
    altering or deleting one or more late genes of the phage required for virion assembly to generate a recombinant reproduction-deficient phage;
    transforming an engineered strain of the target microorganism capable of expressing a product of the gene mutated in the reproduction-deficient phage with a homologous recombination (HR) plasmid comprising an indicator gene and HR sequences flanking the indicator gene and homologous to a desired sequence in the parent phage;
    infecting the transformed target microorganism with the parent phage or the reproduction-deficient parent phage, allowing HR to occur between the HR plasmid and the genome or the parent phage or the recombinant reproduction-deficient phage; and
    isolating a particular clone of recombinant phage that is both reproduction-deficient and is capable of expressing a product of the indicator gene.

13. The method of claim 12, wherein the altering of the gene of the parent page to generate the reproduction-deficient phage is accomplished by the HR occurring between the HR plasmid and the genome of the parent phage, wherein the gene of the parent page is altered by a replacement of at least a part of the parent phage by the indicator gene.

14. The method of claim 12, further comprising generating the engineered strain of the target microorganism.

15. The method of claim 14, wherein the generating of the engineered strain of the target microorganism comprises transforming the target microorganism with a plasmid encoding and capable of expressing the gene altered in the recombinant reproduction-deficient phage.

16. The method of claim 12, wherein the transforming the engineered strain further comprises transforming the engineered strain with a trans plasmid.

17. The method of claim 12, further comprising, prior to the transforming, preparing the homologous recombination plasmid comprising the indicator gene.

18. The method of claim 12, wherein the isolating the particular clone of recombinant phage that is both reproduction-deficient and is capable of expressing the product of the indicator gene comprises performing a limiting dilution assay for isolating a clone that demonstrates expression of the indicator gene.

19. The method of claim 12, wherein the recombinant phage is derived from a phage specific for *E. coli*, or *Salmonella*, or *Listeria*, or *Staphylococcus*.

20. A method of detecting a microorganism of interest in a sample, comprising:
    incubating a sample with the recombinant phage of claim 1; and,
    detecting a product of the indicator gene, wherein positive detection of the product of the indicator gene indicates that the microorganism of interest is present in the sample.

21. The method of claim 20, wherein the sample is a food, environmental, water, or commercial sample.

22. The method of claim 20, wherein the method detects as few as 10, 9, 8, 7, 6, 5, 4, 3, 2, or a single microorganism in the sample.

23. The method of claim 20, wherein the microorganism of interest is *E. coli*, or *Salmonella*, or *Listeria*, or *Staphylococcus*.

24. The method of claim 20, wherein the microorganism of interest is *Salmonella*.

25. A kit for detecting the microorganism of interest in a sample comprising the recombinant phage of claim 1 and a substrate for reacting with a product of the indicator gene to detect the product of the indicator gene.

26. A system for detecting the microorganism of interest comprising the recombinant phage of claim 1 and a component for detecting a product of the indicator gene.

* * * * *